US010072053B2

(12) United States Patent
Hearl et al.

(10) Patent No.: US 10,072,053 B2
(45) Date of Patent: Sep. 11, 2018

(54) NUCLEIC ACIDS FOR TREATMENT OF ALLERGIES

(71) Applicant: Immunomic Therapeutics, Inc., Rockville, MD (US)

(72) Inventors: William Hearl, Rockville, MD (US); Teri Heiland, New Market, MD (US)

(73) Assignee: Immunomic Therapeutics, Inc., Rockville, MD (US)

( * ) Notice: Subject to any disclaimer, the term of this patent is extended or adjusted under 35 U.S.C. 154(b) by 0 days.

(21) Appl. No.: 15/663,871

(22) Filed: Jul. 31, 2017

(65) Prior Publication Data

US 2018/0009857 A1    Jan. 11, 2018

Related U.S. Application Data

(62) Division of application No. 14/407,410, filed as application No. PCT/US2012/042552 on Jun. 15, 2012.

(51) Int. Cl.
| *A01N 63/00* | (2006.01) |
| *A61K 48/00* | (2006.01) |
| *C07H 21/02* | (2006.01) |
| *C07H 21/04* | (2006.01) |
| *C07K 14/415* | (2006.01) |
| *A61K 39/36* | (2006.01) |
| *A61K 39/35* | (2006.01) |
| *A61K 39/00* | (2006.01) |

(52) U.S. Cl.
CPC .......... *C07K 14/415* (2013.01); *A61K 39/35* (2013.01); *A61K 39/36* (2013.01); *A61K 2039/53* (2013.01); *A61K 2039/55505* (2013.01); *A61K 2039/577* (2013.01); *A61K 2039/70* (2013.01)

(58) Field of Classification Search
None
See application file for complete search history.

(56) References Cited

U.S. PATENT DOCUMENTS

| 5,633,234 | A | 5/1997 | August et al. |
| 6,090,386 | A | 7/2000 | Griffith et al. |
| 6,486,311 | B1 | 11/2002 | Burks et al. |
| 6,982,326 | B1 | 1/2006 | Griffith et al. |
| 7,112,329 | B1 | 9/2006 | Kino et al. |
| 7,547,440 | B2 | 6/2009 | Kino et al. |
| 7,566,456 | B2 | 7/2009 | Chen |
| 9,744,230 | B2 | 8/2017 | Hearl et al. |
| 2004/0157307 | A1 | 8/2004 | Harris et al. |
| 2006/0003148 | A1 | 1/2006 | Zwynenburg et al. |
| 2008/0006554 | A1 | 1/2008 | Duffy et al. |

FOREIGN PATENT DOCUMENTS

| JP | H0847392 A | 2/1996 |
| WO | 1994011512 A9 | 7/1994 |
| WO | 1994024281 A1 | 10/1994 |
| WO | 9707218 | 2/1997 |
| WO | 2001076642 A1 | 10/2001 |
| WO | 2002074250 A2 | 9/2002 |
| WO | 2002080851 A2 | 10/2002 |
| WO | 2006099574 A3 | 12/2006 |
| WO | 2007024026 A1 | 3/2007 |
| WO | 2006138435 A3 | 11/2007 |
| WO | 2009040443 A1 | 4/2009 |

OTHER PUBLICATIONS

Batzer, et al. "Enhanced Evolutionary PCR Using Oligonucleotides with Inosine at the 3'-Terminus" Nucleic Acid Res., Jul. 12, 1991 vol. 19(18), p. 5081.
Blott, et al. "Secretory lysosomes", Nature Reviews Molecular Cell Biology, Feb. 2002, pp. 122-131.
Bork et al. 'Powers and Pitfalls in Sequence Analysis: The 70% Hurdle.' Gen. Res. 10:398-400, 2000.
Bowie et al. "Deciphering the Message in Protein Sequences: Tolerance to Amino Acid Substitutions" Science 247:1306-1310, 1990.
Brenner S. 'Errors in Genome Annotation.' Trends in Genetics 15:132-133, 1999.
Bublin et al. "Developing Therapies for Peanut Allergy" International Archives of Allergy and Immunology, vol. 165, pp. 179-194, (2014).
Cabanos C. et al. "Crystal Structure of the Major Peanut Allergen ARA H 1" Mol. Immunol. vol. 49 p. 115 (2011).
Chen et al., "Identification of Methylated CpG Motifs as Inhibitors of the Immune Stimulatory CpG Motifs", Nature Publishing Group, Gene Therapy, 8, 1024-1032 (2001).
Chua et al., "DNA vaccines for the prevention and treatment of allergy", Current Opinion in Allergy and Clinical Immunology, Feb. 1, 2009, vol. 9, No. 1, 50-54.
Crameri et al., "Design, Engineering and In Vitro Evaluation of MHC Class-II Targeting Allergy Vaccines", Allergy, 62: 197-206 (2007).
De Duve, "Lysosomes Revisited", Eur. J., Biochem., Dec. 1983, 137(3), 391-97.
Dell' Angelica, et al., "Lysosome-Related Organelles", The FASEB Journal, vol. 14(10), Jul. 2000, pp. 1265-1278.
Doerks et al. 'Protein annotation: detective work for function prediction.' Trends in Genetics. 14:248-250, 1998.

(Continued)

*Primary Examiner* — Nora Rooney
(74) *Attorney, Agent, or Firm* — Michele M. Wales; Inhouse Patent Counsel, LLC

(57) ABSTRACT

The present invention provides DNA vaccines for the treatment of allergies. The vaccines comprise the coding sequence for one or more allergenic epitopes, and preferably the full protein sequence, of the allergenic protein from which the epitope(s) is derived, fused inframe with the lumenal domain of the lysosomal associated membrane protein (LAMP) and the targeting sequence of LAMP. The vaccines allow for presentation of properly configured three dimensional epitopes for production of an immune response. The vaccines can be multivalent molecules, and/or can be provided as part of a multivalent vaccine containing two or more DNA constructs.

28 Claims, 25 Drawing Sheets

Specification includes a Sequence Listing.

(56) References Cited

OTHER PUBLICATIONS

European Examination Report dated Oct. 26, 2016 issued in EP 12 878 776.9.
Extended European Search Report dated Feb. 11, 2016 issued in PCT/US2012/042552.
Fukuda, M., et al., Cloning of cDNAs Encoding Human Lysosomal Membrane Glycoproteins, H-LAMP-1 and H-LAMP-2. Comparison of Their Deduced Amino Acid Sequences, J. Biol. Chem. 263 (35), 18920-18928 (1988).
Hartl et al., 'DNA vaccines for allergy treatment.' Methods 32:328-339, 2004.
Haugaard et al., "A Controlled Dose-Response Study of Immunotherapy with Standardized, Partially Purified Extract of House Dust Mite: Clinical Efficacy and Side Effects", J Allergy Clin Immunol, vol. 91(3), No. 3, Mar. 1993, pp. 709-722.
Hotta, H., et al., "Molecular Cloning and Characterization of an Antigen Associated with Early Stages of Melanoma Tumor Progression," Cancer Res. 48 (11), 2955-2962 (1988).
Hsu et al., "Inhibition of Specific IgE Response In Vivo by Allergen-Gene Transfer", International Immunology, vol. 8, No. 9, pp. 1405-1411 (1996).
International Search Report and Written Opinion dated Jun. 24, 2013 issued in PCT/US2012/042552.
Ishii et al., "Anti-allergic potential of oligomannose-coated liposome-entrapped Cry j 1 as immunotherapy for Japanes cedar pollinosis in mice", Internat. Immunopharm., 2011, vol. 10, No. 9, 1041-1046.
Japanese Patent Application No. 2015-517226: Notification of Reason for Refusal dated Aug. 3, 2015, 9 pages.
Kaburaki et al., "Induction of Th1 immune responses to Japanese cedar pollen allergen (Cry j 1) in mice immunized with Cry j 1 conjugated with CpG oligodeoxynucleotide", Comparative Immunology, Microbiology and Infectious Diseases, 2011, vol. 34, No. 2, 157-161.
Kaech et al., "Effector and Memory T-Cell Differentiation: Implications for Vaccine Development", Nature Reviews vol. 2, 251-262 (2002).
Kohama et al., "Immunostimulatory oligodeoxynucleotide induces TH1 immune response and inhibition of IgE antibody production to cedar pollen allergens in mice", J. Allergy Clin. Immunol., 1999, vol. 104, No. 6, 1231-1238.
Kohno et al., "Regulation of Cytokine Production by Sugi Allergen-Pullulan Conjugate", Cellular Immunology, 1996, vol. 168, No. 2, 211-219.
Koppelman et al., "Relevance of Ara hl, Ara h2 and Ara h3 in Peanut-Allergic Patients, as Determined by Immunoglobulin E Western Blotting, Basophil-histamine Release and Intracutaneous Testing: Ara h2 is the Most Important Peanut Allergen", Clinical & Experimental Allergy : Journal of the British Society for Allergy and Clinical Immunology, vol. 34, No. 4, pp. 583-590, (2004).
Metzler et al. 'Solution structure of-uman CTLA-4 and delineation of a CD80/CD86 binding site conserved in CD28.' Nature Structural Biol. 4:527-531, 1997.
Office Action issued by Japanese Patent Office dated Aug. 16, 2016.
Office Action issued by State Intellectual Property Office of the People's Republic of China dated Sep. 17, 2015 (English translation included).
Office Action issued from Japanese Patent Office dated Aug. 3, 20, 2015.
Office of Action dated Jul. 6, 2017 received in corresponding European Application, Application No. 12 878 776.9.
Ohtsuka, et al., "An Alternative Approach to Deoxyoligonucleotides as Hybridization Probes by Insertion of Deoxyinosine at Ambiguous Codon Positions", J. Biol. Chem. 260(5), 1985, 2605-2608.
Ozaki, K., et al., "Isolation and Characterization of a Novel Human Lung-Specific Gene Homologous to Lysosomal Membrane Glycoproteins 1 and 2: Significantly Increased Expression in Cancers of Various Tissues," Cancer Res. 58 (16), 3499-3503 (1998).
Rabjohn, et al, "Molecular Cloning and Epitope Analysis of the Peanut Allergen Ara H 3" J Clin Invest., vol. 103, No. 4, p. 535 (1997)).
Raz et al., "Preferential Induction of a Th1 Immune Response and Inhibition of Specific IgE Antibody Formation by Plasmid DNA Immunization", Proc. Natl. Acad. Sci. USA, vol. 93, pp. 5141-5145 (1996).
Rossolini et al., Use of Deoxyinosine-Containing Primers vs Degenerate Primers for Polymerase Chain Reaction Based on Ambiguous Sequence Information Mol. Cell. Probes 8, Apr. 1994, vol. 8(2), pp. 91-98.
Second Office Action issued by State Intellectual Property Office of the People's Republic of China dated Aug. 8, 2016 (English translation included).
Smith et al. The challenges of genome sequence annotation or "the devil is in the details". Nat. Biotech.15: 1222-1223, 1997.
Takeno et al., "Th1-dominant shift of T cell cytokine production, and subsequent reduction of serum immunoglobulin E response by administration in vivo of plasmid expressing Txk/Rlk, a member of Tec family tyrosine kinases, in a mouse model", Clin. Experiment. Allergy, 2004, vol. 34, No. 6, 965-970.
Tan et al., "Intramuscular Immunization with DNA Construct Containing Der p. 2 and Signal Peptide Sequences Piimed Strong IgE Production", Vaccine, vol. 24, pp. 5762-5771, (2006).
Third Office Action issued by State Intellectual Property Office of the People's Republic of China dated Mar. 23, 2017 (English translation included).
Toda et al., "DNA vaccine using invariant chain gene for delivery of CD4+ T cell epitope peptide derived from Japanese cedar pollen allergen inhibits allergen-specific IgE response", Eur. J. Immunol., 2002, vol. 32, No. 6, 1631-1639.
Tsunematsu et al., "Effect of Cry-consensus Peptide, a Novel Recombinant Peptide for Immunotherapy of Japanese Cedar Pollinosis, on an Experimental Allergic Rhinitis Model in B10.S Mice", Allergol. Int., 2007, vol. 56, No. 4, 465-472.
Weiss et al., "Is Genetic Vaccination Against Allergy Possible?", International Archives of Allergy and Immunology, Jan. 1, 2006, vol. 139, No. 4, 332-345.
Yamashita et al., "Method of Inducing Th1 cells", Progression of Medical Science, 1997, vol. 180, No. 1, 85-89.
Zhu et al., "Arachis Hypogaea (Peanut) Seed Storage Protein Iso-ARA H3 mRNA Complete Sequence" Crop Protection and Management Research, #198426 (2006).
Final Office Action dated Apr. 19, 2017 received in U.S. Appl. No. 15/058,224.
GenBank ID: 080280_ARAHY (Nov. 1, 1998).
Guo, B. et al., "Arachis Hypogaea (Peanut) Seed Storage Protein ISO-ARA H3 MRNA Complete Sequence", GenBank National Center for Biotechnology Information Accession No. DQ855115. Available: http://www.ncbi.nlm.nih.gov., (2006).
Kuby, "Vaccines", Immunology, 4th Edition, Chapter 18, pp. 449-465, (2001).
Kurucz, I. and Szelenyi, I., "Current Animal Models of Bronchial Asthma", Current Pharmaceutical Design, vol. 12, pp. 3175-3194, (2006).
Marques, E. et al., "HIV-1 p55Gag Encoded in the Lysosome-Associated Membrane Protein-1 as a DNA Plasmid Vaccine Chimera is Highly Expressed, Traffics to the Major Histocompatibility Class II Compartment, and Elicits Enhanced Immune Responses", The Journal of Biological Chemistry, vol. 278, No. 39, pp. 37926-37936, (2003).
Mukherjee, A. and Zhang, Z., "Allergic Asthma: Influence of Genetic and Environmental Factors", Journal of Biological Chemistry, vol. 286, No. 38, pp. 32883-32889, (2011).
Office Action—Notification of Reason for Refusal dated Oct. 13, 2017 received in corresponding Chinese Application 2016-223108.
Office Action dated Apr. 19, 2017 received in U.S. Appl. No. 15/058,224.
Office Action dated Dec. 12, 2016 received in U.S. Appl. No. 15/058,224.
Office Action dated Oct. 5, 2017 received in U.S. Appl. No. 14/407,410.

(56) References Cited

OTHER PUBLICATIONS

Office Communication dated Dec. 27, 2010 received in U.S. Appl. No. 10/026,931.
Ratnaparkhe, M. et al., "Comparative and Evolutionary Analysis of Major Peanut Allergen Gene Families", Genome Biology Evolution, vol. 6, No. 9, pp. 2468-2488, doi: 10.1093/gbe/evu189, (2014).
Tan, L.K. et al., "Intramuscular Immunization with DNA Construct Containing Der p. 2 and Signal Peptide Sequences Primed Strong IgE Production", Vaccine, vol. 24, pp. 5762-5771, (2006).
Zhou, Y. et al., "Peanut Allergy, Allergen Composition, and Methods of Reducing Allergenicity: A Review", International Journal of Food Science, Article ID 909140, pp. 1-9, (2013).

SEQUENCE LISTING

```
<160> NUMBER OF SEQ ID NOS: 32

<210> SEQ ID NO 1
<211> LENGTH: 2898
<212> TYPE: DNA
<213> ORGANISM: Artificial Sequence
<220> FEATURE:
<223> OTHER INFORMATION: Description of Artificial Sequence: Synthetic
      pITI plasmid polylnucleotide

<400> SEQUENCE: 1
```

-continued

```
ccgcctaatg agcgggcttt tttttcttag gccttcttcc gcttcctcgc tcactgactc    60
gctgcgctcg gtcgttcggc tgcggcgagc ggtatcagct cactcaaagg cggtaatacg   120
gttatccaca gaatcagggg ataacgcagg aaagaacatg tgagcaaaag gccagcaaaa   180
ggccaggaac cgtaaaaagg ccgcgttgct ggcgtttttc cataggctcc gcccccctga   240
cgagcatcac aaaaatcgac gctcaagtca gaggtggcga acccgacag  gactataaag   300
ataccaggcg tttccccctg gaagctccct cgtgcgctct cctgttccga ccctgccgct   360
taccggatac ctgtccgcct ttctcccttc gggaagcgtg gcgctttctc atagctcacg   420
ctgtaggtat ctcagttcgg tgtaggtcgt tcgctccaag ctgggctgtg tgcacgaacc   480
ccccgttcag cccgaccgct gcgccttatc cggtaactat cgtcttgagt ccaacccggt   540
aagacacgac ttatcgccac tggcagcagc cactggtaac aggattagca gagcgaggta   600
tgtaggcggt gctacagagt tcttgaagtg gtggcctaac tacggctaca ctagaagaac   660
agtatttggt atctgcgctc tgctgaagcc agttaccttc ggaaaaagag ttggtagctc   720
ttgatccggc aaacaaacca ccgctggtag cggtggtttt tttgtttgca agcagcagat   780
tacgcgcaga aaaaaggat  ctcaagaaga tcctttgatc ttttctacgg ggtctgacgc   840
tcagtggaac gaaaactcac gttaagggat tttggtcatg agattatcaa aaaggatctt   900
cacctagatc cttttaaatt aaaaatgaag ttttaaatca atctaaagta tatatgagta   960
aacttggtct gacagttacc aatgcttaat cagtgaggca cctatctcag cgatctgtct  1020
atttcgttca tccatagttg cctgactccc tgcaaaccacg ttgtggtaga attggtaaag  1080
agagtcgtgt aaaatatcga gttcgcacat cttgttgtct gattattgat ttttggcgaa  1140
accatttgat catatgacaa gatgtgtatc taccttaact taatgatttt gataaaaatc  1200
attaggtacc ccggctctag atggcatgac attaacctat aaaaataggc gtatcacgag  1260
gccctttcgt ctcgcgcgtt tcggtgatga cggtgaaaac ctctgacaca tgcagctccc  1320
ggagacggtc acagcttgtc tgtaagcgga tgccgggagc agacaagccc gtcagggcgc  1380
gtcagcgggt gttggcgggt gtcggggctg gcttaactat gcggcatcag agcagattgt  1440
actgagagtg caccatatgc ggtgtgaaat accgcacaga tgcgtaagga gaaaataccg  1500
catcagattg gctattggcc attgcatacg ttgtatccat atcataatat gtacatttat  1560
attggctcat gtccaacatt accgccatgt tgacattgat tattgactag ttattaatag  1620
taatcaatta cggggtcatt agttcatagc ccatatatgg agttccgcgt tacataactt  1680
acggtaaatg gcccgcctgg ctgaccgccc aacgaccccc gcccattgac gtcaataatg  1740
acgtatgttc ccatagtaac gccaataggg actttccatt gacgtcaatg ggtggagtat  1800
ttacggtaaa ctgcccactt ggcagtacat caagtgtatc atatgccaag tacgccccct  1860
attgacgtca atgacggtaa atggcccgcc tggcattatg cccagtacat gaccttatgg  1920
gactttccta cttggcagta catctacgta ttagtcatcg ctattaccat ggtgatgcgg  1980
ttttggcagt acatcaatgg gcgtggatag cggtttgact cacggggatt tccaagtctc  2040
cacccccattg acgtcaatgg gagtttgttt tggcaccaaa atcaacggga ctttccaaaa  2100
tgtcgtaaca actccgcccc attgacgcaa atgggcggta ggcgtgtacg gtgggaggtc  2160
tatataagca gagctcgttt agtgaaccgt cagatcgcct ggagacgcca tccacgctgt  2220
tttgacctcc atagaagaca ccgggaccga tccagcctcc gcggctcgca tctctccttc  2280
acgcgcccgc cgccctacct gaggccgcca tccacgccgg ttgagtcgcg ttctgccgcc  2340
tcccgcctgt ggtgcctcct gaactgcgtc cgccgtctag gtaagtttaa agctcaggtc  2400
```

```
gagaccgggc ctttgtccgg cgctcccttg gagcctacct agactcagcc ggctctccac    2460
gctttgcctg accctgcttg ctcaactcta gttctctcgt taacttaatg agacagatag    2520
aaactggtct tgtagaaaca gagtagtcgc ctgcttttct gccaggtgct gacttctctc    2580
ccctgggctt ttttctttttt ctcaggttga aagaagaag acgaagaaga cgaagaagac    2640
aaagccgcca ccatggatgc aatgaagaga gggctctgct gtgtgctgct gctgtgtgga    2700
gcagtcttcg tttcgcccag cggtaccgga tccgtcgacg gggggagatc tttttccctc    2760
tgccaaaaat tatggggaca tcatgaagcc ccttgagcat ctgacttctg ctaataaag     2820 gaaatttatt ttcattgcaa tagtgtgttg aattttttg tgtctctcac tcggaaggac    2880
ataagggcgg ccgctagc                                                  2898

<210> SEQ ID NO 2
<211> LENGTH: 4157
<212> TYPE: DNA
<213> ORGANISM: Cryptomeria japonica

<400> SEQUENCE: 2
ccgcctaatg agcgggcttt ttttcttag ggtgcaaaag gagagcctgt aagcgggcac      60
tcttccgtgg tctggtggat aaattcgcaa gggtatcatg gcggacgacc ggggttcgag    120 cccgtatcc ggccgtccgc cgtgatccat gcgttaccg cccgcgtgtc gaacccaggt     180
gtgcgacgtc agacaacggg ggagtgctcc ttttggcttc cttccccttc ttccgcttcc    240
tcgctcactg actcgctgcg ctcggtcgtt cggctgcggc gagcggtatc agctcactca    300
aaggcggtaa tacggttatc cacagaatca ggggataacg caggaaagaa catgtgagca    360
aaaggccagc aaaaggccag gaaccgtaaa aaggccgcgt tgctggcgtt tttccatagg    420
ctccgccccc ctgacgagca tcacaaaaat cgacgctcaa gtcagaggtg gcgaaacccg    480
acaggactat aaagatacca ggcgtttccc cctggaagct ccctcgtgcg ctctcctgtt    540
ccgaccctgc cgcttaccgg atacctgtcc gcctttctcc cttcgggaag cgtggcgctt    600
tctcatagct cacgctgtag gtatctcagt tcggtgtagg tcgttcgctc caagctgggc    660
tgtgtgcacg aaccccccgt tcagcccgac cgctgcgcct tatccggtaa ctatcgtctt    720
gagtccaacc cggtaagaca cgacttatcg ccactggcag cagccactgg taacaggatt    780
agcagagcga ggtatgtagg cggtgctaca gagttcttga agtggtggcc taactacggc    840
tacactagaa gaacagtatt tggtatctgc gctctgctga gccagttac cttcggaaaa    900 agagttggta gctcttgatc cggcaaacaa accaccgctg gtagcggtgg ttttttgtt     960 tgcaagcagc agattacgcg cagaaaaaaa ggatctcaag aagatccttt gatctttcct    1020
acggggtctg acgctcagtg gaacgaaaac tcacgttaag ggattttggt catgagatta    1080
tcaaaaagga tcttcaccta gatcctttta aattaaaaat gaagttttaa atcaatctaa    1140
agtatatatg agtaaacttg gtctgacagt taccaatgct taatcagtga ggcacctatc    1200
tcagcgatct gtctatttcg ttcatccata gttgcctgac tcctgcaaac cacgttgtgg    1260
tagaattggt aaagagagtc gtgtaaaata tcgagttcgc acatcttgtt gtctgattat    1320
tgattttggg cgaaaccatt tgatcatatg acaagatgtg tatctacctt aacttaatga    1380
ttttgataaa aatcattagg taccccggct ctagatggca tgacattaac ctataaaaat    1440
aggcgtatca cgaggccctt tcgtctcgcg cgtttcggtg atgacggtga aaacctctga    1500
cacatgcagc tcccggagac ggtcacagct tgtctgtaag cggatgccgg gagcagacaa    1560
```

```
gcccgtcagg gcgcgtcagc gggtgttggc gggtgtcggg gctggcttaa ctatgcggca    1620
tcagagcaga ttgtactgag agtgcaccat atgcggtgtg aaataccgca cagatgcgta    1680
aggagaaaat accgcatcag attggctatt ggccattgca tacgttgtat ccatatcata    1740
atatgtacat ttatattggc tcatgtccaa cattaccgcc atgttgacat tgattattga    1800
ctagttatta atagtaatca attacgggt cattagttca tagcccatat atggagttcc     1860
gcgttacata acttacggta aatggcccgc ctggctgacc gcccaacgac ccccgcccat    1920
tgacgtcaat aatgacgtat gttcccatag taacgccaat agggactttc cattgacgtc    1980
aatgggtgga gtatttacgg taaactgccc acttggcagt acatcaagtg tatcatatgc    2040
caagtacgcc ccctattgac gtcaatgacg gtaaatggcc cgcctggcat tatgcccagt    2100
acatgacctt atgggacttt cctacttggc agtacatcta cgtattagtc atcgctatta    2160
ccatggtgat gcggttttgg cagtacatca atgggcgtgg atagcggttt gactcacggg    2220
gatttccaag tctccacccc attgacgtca atgggagttt gttttggcac caaaatcaac    2280
gggactttcc aaaatgtcgt aacaactccg ccccattgac gcaaatgggc ggtaggcgtg    2340
tacggtggga ggtctatata agcagagctc gtttagtgaa ccgtcagatc gcctggagac    2400
gccatccacg ctgttttgac ctccatagaa gacaccggga ccgatccagc ctccgcggct    2460
cgcatctctc cttcacgcgc ccgccgccct acctgaggcc gccatccacg ccggttgagt    2520
cgcgttctgc cgcctcccgc ctgtggtgcc tcctgaactg cgtccgccgt ctaggtaagt    2580
ttaaagctca ggtcgagacc gggcctttgt ccggcgctcc cttggagcct acctagactc    2640
agccggctct ccacgctttg cctgaccctg cttgctcaac tctagttctc tcgttaactt    2700
aatgagacag atagaaactg gtcttgtaga aacagagtag tcgcctgctt ttctgccagg    2760
tgctgacttc tctcccctgg gcttttttct ttttctcagg ttgaaaagaa gaagacgaag    2820
aagacgaaga agacaaaccg tcgtcgacat ggcgccccgc agcgcccggc gaccccctgct   2880 gctgctactg ctgttgctgc tgctcggcct catgcattgt gcgtcagcag caatgtttat    2940
ggtgaaaaat ggcaacggga ccgcgtgcat aatggccaac ttctctgctg ccttctcagt    3000
gaactacgac accaagagtg gccctaagaa catgacccct tgacctgcca tcagatgccac   3060 agtggtgctc aaccgcagct cctgtggaaa agagaacact tctgaccca gtctcgtgat    3120 tgcttttgga agaggacata cactcactct caatttcacg agaaatgcaa cacgttacag    3180
cgttcagctc atgagttttg tttataactt gtcagacaca caccttttcc ccaatgcgag    3240
ctccaaagaa atcaagactg tggaatctat aactgacatc agggcagata tagataaaaa    3300
atacagatgt gttagtggca cccaggtcca catgaacaac gtgaccgtaa cgctccatga    3360
tgccaccatc caggcgtacc tttccaacag cagcttcagc aggggagaga cacgctgtga    3420
acaagacagg ccttccccaa ccacagcgcc cctgcgcca cccagcccct cgccctcacc      3480
cgtgcccaag agccctctg tggacaagta caacgtgagc ggcaccaacg ggacctgcct     3540
gctggccagc atggggctgc agctgaacct cacctatgag aggaaggaca cacgacggt      3600 gacaaggctt ctcaacatca accccaacaa gacctcggcc agcgggagct gcggcgccca    3660
cctggtgact ctggagctgc acagcgaggg caccaccgtc ctgctcttcc agttcgggat    3720
gaatgcaagt tctagccggt ttttcctaca aggaatccag ttgaatacaa ttcttcctga    3780
cgccagagac cctgccttta aagctgccaa cggctccctg cgagcgctgc aggccacagt    3840
cggcaattcc tacaagtgca acgcggagga gcacgtccgt gtcacgaagg cgttttcagt    3900
caatatattc aaagtgtggg tccaggcttt caaggtggaa ggtggccagt ttggctctgt    3960
```

```
ggaggagtgt ctgctggacg agaacagcct cgaggatcag tcagcgcaga tcatgctgga    4020
tagcgtggtg gagaagtacc tgaggagtaa caggtcactg cgcaaggttg agcattccag    4080
acacgacgct atcaacatct tcaacgtgga gaagtacggt gctgtcggag acgggaagca    4140
cgactgcacc gaagcct                                                   4157
```

<210> SEQ ID NO 3
<211> LENGTH: 911
<212> TYPE: PRT
<213> ORGANISM: Cryptomeria japonica

<400> SEQUENCE: 3

```
Met Ala Pro Arg Ser Ala Arg Arg Pro Leu Leu Leu Leu Leu Leu
1               5                   10                  15

Leu Leu Leu Gly Leu Met His Cys Ala Ser Ala Ala Met Phe Met Val
                20                  25                  30

Lys Asn Gly Asn Gly Thr Ala Cys Ile Met Ala Asn Phe Ser Ala Ala
            35                  40                  45

Phe Ser Val Asn Tyr Asp Thr Lys Ser Gly Pro Lys Asn Met Thr Leu
        50                  55                  60

Asp Leu Pro Ser Asp Ala Thr Val Val Leu Asn Arg Ser Ser Cys Gly
65                  70                  75                  80

Lys Glu Asn Thr Ser Asp Pro Ser Leu Val Ile Ala Phe Gly Arg Gly
                85                  90                  95

His Thr Leu Thr Leu Asn Phe Thr Arg Asn Ala Thr Arg Tyr Ser Val
            100                 105                 110

Gln Leu Met Ser Phe Val Tyr Asn Leu Ser Asp Thr His Leu Phe Pro
        115                 120                 125

Asn Ala Ser Ser Lys Glu Ile Lys Thr Val Glu Ser Ile Thr Asp Ile
    130                 135                 140

Arg Ala Asp Ile Asp Lys Lys Tyr Arg Cys Val Ser Gly Thr Gln Val
145                 150                 155                 160

His Met Asn Asn Val Thr Val Thr Leu His Asp Ala Thr Ile Gln Ala
                165                 170                 175

Tyr Leu Ser Asn Ser Ser Phe Ser Arg Gly Glu Thr Arg Cys Glu Gln
            180                 185                 190

Asp Arg Pro Ser Pro Thr Thr Ala Pro Pro Ala Pro Pro Ser Pro Ser
        195                 200                 205

Pro Ser Pro Val Pro Lys Ser Pro Ser Val Asp Lys Tyr Asn Val Ser
    210                 215                 220

Gly Thr Asn Gly Thr Cys Leu Leu Ala Ser Met Gly Leu Gln Leu Asn
225                 230                 235                 240

Leu Thr Tyr Glu Arg Lys Asp Asn Thr Thr Val Thr Arg Leu Leu Asn
                245                 250                 255

Ile Asn Pro Asn Lys Thr Ser Ala Ser Gly Ser Cys Gly Ala His Leu
            260                 265                 270

Val Thr Leu Glu Leu His Ser Glu Gly Thr Thr Val Leu Leu Phe Gln
        275                 280                 285

Phe Gly Met Asn Ala Ser Ser Ser Arg Phe Phe Leu Gln Gly Ile Gln
    290                 295                 300

Leu Asn Thr Ile Leu Pro Asp Ala Arg Asp Pro Ala Phe Lys Ala Ala
305                 310                 315                 320

Asn Gly Ser Leu Arg Ala Leu Gln Ala Thr Val Gly Asn Ser Tyr Lys
                325                 330                 335
```

```
Cys Asn Ala Glu Glu His Val Arg Val Thr Lys Ala Phe Ser Val Asn
            340                 345                 350

Ile Phe Lys Val Trp Val Gln Ala Phe Lys Val Glu Gly Gly Gln Phe
            355                 360                 365

Gly Ser Val Glu Glu Cys Leu Leu Asp Glu Asn Ser Leu Glu Asp Gln
            370                 375                 380

Ser Ala Gln Ile Met Leu Asp Ser Val Glu Lys Tyr Leu Arg Ser
385                 390                 395                 400

Asn Arg Ser Leu Arg Lys Val Glu His Ser Arg His Asp Ala Ile Asn
                405                 410                 415

Ile Phe Asn Val Glu Lys Tyr Gly Ala Val Gly Asp Gly Lys His Asp
            420                 425                 430

Cys Thr Glu Ala Phe Ser Thr Ala Trp Gln Ala Ala Cys Lys Asn Pro
            435                 440                 445

Ser Ala Met Leu Leu Val Pro Gly Ser Lys Lys Phe Val Asn Asn
            450                 455                 460

Leu Phe Phe Asn Gly Pro Cys Gln Pro His Phe Thr Phe Lys Val Asp
465                 470                 475                 480

Gly Ile Ile Ala Ala Tyr Gln Asn Pro Ala Ser Trp Lys Asn Asn Arg
                485                 490                 495

Ile Trp Leu Gln Phe Ala Lys Leu Thr Gly Phe Thr Leu Met Gly Lys
            500                 505                 510

Gly Val Ile Asp Gly Gln Gly Lys Gln Trp Trp Ala Gly Gln Cys Lys
            515                 520                 525

Trp Val Asn Gly Arg Glu Ile Cys Asn Asp Arg Asp Arg Pro Thr Ala
            530                 535                 540

Ile Lys Phe Asp Phe Ser Thr Gly Leu Ile Ile Gln Gly Leu Lys Leu
545                 550                 555                 560

Met Asn Ser Pro Glu Phe His Leu Val Phe Gly Asn Cys Glu Gly Val
                565                 570                 575

Lys Ile Ile Gly Ile Ser Ile Thr Ala Pro Arg Asp Ser Pro Asn Thr
            580                 585                 590

Asp Gly Ile Asp Ile Phe Ala Ser Lys Asn Phe His Leu Gln Lys Asn
            595                 600                 605

Thr Ile Gly Thr Gly Asp Asp Cys Val Ala Ile Gly Thr Gly Ser Ser
            610                 615                 620

Asn Ile Val Ile Glu Asp Leu Ile Cys Gly Pro Gly His Gly Ile Ser
625                 630                 635                 640

Ile Gly Ser Leu Gly Arg Glu Asn Ser Arg Ala Glu Val Ser Tyr Val
                645                 650                 655

His Val Asn Gly Ala Lys Phe Ile Asp Thr Gln Asn Gly Leu Arg Ile
            660                 665                 670

Lys Thr Trp Gln Gly Gly Ser Gly Met Ala Ser His Ile Ile Tyr Glu
            675                 680                 685

Asn Val Glu Met Ile Asn Ser Glu Asn Pro Ile Leu Ile Asn Gln Phe
            690                 695                 700

Tyr Cys Thr Ser Ala Ser Ala Cys Gln Asn Gln Arg Ser Ala Val Gln
705                 710                 715                 720

Ile Gln Asp Val Thr Tyr Lys Asn Ile Arg Gly Thr Ser Ala Thr Ala
                725                 730                 735

Ala Ala Ile Gln Leu Lys Cys Ser Asp Ser Met Pro Cys Lys Asp Ile
            740                 745                 750
```

```
Lys Leu Ser Asp Ile Ser Leu Lys Leu Thr Ser Gly Lys Ile Ala Ser
            755                 760                 765
Cys Leu Asn Asp Asn Ala Asn Gly Tyr Phe Ser Gly His Val Ile Pro
770                 775                 780
Ala Cys Lys Asn Leu Ser Pro Ser Ala Lys Arg Lys Glu Ser Lys Ser
785                 790                 795                 800
His Lys His Pro Lys Thr Val Met Val Glu Asn Met Arg Ala Tyr Asp
            805                 810                 815
Lys Gly Asn Arg Thr Arg Ile Leu Leu Gly Ser Arg Pro Pro Asn Cys
            820                 825                 830
Thr Asn Lys Cys His Gly Cys Ser Pro Cys Lys Ala Lys Leu Val Ile
            835                 840                 845
Val His Arg Ile Met Pro Gln Glu Tyr Tyr Pro Gln Arg Trp Ile Cys
850                 855                 860
Ser Cys His Gly Lys Ile Tyr His Pro Glu Phe Thr Leu Ile Pro Ile
865                 870                 875                 880
Ala Val Gly Gly Ala Leu Ala Gly Leu Val Leu Ile Val Leu Ile Ala
            885                 890                 895
Tyr Leu Val Gly Arg Lys Arg Ser His Ala Gly Tyr Gln Thr Ile
            900                 905                 910

<210> SEQ ID NO 4
<211> LENGTH: 5326
<212> TYPE: DNA
<213> ORGANISM: Cryptomeria japonica

<400> SEQUENCE: 4
ccgcctaatg agcgggcttt tttttcttag ggtgcaaaag gagagcctgt aagcgggcac      60
tcttccgtgg tctggtggat aaattcgcaa gggtatcatg gcggacgacc ggggttcgag     120
ccccgtatcc ggccgtccgc cgtgatccat gcggttaccg cccgcgtgtc gaacccaggt     180
gtgcgacgtc agacaacggg ggagtgctcc ttttggcttc cttccccttc ttccgcttcc     240
tcgctcactg actcgctgcg ctcggtcgtt cggctgcggc gagcggtatc agctcactca     300
aaggcggtaa tacggttatc cacagaatca ggggataacg caggaaagaa catgtgagca     360
aaaggccagc aaaaggccag gaaccgtaaa aaggccgcgt tgctggcgtt tttccatagg     420
ctccgccccc ctgacgagca tcacaaaaat cgacgctcaa gtcagaggtg gcgaaacccg     480
acaggactat aaagatacca ggcgtttccc cctggaagct ccctcgtgcg ctctcctgtt     540
ccgaccctgc cgcttaccgg atacctgtcc gcctttctcc cttcgggaag cgtggcgctt     600
tctcatagct cacgctgtag gtatctcagt tcggtgtagg tcgttcgctc caagctgggc     660
tgtgtgcacg aaccccccgt tcagcccgac cgctgcgcct tatccggtaa ctatcgtctt     720
gagtccaacc cggtaagaca cgacttatcg ccactggcag cagccactgg taacaggatt     780
agcagagcga ggtatgtagg cggtgctaca gagttcttga agtggtggcc taactacggc     840
tacactagaa gaacagtatt tggtatctgc gctctgctga agccagttac cttcggaaaa     900
agagttggta gctcttgatc cggcaaacaa accaccgctg gtagcggtgg tttttttgtt     960
tgcaagcagc agattacgcg cagaaaaaaa ggatctcaag aagatccttt gatcttttct    1020
acggggtctg acgctcagtg gaacgaaaac tcacgttaag ggattttggt catgagatta    1080
tcaaaaagga tcttcaccta gatccttttα aattaaaaat gaagttttaa atcaatctaa    1140
agtatatatg agtaaacttg gtctgacagt taccaatgct taatcagtga ggcacctatc    1200
tcagcgatct gtctatttcg ttcatccata gttgcctgac tcctgcaaac cacgttgtgg    1260
```

```
tagaattggt aaagagagtc gtgtaaaata tcgagttcgc acatcttgtt gtctgattat    1320
tgattttggg cgaaaccatt tgatcatatg acaagatgtg tatctacctt aacttaatga    1380
ttttgataaa aatcattagg taccccggct ctagatggca tgacattaac ctataaaaat    1440
aggcgtatca cgaggccctt tcgtctcgcg cgtttcggtg atgacggtga aaacctctga    1500
cacatgcagc tcccggagac ggtcacagct tgtctgtaag cggatgccgg gagcagacaa    1560
gcccgtcagg gcgcgtcagc gggtgttggc gggtgtcggg gctggcttaa ctatgcggca    1620
tcagagcaga ttgtactgag agtgcaccat atgcggtgtg aaataccgca cagatgcgta    1680
aggagaaaat accgcatcag attggctatt ggccattgca tacgttgtat ccatatcata    1740
atatgtacat ttatattggc tcatgtccaa cattaccgcc atgttgacat tgattattga    1800
ctagttatta atagtaatca attacggggt cattagttca tagcccatat atggagttcc    1860
gcgttacata acttacggta aatggcccgc ctggctgacc gcccaacgac ccccgcccat    1920
tgacgtcaat aatgacgtat gttcccatag taacgccaat agggactttc cattgacgtc    1980
aatgggtgga gtatttacgg taaactgccc acttggcagt acatcaagtg tatcatatgc    2040
caagtacgcc ccctattgac gtcaatgacg gtaaatggcc cgcctggcat tatgcccagt    2100
acatgacctt atgggacttt cctacttggc agtacatcta cgtattagtc atcgctatta    2160
ccatggtgat gcggttttgg cagtacatca atgggcgtgg atagcggttt gactcacggg    2220
gatttccaag tctccacccc attgacgtca atgggagttt gttttggcac caaaatcaac    2280
gggactttcc aaaatgtcgt aacaactccg ccccattgac gcaaatgggc ggtaggcgtg    2340
tacggtggga ggtctatata agcagagctc gtttagtgaa ccgtcagatc gcctggagac    2400
gccatccacg ctgttttgac ctccatagaa gacaccggga ccgatccagc ctccgcggct    2460
cgcatctctc cttcacgcgc ccgccgccct acctgaggcc gccatccacg ccggttgagt    2520
cgcgttctgc cgcctcccgc ctgtggtgcc tcctgaactg cgtccgccgt ctaggtaagt    2580
ttaaagctca ggtcgagacc gggcctttgt ccggcgctcc cttggagcct acctagactc    2640
agccggctct ccacgctttg cctgaccctg cttgctcaac tctagttctc tcgttaactt    2700
aatgagacag atagaaactg gtcttgtaga aacagagtag tcgcctgctt ttctgccagg    2760
tgctgacttc tctcccctgg gctttttttct ttttctcagg ttgaaaagaa gaagacgaag    2820
aagacgaaga agacaaaccg tcgtcgacat ggcgccccgc agcgcccggc gacccctgct    2880
gctgctactg ctgttgctgc tgctcggcct catgcattgt gcgtcagcag caatgtttat    2940
ggtgaaaaat ggcaacggga ccgcgtgcat aatggccaac ttctctgctg ccttctcagt    3000
gaactacgac accaagagtg gccctaagaa catgacccct gacctgccat cagatgccac    3060
agtggtgctc aaccgcagct cctgtggaaa agagaacact tctgaccca gtctcgtgat    3120
tgcttttgga agaggacata cactcactct caatttcacg agaaatgcaa cacgttacag    3180
cgttcagctc atgagttttg tttataactt gtcagacaca cacctttttcc ccaatgcgag    3240
ctccaaagaa atcaagactg tggaatctat aactgacatc agggcagata tagataaaaa    3300
atacagatgt gttagtggca cccaggtcca catgaacaac gtgaccgtaa cgctccatga    3360
tgccaccatc caggcgtacc tttccaacag cagcttcagc aggggagaga cacgctgtga    3420
acaagacagg ccttccccaa ccacagcgcc cctgcgcca cccagcccct cgccctcacc    3480
cgtgcccaag agccctctg tggacaagta caacgtgagc ggcaccaacg ggacctgcct    3540
gctggccagc atggggctgc agctgaacct cacctatgag aggaaggaca acacgacggt    3600
```

-continued

```
gacaaggctt ctcaacatca accccaacaa gacctcggcc agcgggagct gcggcgccca    3660
cctggtgact ctggagctgc acagcgaggg caccaccgtc ctgctcttcc agttcgggat    3720
gaatgcaagt tctagccggt ttttcctaca aggaatccag ttgaatacaa ttcttcctga    3780
cgccagagac cctgccttta agctgccaac cggctccctg cgagcgctgc aggccacagt    3840
cggcaattcc tacaagtgca acgcggagga gcacgtccgt gtcacgaagg cgttttcagt    3900
caatatattc aaagtgtggg tccaggcttt caaggtggaa ggtggccagt ttggctctgt    3960
ggaggagtgt ctgctggacg agaacagcct cgaggacaat cctattgatt cctgctggcg    4020
tggagattct aactgggcac agaaccggat gaaactggct gactgtgccg tgggctttgg    4080
ctcttccact atgggaggga agggaggcga cctgtacact gttacaaaca gcgacgacga    4140
ccctgtcaat ccagcacccg gaaccttgag atatggtgca acgcgagacc gaccactttg    4200
gatcatcttt agcggaaaca tgaacatcaa gttgaagatg cctatgtaca tagctgggta    4260
caaaaccttc gacggcagag agcccaagt gtacattggc aacggaggtc cctgcgtgtt    4320
catcaagcgt gttagtaatg tgatcattca cggtctgcac ctctatggct gttcaacaag    4380
cgtgctgggg aatgtgctga tcaatgagtc attcggtgtt gaacccgtgc acccacagga    4440
cggtgatgcg ttgacactga ggacagccac caatatctgg attgaccata acagtttctc    4500
taacagctca gatggcctgg tggatgtcac cttgagtagc acaggggtca caatcagcaa    4560
caatctgttc ttcaaccatc ataaggtgat gctgctgggc cacgacgatg cgtattccga    4620
cgataagagc atgaaagtga cggtggcctt taaccagttt ggtcctaact gtggacagcg    4680
gatgcctaga gccaggtacg gactggtgca cgtggccaac aacaactatg atccgtggac    4740
tatctatgca attggcggtt cttccaaccc gacgatactg agtgaaggga actccttact    4800
cgctcccaat gagagctaca agaagcaggt caccatccgc ataggctgca aaactagttc    4860
atcctgtagc aactgggtgt ggcagtccac tcaagatgtc ttctacaacg agcttacttt    4920
cgttagcagt gggaaatacg aaggtggcaa catatacaca aagaaagagg ctttcaatgt    4980
ggagaatggc aatgccactc cccagctcac caagaatgca ggggtgctca cctgctccct    5040
gagcaaacgg tgcgaattca cgctgatccc catcgctgtg ggtggtgccc tggcggggct    5100
ggtcctcatc gtcctcatcg cctacctcgt cggcaggaag aggagtcacg caggctacca    5160
gactatctag taaagatctt tttccctctg ccaaaaatta tggggacatc atgaagcccc    5220
ttgagcatct gacttctggc taataaagga aatttatttt cattgcaata gtgtgttgga    5280
atttttgtg tctctcactc ggaaggacat aagggcggcc gctagc              5326
```

<210> SEQ ID NO 5
<211> LENGTH: 773
<212> TYPE: PRT
<213> ORGANISM: Cryptomeria japonica

<400> SEQUENCE: 5

```
Met Ala Pro Arg Ser Ala Arg Arg Pro Leu Leu Leu Leu Leu Leu Leu
1               5                   10                  15

Leu Leu Leu Gly Leu Met His Cys Ala Ser Ala Ala Met Phe Met Val
            20                  25                  30

Lys Asn Gly Asn Gly Thr Ala Cys Ile Met Ala Asn Phe Ser Ala Ala
        35                  40                  45

Phe Ser Val Asn Tyr Asp Thr Lys Ser Gly Pro Lys Asn Met Thr Leu
    50                  55                  60

Asp Leu Pro Ser Asp Ala Thr Val Val Leu Asn Arg Ser Ser Cys Gly
```

```
                65                  70                  75                  80
        Lys Glu Asn Thr Ser Asp Pro Ser Leu Val Ile Ala Phe Gly Arg Gly
                            85                  90                  95

His Thr Leu Thr Leu Asn Phe Thr Arg Asn Ala Thr Arg Tyr Ser Val
                        100                 105                 110

Gln Leu Met Ser Phe Val Tyr Asn Leu Ser Asp Thr His Leu Phe Pro
                        115                 120                 125

Asn Ala Ser Ser Lys Glu Ile Lys Thr Val Glu Ser Ile Thr Asp Ile
                        130                 135                 140

Arg Ala Asp Ile Asp Lys Lys Tyr Arg Cys Val Ser Gly Thr Gln Val
        145                 150                 155                 160

His Met Asn Asn Val Thr Val Thr Leu His Asp Ala Thr Ile Gln Ala
                            165                 170                 175

Tyr Leu Ser Asn Ser Ser Phe Ser Arg Gly Glu Thr Arg Cys Glu Gln
                        180                 185                 190

Asp Arg Pro Ser Pro Thr Thr Ala Pro Pro Ala Pro Pro Ser Pro Ser
                        195                 200                 205

Pro Ser Pro Val Pro Lys Ser Pro Ser Val Asp Lys Tyr Asn Val Ser
                    210                 215                 220

Gly Thr Asn Gly Thr Cys Leu Leu Ala Ser Met Gly Leu Gln Leu Asn
        225                 230                 235                 240

Leu Thr Tyr Glu Arg Lys Asp Asn Thr Thr Val Thr Arg Leu Leu Asn
                            245                 250                 255

Ile Asn Pro Asn Lys Thr Ser Ala Ser Gly Ser Cys Gly Ala His Leu
                        260                 265                 270

Val Thr Leu Glu Leu His Ser Glu Gly Thr Thr Val Leu Leu Phe Gln
                    275                 280                 285

Phe Gly Met Asn Ala Ser Ser Ser Arg Phe Phe Leu Gln Gly Ile Gln
                        290                 295                 300

Leu Asn Thr Ile Leu Pro Asp Ala Arg Asp Pro Ala Phe Lys Ala Ala
        305                 310                 315                 320

Asn Gly Ser Leu Arg Ala Leu Gln Ala Thr Val Gly Asn Ser Tyr Lys
                            325                 330                 335

Cys Asn Ala Glu Glu His Val Arg Val Thr Lys Ala Phe Ser Val Asn
                        340                 345                 350

Ile Phe Lys Val Trp Val Gln Ala Phe Lys Val Glu Gly Gly Gln Phe
                        355                 360                 365

Gly Ser Val Glu Glu Cys Leu Leu Asp Glu Asn Ser Leu Glu Asp Asn
                    370                 375                 380

Pro Ile Asp Ser Cys Trp Arg Gly Asp Ser Asn Trp Ala Gln Asn Arg
        385                 390                 395                 400

Met Lys Leu Ala Asp Cys Ala Val Gly Phe Gly Ser Ser Thr Met Gly
                            405                 410                 415

Gly Lys Gly Gly Asp Leu Tyr Thr Val Thr Asn Ser Asp Asp Asp Pro
                        420                 425                 430

Val Asn Pro Ala Pro Gly Thr Leu Arg Tyr Gly Ala Thr Arg Asp Arg
                        435                 440                 445

Pro Leu Trp Ile Ile Phe Ser Gly Asn Met Asn Ile Lys Leu Lys Met
        450                 455                 460

Pro Met Tyr Ile Ala Gly Tyr Lys Thr Phe Asp Gly Arg Gly Ala Gln
                            465                 470                 475                 480

Val Tyr Ile Gly Asn Gly Gly Pro Cys Val Phe Ile Lys Arg Val Ser
                        485                 490                 495
```

```
Asn Val Ile Ile His Gly Leu His Leu Tyr Gly Cys Ser Thr Ser Val
            500                 505                 510

Leu Gly Asn Val Leu Ile Asn Glu Ser Phe Gly Val Glu Pro Val His
            515                 520                 525

Pro Gln Asp Gly Asp Ala Leu Thr Leu Arg Thr Ala Thr Asn Ile Trp
        530                 535                 540

Ile Asp His Asn Ser Phe Ser Asn Ser Ser Asp Gly Leu Val Asp Val
545                 550                 555                 560

Thr Leu Ser Ser Thr Gly Val Thr Ile Ser Asn Asn Leu Phe Phe Asn
                565                 570                 575

His His Lys Val Met Leu Leu Gly His Asp Asp Ala Tyr Ser Asp Asp
            580                 585                 590

Lys Ser Met Lys Val Thr Val Ala Phe Asn Gln Phe Gly Pro Asn Cys
            595                 600                 605

Gly Gln Arg Met Pro Arg Ala Arg Tyr Gly Leu Val His Val Ala Asn
            610                 615                 620

Asn Asn Tyr Asp Pro Trp Thr Ile Tyr Ala Ile Gly Gly Ser Ser Asn
625                 630                 635                 640

Pro Thr Ile Leu Ser Glu Gly Asn Ser Phe Thr Ala Pro Asn Glu Ser
                645                 650                 655

Tyr Lys Lys Gln Val Thr Ile Arg Ile Gly Cys Lys Thr Ser Ser Ser
            660                 665                 670

Cys Ser Asn Trp Val Trp Gln Ser Thr Gln Asp Val Phe Tyr Asn Gly
            675                 680                 685

Ala Tyr Phe Val Ser Ser Gly Lys Tyr Glu Gly Gly Asn Ile Tyr Thr
        690                 695                 700

Lys Lys Glu Ala Phe Asn Val Glu Asn Gly Asn Ala Thr Pro Gln Leu
705                 710                 715                 720

Thr Lys Asn Ala Gly Val Leu Thr Cys Ser Leu Ser Lys Arg Cys Glu
                725                 730                 735

Phe Thr Leu Ile Pro Ile Ala Val Gly Gly Ala Leu Ala Gly Leu Val
            740                 745                 750

Leu Ile Val Leu Ile Ala Tyr Leu Val Gly Arg Lys Arg Ser His Ala
            755                 760                 765

Gly Tyr Gln Thr Ile
    770

<210> SEQ ID NO 6
<211> LENGTH: 6817
<212> TYPE: DNA
<213> ORGANISM: Artificial Sequence
<220> FEATURE:
<223> OTHER INFORMATION: Description of Artificial Sequence: Synthetic
      Cry J1&J2-LAMP polynucleotide

<400> SEQUENCE: 6
ccgcctaatg agcgggcttt ttttcttag ggtgcaaaag gagagcctgt aagcgggcac      60
tcttccgtgg tctggtggat aaattcgcaa gggtatcatg gcggacgacc ggggttcgag    120
ccccgtatcc ggccgtccgc cgtgatccat gcggttaccg cccgcgtgtc gaacccaggt    180
gtgcgacgtc agacaacggg ggagtgctcc ttttggcttc cttcccttc ttccgcttcc     240 tcgctcactg actcgctgcg ctcggtcgtt cggctgcggc gagcggtatc agctcactca    300
aaggcggtaa tacggttatc cacagaatca ggggataacg caggaaagaa catgtgagca    360
aaaggccagc aaaaggccag gaaccgtaaa aaggccgcgt tgctggcgtt tttccatagg    420
```

```
ctccgccccc ctgacgagca tcacaaaaat cgacgctcaa gtcagaggtg gcgaaacccg      480
acaggactat aaagatacca ggcgtttccc cctggaagct ccctcgtgcg ctctcctgtt      540
ccgaccctgc cgcttaccgg atacctgtcc gcctttctcc cttcgggaag cgtggcgctt      600
tctcatagct cacgctgtag gtatctcagt tcggtgtagg tcgttcgctc caagctgggc      660
tgtgtgcacg aacccccgt tcagcccgac cgctgcgcct tatccggtaa ctatcgtctt      720
gagtccaacc cggtaagaca cgacttatcg ccactggcag cagccactgg taacaggatt      780
agcagagcga ggtatgtagg cggtgctaca gagttcttga agtggtggcc taactacggc      840
tacactagaa gaacagtatt tggtatctgc gctctgctga agccagttac cttcggaaaa      900
agagttggta gctcttgatc cggcaaacaa accaccgctg gtagcggtgg ttttttttgtt      960 tgcaagcagc agattacgcg cagaaaaaaa ggatctcaag aagatccttt gatcttttct     1020
acggggtctg acgctcagtg gaacgaaaac tcacgttaag ggattttggt catgagatta     1080
tcaaaaagga tcttcaccta gatccttta aattaaaaat gaagttttaa atcaatctaa     1140
agtatatatg agtaaacttg gtctgacagt taccaatgct taatcagtga ggcacctatc     1200
tcagcgatct gtctatttcg ttcatccata gttgcctgac tcctgcaaac cacgttgtgg     1260
tagaattggt aaagagagtc gtgtaaaata tcgagttcgc acatcttgtt gtctgattat     1320 tgattttttgg cgaaaccatt tgatcatatg acaagatgtg tatctacctt aacttaatga     1380
ttttgataaa aatcattagg taccccggct ctagatggca tgacattaac ctataaaaat     1440
aggcgtatca cgaggccctt tcgtctcgcg cgtttcggtg atgacggtga aaacctctga     1500
cacatgcagc tcccggagac ggtcacagct tgtctgtaag cggatgccgg gagcagacaa     1560
gcccgtcagg gcgcgtcagc gggtgttggc gggtgtcggg gctggcttaa ctatgcggca     1620
tcagagcaga ttgtactgag agtgcaccat atgcggtgtg aaataccgca cagatgcgta     1680 aggagaaaaat accgcatcag attggctatt ggccattgca tacgttgtat ccatatcata     1740
atatgtacat ttatattggc tcatgtccaa cattaccgcc atgttgacat tgattattga     1800
ctagttatta atagtaatca attacggggt cattagttca tagcccatat atggagttcc     1860
gcgttacata acttacggta aatggcccgc ctggctgacc gcccaacgac ccccgcccat     1920
tgacgtcaat aatgacgtat gttcccatag taacgccaat agggactttc cattgacgtc     1980
aatgggtgga gtatttacgg taaactgccc acttggcagt acatcaagtg tatcatatgc     2040
caagtacgcc ccctattgac gtcaatgacg gtaaatggcc cgcctggcat tatgcccagt     2100
acatgacctt atgggacttt cctacttggc agtacatcta cgtattagtc atcgctatta     2160
ccatggtgat gcggttttgg cagtacatca atgggcgtgg atagcggttt gactcacggg     2220
gatttccaag tctccacccc attgacgtca atgggagttt gttttggcac caaaatcaac     2280
gggactttcc aaaatgtcgt aacaactccg ccccattgac gcaaatgggc ggtaggcgtg     2340
tacggtggga ggtctatata agcagagctc gtttagtgaa ccgtcagatc gcctggagac     2400
gccatccacg ctgttttgac ctccatagaa gacaccggga ccgatccagc ctccgcggct     2460
cgcatctctc cttcacgcgc ccgccgccct acctgaggcc gccatccacg ccggttgagt     2520
cgcgttctgc cgcctcccgc ctgtggtgcc tcctgaactg cgtccgccgt ctaggtaagt     2580
ttaaagctca ggtcgagacc gggcctttgt ccggcgctcc cttggagcct acctagactc     2640
agccggctct ccacgctttg cctgaccctg cttgctcaac tctagttctc tcgttaactt     2700
aatgagacag atagaaactg gtcttgtaga aacagagtag tcgcctgctt ttctgccagg     2760
```

```
tgctgacttc tctcccctgg gctttttcct ttttctcagg ttgaaaagaa gaagacgaag    2820
aagacgaaga agacaaaccg tcgtcgacat ggcgccccgc agcgcccggc gacccctgct    2880
gctgctactg ctgttgctgc tgctcggcct catgcattgt gcgtcagcag caatgtttat    2940
ggtgaaaaat ggcaacggga ccgcgtgcat aatggccaac ttctctgctg ccttctcagt    3000
gaactacgac accaagagtg ccctaagaa catgacccttg acctgccat cagatgccac    3060 agtggtgctc aaccgcagct cctgtggaaa agagaacact tctgacccca gtctcgtgat    3120
tgcttttgga agaggacata cactcactct caatttcacg agaaatgcaa cacgttacag    3180
cgtccagctc atgagttttg tttataactt gtcagacaca cacctttttcc ccaatgcgag    3240 ctccaaagaa atcaagactg tggaatctat aactgacatc agggcagata tagataaaaa    3300
atacagatgt gttagtggca cccaggtcca catgaacaac gtgaccgtaa cgctccatga    3360
tgccaccatc caggcgtacc tttccaacag cagcttcagc cggggagaga cacgctgtga    3420
acaagacagg ccttcccaa ccacagcgcc cctgcgcca cccagccct cgccctcacc    3480 cgtgcccaag agccctctg tggacaagta caacgtgagc ggcaccaacg ggacctgcct    3540
gctggccagc atgggctgc agctgaacct cacctatgag aggaaggaca acacgacggt    3600
gacaaggctt ctcaacatca accccaacaa gacctcggcc agcgggagct gcggcgccca    3660
cctggtgact ctggagctgc acagcgaggg caccaccgtc ctgctcttcc agttcgggat    3720
gaatgcaagt tctagccggt ttttcctaca aggaatccag ttgaatacaa ttcttcctga    3780
cgccagagac cctgccttta aagctgccaa cggctccctg cgagcgctgc aggccacagt    3840
cggcaattcc tacaagtgca acgcggagga gcacgtccgt gtcacgaagg cgttttcagt    3900
caatatattc aaagtgtggg tccaggcttt caaggtggaa ggtggccagt ttggctctgt    3960
ggaggagtgt ctgctggacg agaacagcct cgaggacaat cctattgatt cctgctggcg    4020
tggagattct aactgggcac agaaccggat gaaactggct gactgtgccg tgggctttgg    4080
ctcttccact atgggaggga agggaggcga cctgtacact gttacaaaca gcgacgacga    4140
ccctgtcaat ccagcacccg gaaccttgag atatggtgca acgcgagacc gaccactttg    4200 gatcatctttt agcggaaaca tgaacatcaa gttgaagatg cctatgtaca tagctgggta    4260
caaaaccttc gacggcagag gagcccaagt gtacattggc aacggaggtc cctgcgtgtt    4320
catcaagcgt gttagtaatg tgatcattca cggtctgcac ctctatggct gttcaacaag    4380
cgtgctgggg aatgtgctga tcaatgagtc attcggtgtt gaacccgtgc acccacagga    4440
cggtgatgcg ttgacactga ggacagccac caatatctgg attgaccata acagtttctc    4500
taacagctca gatggcctgg tggatgtcac cttgagtagc acaggggtca caatcagcaa    4560
caatctgttc ttcaaccatc ataaggtgat gctgctgggc cacgacgatg cgtattccga    4620
cgataagagc atgaaagtga cggtggcctt taaccagttt ggtcctaact gtggacagcg    4680
gatgcctaga gccaggtacg gactggtgca cgtggccaac aacaactatg atccgtggac    4740
tatctatgca attggcggtt cttccaaccc gacgatactg agtgaaggga actcctttac    4800
cgctcccaat gagagctaca gaagcaggt caccatccgc ataggctgca aaactagttc    4860
atcctgtagc aactgggtgt ggcagtccac tcaagatgtc ttctacaacg gagcttactt    4920
cgttagcagt gggaaatacg aaggtggcaa catatacaca aagaaagagg ctttcaatgt    4980
ggagaatggc aatgccactc cccagctcac caagaatgca ggggtgctca cctgctccct    5040
gagcaaacgg tgcggcggtg gtggcctcga ggatcagtca gcgcagatca tgctggatag    5100
cgtggtggag aagtacctga ggagtaacag gtcactgcgc aaggttgagc attccagaca    5160
```

-continued

```
cgacgctatc aacatcttca acgtggagaa gtacggtgct gtcggagacg ggaagcacga  5220
ctgcaccgaa gccttttcta cagcctggca agctgcctgc aagaatccct cagccatgct  5280
cctcgtgcct gggtctaaga agtttgtcgt gaataacctt ttcttcaatg accctgcca   5340
gccacacttt accttcaaag ttgatgggat catcgcagcc tatcagaacc cagctagctg  5400
gaagaacaat cggatctggt tgcagtttgc caaactgaca ggattcaccc tgatggggaa  5460
aggcgtgatc gacggacagg gcaaacagtg gtgggcaggg cagtgcaagt gggtcaatgg  5520
tagggagatt tgcaatgaca gggaccgtcc taccgctatc aagtttgatt tcagcacagg  5580
actgattatt caggggttga agctgatgaa tagtccagag tttcaccttg tgtttggcaa  5640
ttgtgaaggt gtgaagatca taggcattag cattacagca cctcgcgatt ctcccaatac  5700
ggacggcatt gacatcttcg cctccaagaa ctttcacctg caaaagaata ccattggcac  5760
aggcgacgac tgcgtggcca ttggcactgg cagcagcaat atcgttatcg aagatttgat  5820
atgtggtcct gggcatggca taagcattgg aagcctgggt agagaaaact caagagctga  5880
agtcagctat gttcacgtta acggagcgaa gttcattgat acccagaacg gactgcgaat  5940
caaaacttgg caaggggggaa gtggcatggc atctcacatc atctacgaga acgtcgagat  6000
gatcaattcc gagaaccccca tactgattaa ccaattctat tgtacttccg cctctgcctg  6060
ccagaatcag agatcagccg tgcagattca ggacgtgaca tacaagaata tccgagggac  6120
gagcgctacc gctgccgcaa tacagctcaa atgttccgat agcatgccct gcaaagatat  6180
caagcttagt gatatctccc tcaaactgac tagcggaaag atagcgtcct gtctcaatga  6240
taacgcaaat ggctacttct cagggcatgt gatccctgca tgcaaaaacc ttagcccgag  6300
tgcgaaacgc aaagaatcca aatcccataa gcatccgaag actgtgatgg tcgagaacat  6360
gagagcctac gacaaaggga accggacgag gattctgctg ggctctcgac cgccaaactg  6420
taccaacaaa tgtcacggtt gttctccatg caaagctaaa ctggtgatag tgcatcgcat  6480
catgcctcaa gagtactatc cccagcgttg gatttgtagt tgccatggca agatctatca  6540
cccagaattc acgctgatcc ccatcgctgt gggtggtgcc ctggcggggc tggtcctcat  6600
cgtcctcatc gcctacctcg tcggcaggaa gaggagtcac gcaggctacc agactatcta  6660
gtaaggatct ttttcccctct gccaaaaatt atggggacat catgaagccc cttgagcatc  6720
tgacttctgg ctaataaagg aaatttattt tcattgcaat agtgtgttgg aattttttgt  6780
gtctctcact cggaaggaca taagggcggc cgctagc                          6817
```

<210> SEQ ID NO 7  
<211> LENGTH: 1270  
<212> TYPE: PRT  
<213> ORGANISM: Artificial Sequence  
<220> FEATURE:  
<223> OTHER INFORMATION: Description of Artificial Sequence: Synthetic chimeric polypeptide of Cry J1 and CryJ2 allergens of c. japonica

<400> SEQUENCE: 7

```
Met Ala Pro Arg Ser Ala Arg Arg Pro Leu Leu Leu Leu Leu Leu
1               5                   10                  15

Leu Leu Leu Gly Leu Met His Cys Ala Ser Ala Ala Met Phe Met Val
                20                  25                  30

Lys Asn Gly Asn Gly Thr Ala Cys Ile Met Ala Asn Phe Ser Ala Ala
            35                  40                  45

Phe Ser Val Asn Tyr Asp Thr Lys Ser Gly Pro Lys Asn Met Thr Leu
```

```
                50                  55                  60
Asp Leu Pro Ser Asp Ala Thr Val Val Leu Asn Arg Ser Ser Cys Gly
 65                  70                  75                  80

Lys Glu Asn Thr Ser Asp Pro Ser Leu Val Ile Ala Phe Gly Arg Gly
                 85                  90                  95

His Thr Leu Thr Leu Asn Phe Thr Arg Asn Ala Thr Arg Tyr Ser Val
            100                 105                 110

Gln Leu Met Ser Phe Val Tyr Asn Leu Ser Asp Thr His Leu Phe Pro
            115                 120                 125

Asn Ala Ser Ser Lys Glu Ile Lys Thr Val Glu Ser Ile Thr Asp Ile
130                 135                 140

Arg Ala Asp Ile Asp Lys Lys Tyr Arg Cys Val Ser Gly Thr Gln Val
145                 150                 155                 160

His Met Asn Asn Val Thr Val Thr Leu His Asp Ala Thr Ile Gln Ala
                165                 170                 175

Tyr Leu Ser Asn Ser Ser Phe Ser Arg Gly Glu Thr Arg Cys Glu Gln
            180                 185                 190

Asp Arg Pro Ser Pro Thr Thr Ala Pro Pro Ala Pro Pro Ser Pro Ser
            195                 200                 205

Pro Ser Pro Val Pro Lys Ser Pro Ser Val Asp Lys Tyr Asn Val Ser
210                 215                 220

Gly Thr Asn Gly Thr Cys Leu Leu Ala Ser Met Gly Leu Gln Leu Asn
225                 230                 235                 240

Leu Thr Tyr Glu Arg Lys Asp Asn Thr Val Thr Arg Leu Leu Asn
                245                 250                 255

Ile Asn Pro Asn Lys Thr Ser Ala Ser Gly Ser Cys Gly Ala His Leu
                260                 265                 270

Val Thr Leu Glu Leu His Ser Gly Thr Thr Val Leu Leu Phe Gln
            275                 280                 285

Phe Gly Met Asn Ala Ser Ser Ser Arg Phe Phe Leu Gln Gly Ile Gln
            290                 295                 300

Leu Asn Thr Ile Leu Pro Asp Ala Arg Asp Pro Ala Phe Lys Ala Ala
305                 310                 315                 320

Asn Gly Ser Leu Arg Ala Leu Gln Ala Thr Val Gly Asn Ser Tyr Lys
                325                 330                 335

Cys Asn Ala Glu Glu His Val Arg Val Thr Lys Ala Phe Ser Val Asn
            340                 345                 350

Ile Phe Lys Val Trp Val Gln Ala Phe Lys Val Glu Gly Gly Gln Phe
            355                 360                 365

Gly Ser Val Glu Glu Cys Leu Leu Asp Glu Asn Ser Leu Glu Asp Asn
370                 375                 380

Pro Ile Asp Ser Cys Trp Arg Gly Asp Ser Asn Trp Ala Gln Asn Arg
385                 390                 395                 400

Met Lys Leu Ala Asp Cys Ala Val Gly Phe Gly Ser Ser Thr Met Gly
                405                 410                 415

Gly Lys Gly Gly Asp Leu Tyr Thr Val Thr Asn Ser Asp Asp Pro
            420                 425                 430

Val Asn Pro Ala Pro Gly Thr Leu Arg Tyr Gly Ala Thr Arg Asp Arg
            435                 440                 445

Pro Leu Trp Ile Ile Phe Ser Gly Asn Met Asn Ile Lys Leu Lys Met
450                 455                 460

Pro Met Tyr Ile Ala Gly Tyr Lys Thr Phe Asp Gly Arg Gly Ala Gln
465                 470                 475                 480
```

-continued

Val Tyr Ile Gly Asn Gly Gly Pro Cys Val Phe Ile Lys Arg Val Ser
            485                 490                 495

Asn Val Ile Ile His Gly Leu His Leu Tyr Gly Cys Ser Thr Ser Val
        500                 505                 510

Leu Gly Asn Val Leu Ile Asn Glu Ser Phe Gly Val Glu Pro Val His
    515                 520                 525

Pro Gln Asp Gly Asp Ala Leu Thr Leu Arg Thr Ala Thr Asn Ile Trp
530                 535                 540

Ile Asp His Asn Ser Phe Ser Asn Ser Ser Asp Gly Leu Val Asp Val
545                 550                 555                 560

Thr Leu Ser Ser Thr Gly Val Thr Ile Ser Asn Asn Leu Phe Phe Asn
                565                 570                 575

His His Lys Val Met Leu Leu Gly His Asp Asp Ala Tyr Ser Asp Asp
            580                 585                 590

Lys Ser Met Lys Val Thr Val Ala Phe Asn Gln Phe Gly Pro Asn Cys
        595                 600                 605

Gly Gln Arg Met Pro Arg Ala Arg Tyr Gly Leu Val His Val Ala Asn
    610                 615                 620

Asn Asn Tyr Asp Pro Trp Thr Ile Tyr Ala Ile Gly Ser Ser Asn
625                 630                 635                 640

Pro Thr Ile Leu Ser Glu Gly Asn Ser Phe Thr Ala Pro Asn Glu Ser
                645                 650                 655

Tyr Lys Lys Gln Val Thr Ile Arg Ile Gly Cys Lys Thr Ser Ser Ser
            660                 665                 670

Cys Ser Asn Trp Val Trp Gln Ser Thr Gln Asp Val Phe Tyr Asn Gly
        675                 680                 685

Ala Tyr Phe Val Ser Ser Gly Lys Tyr Glu Gly Asn Ile Tyr Thr
    690                 695                 700

Lys Lys Glu Ala Phe Asn Val Glu Asn Gly Asn Ala Thr Pro Gln Leu
705                 710                 715                 720

Thr Lys Asn Ala Gly Val Leu Thr Cys Ser Leu Ser Lys Arg Cys Gly
                725                 730                 735

Gly Gly Gly Leu Glu Asp Gln Ser Ala Gln Ile Met Leu Asp Ser Val
            740                 745                 750

Val Glu Lys Tyr Leu Arg Ser Asn Arg Ser Leu Arg Lys Val Glu His
        755                 760                 765

Ser Arg His Asp Ala Ile Asn Ile Phe Asn Val Glu Lys Tyr Gly Ala
    770                 775                 780

Val Gly Asp Gly Lys His Asp Cys Thr Glu Ala Phe Ser Thr Ala Trp
785                 790                 795                 800

Gln Ala Ala Cys Lys Asn Pro Ser Ala Met Leu Leu Val Pro Gly Ser
                805                 810                 815

Lys Lys Phe Val Val Asn Asn Leu Phe Phe Asn Gly Pro Cys Gln Pro
            820                 825                 830

His Phe Thr Phe Lys Val Asp Gly Ile Ile Ala Ala Tyr Gln Asn Pro
        835                 840                 845

Ala Ser Trp Lys Asn Asn Arg Ile Trp Leu Gln Phe Ala Lys Leu Thr
    850                 855                 860

Gly Phe Thr Leu Met Gly Lys Gly Val Ile Asp Gly Gln Gly Lys Gln
865                 870                 875                 880

Trp Trp Ala Gly Gln Cys Lys Trp Val Asn Gly Arg Glu Ile Cys Asn
                885                 890                 895

```
Asp Arg Asp Arg Pro Thr Ala Ile Lys Phe Asp Phe Ser Thr Gly Leu
            900                 905                 910

Ile Ile Gln Gly Leu Lys Leu Met Asn Ser Pro Glu Phe His Leu Val
        915                 920                 925

Phe Gly Asn Cys Glu Gly Val Lys Ile Ile Gly Ile Ser Ile Thr Ala
        930                 935                 940

Pro Arg Asp Ser Pro Asn Thr Asp Gly Ile Asp Ile Phe Ala Ser Lys
945                 950                 955                 960

Asn Phe His Leu Gln Lys Asn Thr Ile Gly Thr Gly Asp Asp Cys Val
                965                 970                 975

Ala Ile Gly Thr Gly Ser Ser Asn Ile Val Ile Glu Asp Leu Ile Cys
            980                 985                 990

Gly Pro Gly His Gly Ile Ser Ile Gly Ser Leu Gly Arg Glu Asn Ser
        995                 1000                1005

Arg Ala Glu Val Ser Tyr Val His Val Asn Gly Ala Lys Phe Ile
    1010                1015                1020

Asp Thr Gln Asn Gly Leu Arg Ile Lys Thr Trp Gln Gly Gly Ser
    1025                1030                1035

Gly Met Ala Ser His Ile Ile Tyr Glu Asn Val Glu Met Ile Asn
    1040                1045                1050

Ser Glu Asn Pro Ile Leu Ile Asn Gln Phe Tyr Cys Thr Ser Ala
    1055                1060                1065

Ser Ala Cys Gln Asn Gln Arg Ser Ala Val Gln Ile Gln Asp Val
    1070                1075                1080

Thr Tyr Lys Asn Ile Arg Gly Thr Ser Ala Thr Ala Ala Ala Ile
    1085                1090                1095

Gln Leu Lys Cys Ser Asp Ser Met Pro Cys Lys Asp Ile Lys Leu
    1100                1105                1110

Ser Asp Ile Ser Leu Lys Leu Thr Ser Gly Lys Ile Ala Ser Cys
    1115                1120                1125

Leu Asn Asp Asn Ala Asn Gly Tyr Phe Ser Gly His Val Ile Pro
    1130                1135                1140

Ala Cys Lys Asn Leu Ser Pro Ser Ala Lys Arg Lys Glu Ser Lys
    1145                1150                1155

Ser His Lys His Pro Lys Thr Val Met Val Glu Asn Met Arg Ala
    1160                1165                1170

Tyr Asp Lys Gly Asn Arg Thr Arg Ile Leu Leu Gly Ser Arg Pro
    1175                1180                1185

Pro Asn Cys Thr Asn Lys Cys His Gly Cys Ser Pro Cys Lys Ala
    1190                1195                1200

Lys Leu Val Ile Val His Arg Ile Met Pro Gln Glu Tyr Tyr Pro
    1205                1210                1215

Gln Arg Trp Ile Cys Ser Cys His Gly Lys Ile Tyr His Pro Glu
    1220                1225                1230

Phe Thr Leu Ile Pro Ile Ala Val Gly Gly Ala Leu Ala Gly Leu
    1235                1240                1245

Val Leu Ile Val Leu Ile Ala Tyr Leu Val Gly Arg Lys Arg Ser
    1250                1255                1260

His Ala Gly Tyr Gln Thr Ile
    1265                1270

<210> SEQ ID NO 8
<211> LENGTH: 8023
<212> TYPE: DNA
```

<213> ORGANISM: Artificial Sequence
<220> FEATURE:
<223> OTHER INFORMATION: Description of Artificial Sequence: Synthetic polynucleotide coding region for the Ara H1/H2/H3 polyprotein

<400> SEQUENCE: 8

```
ccgcctaatg agcgggcttt ttttctttag

```
ccatggtgat gcggttttgg cagtacatca atgggcgtgg atagcggttt gactcacggg    2220
gatttccaag tctccacccc attgacgtca atgggagttt gttttggcac caaaatcaac    2280
gggactttcc aaaatgtcgt aacaactccg ccccattgac gcaaatgggc ggtaggcgtg    2340
tacggtggga ggtctatata agcagagctc gtttagtgaa ccgtcagatc gcctggagac    2400
gccatccacg ctgttttgac ctccatagaa gacaccggga ccgatccagc ctccgcggct    2460
cgcatctctc cttcacgcgc ccgccgccct acctgaggcc gccatccacg ccggttgagt    2520
cgcgttctgc cgcctcccgc ctgtggtgcc tcctgaactg cgtccgccgt ctaggtaagt    2580
ttaaagctca ggtcgagacc gggcctttgt ccggcgctcc cttggagcct acctagactc    2640
agccggctct ccacgctttg cctgaccctg cttgctcaac tctagttctc tcgttaactt    2700
aatgagacag atagaaactg gtcttgtaga aacagagtag tcgcctgctt ttctgccagg    2760
tgctgacttc tctcccctgg gctttttctt ttttctcagg ttgaaaagaa gaagacgaag    2820
aagacgaaga agacaaaccg tcgtcgacat ggcgccccgc agcgcccggc gaccctgct     2880 gctgctactg ctgttgctgc tgctcggcct catgcattgt gcgtcagcag caatgtttat    2940
ggtgaaaaat ggcaacggga ccgcgtgcat aatggccaac ttctctgctg ccttctcagt    3000
gaactacgac accaagagtg gccctaagaa catgacccctt gacctgccat cagatgccac    3060
agtggtgctc aaccgcagct cctgtgggaaa agagaacact tctgacccca gtctcgtgat    3120
tgcttttgga gaggacata cactcactct caatttcacg agaaatgcaa cacgttacag    3180
cgttcagctc atgagttttg tttataactt gtcagacaca cacctttttcc ccaatgcgag    3240 ctccaaagaa atcaagactg tggaatctat aactgacatc agggcagata tagataaaaa    3300
atacagatgt gttagtggca cccaggtcca catgaacaac gtgaccgtaa cgctccatga    3360
tgccaccatc caggcgtacc tttccaacag cagcttcagc aggggagaga cacgctgtga    3420
acaagacagg ccttccccaa ccacagcgcc ctgcgcca cccagcccct cgccctcacc      3480
cgtgcccaag agccctctg tggacaagta caacgtgagc ggcaccaacg ggacctgcct    3540
gctggccagc atggggctgc agctgaacct cacctatgag aggaaggaca acacgacggt    3600
gacaaggctt ctcaacatca cccccaacaa gacctcggcc agcgggagct gcggcgccca    3660
cctggtgact ctggagctgc acagcgaggg caccaccgtc ctgctcttcc agttcgggat    3720
gaatgcaagt tctagccggt ttttcctaca aggaatccag ttgaatacaa ttcttcctga    3780
cgccagagac cctgccttta aagctgccaa cggctccctg cgagcgctgc aggccacagt    3840
cggcaattcc tacaagtgca acgcggagga gcacgtccgt gtcacgaagg cgttttcagt    3900
caatatattc aaagtgtggg tccaggcttt caaggtggaa ggtggccagt ttggctctgt    3960
ggaggagtgt ctgctggacg agaacagcct cgagaagtcc agcccctacc agaagaaaac    4020
cgagaacccc tgcgcccagc ggtgcctgca gtcttgtcag caggaacccg acgacctgaa    4080
gcagaaggcc tgcgagagcc ggtgcaccaa gctggaatac gacccagat gcgtgtacga    4140 ccctagaggc cacaccggca ccaccaacca gagaagccct ccaggcgagc ggaccagagg    4200
cagacagcct ggcgactacg acgacgacag acggcagccc agaagagaag agggcggcag    4260
atggggacct gccggcccta gagagagaga acgcgaggaa gattggagac agcccagaga    4320
ggactggcgg aggccttctc accagcagcc ccggaagatc agacccgagg gcagagaagg    4380
cgagcaggaa tggggcacac ctggctctca cgtgcgcgag gaaaccagcc ggaacaaccc    4440
cttctacttc ccctcccggc ggttcagcac cagatacggc aaccgaaacg gccggatcag    4500
agtgctgcag agattcgacc agcggagccg gcagttccag aacctgcaga accaccggat    4560
```

```
cgtgcagatc gaggccaagc ccaacaccct ggtgctgccc aaacacgccg acgccgacaa      4620
catcctcgtg atccagcagg gccaggccac cgtgacagtg ccaacggca acaacagaaa       4680 gagcttcaac ctggacgagg ccacgccct gagaatcccc agcggcttca tcagctacat       4740
cctgaacaga cacgacaatc agaacctgag ggtggccaag atcagcatgc ccgtgaacac      4800
ccctggccag ttcgaggact tcttccccgc atcctcccgg gaccagagca gctacctgca      4860
gggcttcagc cggaataccc tggaagccgc cttcaacgcc gagttcaacg agatcagacg      4920
ggtgctgctg aagagaacg ctggcggaga gcaggaagaa cggggccaga gaagatggtc       4980
caccagaagc agcgagaaca acgagggcgt gatcgtgaag gtgtccaaag aacacgtgga      5040
agaactgacc aagcacgcca gagcgtgtc caagaagggc tccgaggaag aggggacat       5100 caccaacccc atcaatctga gagagggcga gcccgacctg agcaacaact tcggcaagct      5160
gttcgaagtg aagcccgaca agaagaaccc ccagctgcag gacctggaca tgatgctgac      5220
ctgcgtggaa atcaaagagg gggccctgat gctgccacac ttcaactcca aagccatggt      5280
catcgtggtc gtgaacaagg gcaccggcaa cctggaactg gtggccgtgc ggaaagagca      5340
gcagcagaga ggccgcagag aggaagaaga ggacgaggac gaagaagaag agggatccaa      5400
ccgggaagtg cggcggtaca ccgccagact gaaagaaggc gacgtgttca tcatgcctgc      5460
cgcccacccc gtggccatca atgcctctag cgagctgcat ctgctgggct tcggcattaa      5520
cgccgagaac aatcaccgga tctttctggc cggcgacaaa gacaacgtga tcgaccagat      5580
cgagaagcag gccaaggacc tggccttcc cggctctggc gaacaagtgg aaaagctgat      5640
caagaaccag aaagaaagcc acttcgtgtc cgccagaccc cagagccagt ctcagagccc      5700
tagctccccc gagaaagagt ctcctgagaa gaggaccag gaagaggaaa accagggcgg      5760
caagggccct ctgctgagca tcctgaaggc cttcaatggc ggcggaggca ggcagcagtg      5820
ggaactgcag ggcgacagaa gatgccagtc ccagctggaa cgggccaacc tgaggccttg      5880
cgagcagcac ctgatgcaga aaatccagcg cgacgaggac agctacggcc gggatcctta      5940
cagccccagc caggaccctt actcccctag ccaggatccc acagaagggg acccctacag      6000
ccctagcccc tacgatagaa gaggcgccgg aagcagccag caccaggaaa gatgctgcaa      6060
cgagctgaac gagtttgaga acaaccagcg ctgcatgtgc gaggccctgc agcagatcat      6120
ggaaaatcag agcgaccggc tgcagggacg gcagcaggaa cagcagttca agagagagct      6180
gcggaacctg cccagcagtg tggactgag agccccccag agatgcgacc tggaagtgga      6240
aagcggcggc agagatcggt acggcggagg gggcgtgacc ttcagacagg cggagaaga      6300 gaatgagtgc cagtttcagc ggctgaacgc ccagaggccc gacaacagaa tcgagagcga      6360
gggcggctac atcgagacat ggaaccccaa caaccaggaa tttcagtgcg ctgggggtggc      6420 cctgagcagg accgtgctga aagaaatgc cctgaggcgg cccttctaca gcaacgcccc      6480
cctgaaaatc tacgtgcagc agggcagcgg ctacttcggc ctgatctttc ccggatgccc      6540
ctccacctat gaggaacccg ctcaggaagg cagacggtat cagagccaga agcctagcag      6600
acggttccaa gtgggccagg acgatccag ccaacagcag caggactctc accagaaggt      6660
gcaccgcttc gacgagggcg acctgatcgc tgtgccaacc ggcgtggcct tctggatgta      6720
caacgacgag gataccgacg tcgtgaccgt gaccctgagc gacaccagct ccatccacaa      6780
ccagctggac cagttcccca gcggttttta cctggccggc aatcaggaac aggaatttct      6840
gagataccag cagcagcagg gctccagacc ccactacaga cagatcagcc ctagagtgcg      6900
```

```
gggcgacgaa caggaaaatg agggcagcaa catcttctcc ggctttgccc aggaatttct    6960
gcagcacgcc ttccaggtgg accggcagac cgtggaaaac ctgagaggcg agaacgagag    7020
agaggaacag ggcgccatcg tgactgtgaa gggcggcctg aggatcctga gccccgacga    7080
agaggatgag tcctctagaa gccccccaa ccgccgggaa gagttcgatg aggaccgcag     7140
cagacctcag cagcggggga agtacgacga gaacaggcgg ggctacaaga acggcatcga    7200
ggaaacaatc tgcagcgcca gcgtgaagaa gaatctgggc cggtccagca accccgacat    7260
ctacaatcca caggccggca gcctgcggag cgtgaacgaa ctggatctgc ccatcctggg    7320
atggctgggc ctgtctgccc agcacggcac catctaccgg aacgccatgt tcgtgcctca    7380
ctacaccctg aatgcccaca ccatcgtggt ggctctgaac ggccgcgccc acgtccaagt    7440
ggtggacagc aacggcaatc gggtgtacga tgaagaactg caggaaggac acgtcctggt    7500
ggtgccccag aattttgccg tggccgccaa ggcccagtcc gagaactatg agtatctggc    7560
cttcaagacc gacagccggc cctctatcgc caatcaagcc ggcgagaaca gcatcatcga    7620
caacctgccc gaggaagtgg tggccaacag ctaccggctg cctagagagc aggcccggca    7680
gctgaagaac aacaacccct tcaagttctt cgtgcccca ttcgaccacc agagcatgag     7740
agaggtggcc gaattcacgc tgatccccat cgctgtgggt ggtgccctgg cggggctggt    7800
cctcatcgtc ctcatcgcct acctcgtcgg caggaagagg agtcacgcag gctaccagac    7860
tatctagtaa ggatcttttt ccctctgcca aaaattatgg ggacatcatg aagccccttg    7920
agcatctgac ttctggctaa taaaggaaat ttattttcat tgcaatagtg tgttggaatt    7980
ttttgtgtct ctcactcgga aggacataag ggcggccgct agc                      8023
```

```
<210> SEQ ID NO 9
<211> LENGTH: 1672
<212> TYPE: PRT
<213> ORGANISM: Artificial Sequence
<220> FEATURE:
<223> OTHER INFORMATION: Description of Artificial Sequence: Synthetic
      chimeric polypeptide of AraH1,2 and 3 allergens
<220> FEATURE:
<221> NAME/KEY: misc_feature
<222> LOCATION: (1)..(27)
<223> OTHER INFORMATION: Signal
<220> FEATURE:
<221> NAME/KEY: misc_feature
<222> LOCATION: (28)..(380)
<223> OTHER INFORMATION: N-lamp
<220> FEATURE:
<221> NAME/KEY: misc_feature
<222> LOCATION: (383)..(983)
<223> OTHER INFORMATION: AraH1
<220> FEATURE:
<221> NAME/KEY: misc_feature
<222> LOCATION: (988)..(1138)
<223> OTHER INFORMATION: AraH2
<220> FEATURE:
<221> NAME/KEY: misc_feature
<222> LOCATION: (1143)..(1634)
<223> OTHER INFORMATION: AraH3
<220> FEATURE:
<221> NAME/KEY: misc_feature
<222> LOCATION: (1637)..(1672)
<223> OTHER INFORMATION: TM/CYTO

<400> SEQUENCE: 9

Met Ala Pro Arg Ser Ala Arg Arg Pro Leu Leu Leu Leu Leu Leu
1               5                   10                  15

Leu Leu Leu Gly Leu Met His Cys Ala Ser Ala Ala Met Phe Met Val
            20                  25                  30
```

```
Lys Asn Gly Asn Gly Thr Ala Cys Ile Met Ala Asn Phe Ser Ala Ala
             35                  40                  45

Phe Ser Val Asn Tyr Asp Thr Lys Ser Gly Pro Lys Asn Met Thr Leu
 50                  55                  60

Asp Leu Pro Ser Asp Ala Thr Val Val Leu Asn Arg Ser Ser Cys Gly
 65                  70                  75                  80

Lys Glu Asn Thr Ser Asp Pro Ser Leu Val Ile Ala Phe Gly Arg Gly
                 85                  90                  95

His Thr Leu Thr Leu Asn Phe Thr Arg Asn Ala Thr Arg Tyr Ser Val
            100                 105                 110

Gln Leu Met Ser Phe Val Tyr Asn Leu Ser Asp Thr His Leu Phe Pro
            115                 120                 125

Asn Ala Ser Ser Lys Glu Ile Lys Thr Val Glu Ser Ile Thr Asp Ile
    130                 135                 140

Arg Ala Asp Ile Asp Lys Lys Tyr Arg Cys Val Ser Gly Thr Gln Val
145                 150                 155                 160

His Met Asn Asn Val Thr Val Thr Leu His Asp Ala Thr Ile Gln Ala
                165                 170                 175

Tyr Leu Ser Asn Ser Ser Phe Ser Arg Gly Glu Thr Arg Cys Glu Gln
            180                 185                 190

Asp Arg Pro Ser Pro Thr Thr Ala Pro Pro Ala Pro Pro Ser Pro Ser
            195                 200                 205

Pro Ser Pro Val Pro Lys Ser Pro Ser Val Asp Lys Tyr Asn Val Ser
    210                 215                 220

Gly Thr Asn Gly Thr Cys Leu Leu Ala Ser Met Gly Leu Gln Leu Asn
225                 230                 235                 240

Leu Thr Tyr Glu Arg Lys Asp Asn Thr Thr Val Thr Arg Leu Leu Asn
                245                 250                 255

Ile Asn Pro Asn Lys Thr Ser Ala Ser Gly Ser Cys Gly Ala His Leu
            260                 265                 270

Val Thr Leu Glu Leu His Ser Glu Gly Thr Thr Val Leu Leu Phe Gln
            275                 280                 285

Phe Gly Met Asn Ala Ser Ser Ser Arg Phe Phe Leu Gln Gly Ile Gln
    290                 295                 300

Leu Asn Thr Ile Leu Pro Asp Ala Arg Asp Pro Ala Phe Lys Ala Ala
305                 310                 315                 320

Asn Gly Ser Leu Arg Ala Leu Gln Ala Thr Val Gly Asn Ser Tyr Lys
                325                 330                 335

Cys Asn Ala Glu Glu His Val Arg Val Thr Lys Ala Phe Ser Val Asn
            340                 345                 350

Ile Phe Lys Val Trp Val Gln Ala Phe Lys Val Glu Gly Gly Gln Phe
    355                 360                 365

Gly Ser Val Glu Glu Cys Leu Leu Asp Glu Asn Ser Leu Glu Lys Ser
370                 375                 380

Ser Pro Tyr Gln Lys Thr Glu Asn Pro Cys Ala Gln Arg Cys Leu
385                 390                 395                 400

Gln Ser Cys Gln Gln Glu Pro Asp Asp Leu Lys Gln Lys Ala Cys Glu
            405                 410                 415

Ser Arg Cys Thr Lys Leu Glu Tyr Asp Pro Arg Cys Val Tyr Asp Pro
            420                 425                 430

Arg Gly His Thr Gly Thr Thr Asn Gln Arg Ser Pro Pro Gly Glu Arg
            435                 440                 445

Thr Arg Gly Arg Gln Pro Gly Asp Tyr Asp Asp Asp Arg Arg Gln Pro
```

```
            450                 455                 460
Arg Arg Glu Glu Gly Gly Arg Trp Gly Pro Ala Gly Pro Arg Glu Arg
465                 470                 475                 480

Glu Arg Glu Glu Asp Trp Arg Gln Pro Arg Glu Asp Trp Arg Arg Pro
                485                 490                 495

Ser His Gln Gln Pro Arg Lys Ile Arg Pro Glu Gly Arg Glu Gly Glu
                500                 505                 510

Gln Glu Trp Gly Thr Pro Gly Ser His Val Arg Glu Gly Thr Ser Arg
                515                 520                 525

Asn Asn Pro Phe Tyr Phe Pro Ser Arg Arg Phe Ser Thr Arg Tyr Gly
530                 535                 540

Asn Gln Asn Gly Arg Ile Arg Val Leu Gln Arg Phe Asp Gln Arg Ser
545                 550                 555                 560

Arg Gln Phe Gln Asn Leu Gln Asn His Arg Ile Val Gln Ile Glu Ala
                565                 570                 575

Lys Pro Asn Thr Leu Val Leu Pro Lys His Ala Asp Ala Asp Asn Ile
                580                 585                 590

Leu Val Ile Gln Gln Gly Gln Ala Thr Val Thr Val Ala Asn Gly Asn
                595                 600                 605

Asn Arg Lys Ser Phe Asn Leu Asp Glu Gly His Ala Leu Arg Ile Pro
610                 615                 620

Ser Gly Phe Ile Ser Tyr Ile Leu Asn Arg His Asp Asn Gln Asn Leu
625                 630                 635                 640

Arg Val Ala Lys Ile Ser Met Pro Val Asn Thr Pro Gly Gln Phe Glu
                645                 650                 655

Asp Phe Phe Pro Ala Ser Ser Arg Asp Gln Ser Ser Tyr Leu Gln Gly
                660                 665                 670

Phe Ser Arg Asn Thr Leu Glu Ala Ala Phe Asn Ala Glu Phe Asn Glu
                675                 680                 685

Ile Arg Arg Val Leu Leu Glu Glu Asn Ala Gly Gly Glu Gln Glu Glu
690                 695                 700

Arg Gly Gln Arg Arg Trp Ser Thr Arg Ser Ser Glu Asn Asn Glu Gly
705                 710                 715                 720

Val Ile Val Lys Val Ser Lys Glu His Val Glu Glu Leu Thr Lys His
                725                 730                 735

Ala Lys Ser Val Ser Lys Lys Gly Ser Glu Glu Glu Gly Asp Ile Thr
                740                 745                 750

Asn Pro Ile Asn Leu Arg Glu Gly Glu Pro Asp Leu Ser Asn Asn Phe
                755                 760                 765

Gly Lys Leu Phe Glu Val Lys Pro Asp Lys Lys Asn Pro Gln Leu Gln
770                 775                 780

Asp Leu Asp Met Met Leu Thr Cys Val Glu Lys Glu Gly Ala Leu
785                 790                 795                 800

Met Leu Pro His Phe Asn Ser Lys Ala Met Val Ile Val Val Asn
                805                 810                 815

Lys Gly Thr Gly Asn Leu Glu Leu Val Ala Val Arg Lys Glu Gln Gln
                820                 825                 830

Gln Arg Gly Arg Arg Glu Glu Glu Asp Glu Asp Glu Glu Glu Glu
                835                 840                 845

Gly Ser Asn Arg Glu Val Arg Arg Tyr Thr Ala Arg Leu Lys Glu Gly
                850                 855                 860

Asp Val Phe Ile Met Pro Ala Ala His Pro Val Ala Ile Asn Ala Ser
865                 870                 875                 880
```

```
Ser Glu Leu His Leu Leu Gly Phe Gly Ile Asn Ala Glu Asn Asn His
            885                 890                 895

Arg Ile Phe Leu Ala Gly Asp Lys Asp Asn Val Ile Asp Gln Ile Glu
            900                 905                 910

Lys Gln Ala Lys Asp Leu Ala Phe Pro Gly Ser Gly Gln Val Glu
            915                 920             925

Lys Leu Ile Lys Asn Gln Lys Glu Ser His Phe Val Ser Ala Arg Pro
        930                 935                 940

Gln Ser Gln Ser Gln Ser Pro Ser Pro Glu Lys Glu Ser Pro Glu
945                 950                 955                 960

Lys Glu Asp Gln Glu Glu Asn Gln Gly Gly Lys Gly Pro Leu Leu
            965                 970                 975

Ser Ile Leu Lys Ala Phe Asn Gly Gly Gly Arg Gln Gln Trp Glu
            980                 985                 990

Leu Gln Gly Asp Arg Arg Cys Gln Ser Gln Leu Glu Arg Ala Asn Leu
            995                1000                1005

Arg Pro Cys Glu Gln His Leu Met Gln Lys Ile Gln Arg Asp Glu
        1010                1015                1020

Asp Ser Tyr Gly Arg Asp Pro Tyr Ser Pro Ser Gln Asp Pro Tyr
    1025                1030                1035

Ser Pro Ser Gln Asp Pro Arg Arg Asp Pro Tyr Ser Pro Ser
    1040                1045                1050

Pro Tyr Asp Arg Arg Gly Ala Gly Ser Ser Gln His Gln Glu Arg
    1055                1060                1065

Cys Cys Asn Glu Leu Asn Glu Phe Glu Asn Asn Gln Arg Cys Met
    1070                1075                1080

Cys Glu Ala Leu Gln Gln Ile Met Glu Asn Gln Ser Asp Arg Leu
    1085                1090                1095

Gln Gly Arg Gln Gln Glu Gln Phe Lys Arg Glu Leu Arg Asn
    1100                1105                1110

Leu Pro Gln Gln Cys Gly Leu Arg Ala Pro Gln Arg Cys Asp Leu
    1115                1120                1125

Glu Val Glu Ser Gly Gly Arg Asp Arg Tyr Gly Gly Gly Val
    1130                1135                1140

Thr Phe Arg Gln Gly Gly Glu Asn Glu Cys Gln Phe Gln Arg
    1145                1150                1155

Leu Asn Ala Gln Arg Pro Asp Asn Arg Ile Glu Ser Glu Gly Gly
    1160                1165                1170

Tyr Ile Glu Thr Trp Asn Pro Asn Asn Gln Glu Phe Gln Cys Ala
    1175                1180                1185

Gly Val Ala Leu Ser Arg Thr Val Leu Arg Arg Asn Ala Leu Arg
    1190                1195                1200

Arg Pro Phe Tyr Ser Asn Ala Pro Leu Glu Ile Tyr Val Gln Gln
    1205                1210                1215

Gly Ser Gly Tyr Phe Gly Leu Ile Phe Pro Gly Cys Pro Ser Thr
    1220                1225                1230

Tyr Glu Glu Pro Ala Gln Glu Gly Arg Arg Tyr Gln Ser Gln Lys
    1235                1240                1245

Pro Ser Arg Arg Phe Gln Val Gly Gln Asp Asp Pro Ser Gln Gln
    1250                1255                1260

Gln Gln Asp Ser His Gln Lys Val His Arg Phe Asp Glu Gly Asp
    1265                1270                1275
```

```
Leu Ile Ala Val Pro Thr Gly Val Ala Phe Trp Met Tyr Asn Asp
1280             1285                 1290

Glu Asp Thr Asp Val Val Thr Val Thr Leu Ser Asp Thr Ser Ser
1295             1300                 1305

Ile His Asn Gln Leu Asp Gln Phe Pro Arg Arg Phe Tyr Leu Ala
1310             1315                 1320

Gly Asn Gln Glu Gln Glu Phe Leu Arg Tyr Gln Gln Gln Gln Gly
1325             1330                 1335

Ser Arg Pro His Tyr Arg Gln Ile Ser Pro Arg Val Arg Gly Asp
1340             1345                 1350

Glu Gln Glu Asn Glu Gly Ser Asn Ile Phe Ser Gly Phe Ala Gln
1355             1360                 1365

Glu Phe Leu Gln His Ala Phe Gln Val Asp Arg Gln Thr Val Glu
1370             1375                 1380

Asn Leu Arg Gly Glu Asn Glu Arg Glu Gln Gly Ala Ile Val
1385             1390                 1395

Thr Val Lys Gly Gly Leu Arg Ile Leu Ser Pro Asp Glu Glu Asp
1400             1405                 1410

Glu Ser Ser Arg Ser Pro Pro Asn Arg Arg Glu Glu Phe Asp Glu
1415             1420                 1425

Asp Arg Ser Arg Pro Gln Gln Arg Gly Lys Tyr Asp Glu Asn Arg
1430             1435                 1440

Arg Gly Tyr Lys Asn Gly Ile Glu Glu Thr Ile Cys Ser Ala Ser
1445             1450                 1455

Val Lys Lys Asn Leu Gly Arg Ser Ser Asn Pro Asp Ile Tyr Asn
1460             1465                 1470

Pro Gln Ala Gly Ser Leu Arg Ser Val Asn Glu Leu Asp Leu Pro
1475             1480                 1485

Ile Leu Gly Trp Leu Gly Leu Ser Ala Gln His Gly Thr Ile Tyr
1490             1495                 1500

Arg Asn Ala Met Phe Val Pro His Tyr Thr Leu Asn Ala His Thr
1505             1510                 1515

Ile Val Val Ala Leu Asn Gly Arg Ala His Val Gln Val Val Asp
1520             1525                 1530

Ser Asn Gly Asn Arg Val Tyr Asp Glu Glu Leu Gln Glu Gly His
1535             1540                 1545

Val Leu Val Val Pro Gln Asn Phe Ala Val Ala Ala Lys Ala Gln
1550             1555                 1560

Ser Glu Asn Tyr Glu Tyr Leu Ala Phe Lys Thr Asp Ser Arg Pro
1565             1570                 1575

Ser Ile Ala Asn Gln Ala Gly Glu Asn Ser Ile Ile Asp Asn Leu
1580             1585                 1590

Pro Glu Glu Val Val Ala Asn Ser Tyr Arg Leu Pro Arg Glu Gln
1595             1600                 1605

Ala Arg Gln Leu Lys Asn Asn Asn Pro Phe Lys Phe Phe Val Pro
1610             1615                 1620

Pro Phe Asp His Gln Ser Met Arg Glu Val Ala Glu Phe Thr Leu
1625             1630                 1635

Ile Pro Ile Ala Val Gly Gly Ala Leu Ala Gly Leu Val Leu Ile
1640             1645                 1650

Val Leu Ile Ala Tyr Leu Val Gly Arg Lys Arg Ser His Ala Gly
1655             1660                 1665

Tyr Gln Thr Ile
```

1670

<210> SEQ ID NO 10
<211> LENGTH: 225
<212> TYPE: PRT
<213> ORGANISM: Cryptomeria japonica

<400> SEQUENCE: 10

```
Met Ala Lys Val Ser Asp Leu Ala Leu Leu Val Ala Gly Met Ala
1               5                   10                  15

Ile Ser Leu Tyr Ile Gln Glu Thr Gly Ala Val Lys Phe Asp Ile Lys
            20                  25                  30

Asn Gln Cys Gly Tyr Thr Val Trp Ala Ala Gly Leu Pro Gly Gly Gly
        35                  40                  45

Gln Gln Leu Thr Gln Gly Gln Thr Trp Thr Val Asn Leu Ala Ala Gly
    50                  55                  60

Thr Gln Ser Ala Arg Phe Trp Gly Arg Thr Gly Cys Ser Phe Asp Ala
65                  70                  75                  80

Ser Gly Lys Gly Thr Cys Gln Thr Gly Asp Cys Gly Gly Gln Leu Ser
                85                  90                  95

Cys Thr Val Ser Gly Ala Val Pro Ala Thr Leu Ala Glu Tyr Thr Gln
            100                 105                 110

Ser Asp Gln Asp Tyr Tyr Asp Val Ser Leu Val Asp Gly Phe Asn Ile
        115                 120                 125

Pro Leu Ser Ile Asn Pro Thr Asn Ala Gln Cys Thr Ala Pro Ala Cys
130                 135                 140

Lys Ala Asp Val Asn Ala Val Cys Pro Ala Glu Leu Lys Val Asp Gly
145                 150                 155                 160

Gly Cys Lys Ser Ala Cys Ala Ala Phe Gln Thr Asp Gln Tyr Cys Cys
                165                 170                 175

Thr Gly Thr Tyr Ala Asn Ser Cys Pro Ala Thr Asn Tyr Ser Met Ile
            180                 185                 190

Phe Lys Asn Gln Cys Pro Gln Ala Tyr Ser Tyr Pro Lys Asp Asp Thr
        195                 200                 205

Ala Thr Phe Ala Cys Pro Ser Gly Thr Asp Tyr Ser Ile Val Phe Cys
    210                 215                 220

Pro
225
```

<210> SEQ ID NO 11
<211> LENGTH: 281
<212> TYPE: PRT
<213> ORGANISM: Cryptomeria japonica

<400> SEQUENCE: 11

```
Met Gly Ile Met Ala Thr Gln Asn Ser Lys Ser Asn Ile Phe Trp Ser
1               5                   10                  15

Ser Ser Ala Ser Val Val Leu Val Leu Leu Leu Val Asp Val Gly
            20                  25                  30

Val Cys Gln Asn Cys Gly Cys Asn Gly Leu Cys Cys Ser Gln Tyr Gly
        35                  40                  45

Tyr Cys Gly Ser Gly Glu Ala Tyr Cys Gly Ala Gly Cys Lys Glu Gly
    50                  55                  60

Pro Cys Ser Ser Ser Pro Pro Ser Thr Gly Thr Gly Val Gly Ser
65                  70                  75                  80

Ile Val Ser Ser Asp Val Phe Asn Ser Ile Val Gly Gly Ala Ala Ser
```

```
                      85                  90                  95
Gly Cys Ala Gly Asn Gly Phe Tyr Thr Tyr Asp Ser Phe Ile Ser Ala
                100                 105                 110

Ala Asn Ala Phe Asn Gly Phe Gly Thr Ser Gly Ser Ser Asp Val Asn
            115                 120                 125

Lys Arg Glu Ile Ala Ala Phe Phe Ala Asn Ala Ala His Glu Thr Gly
        130                 135                 140

Gly Phe Cys Tyr Ile Glu Glu Gln Asn Pro Thr Ser Ile Tyr Cys Asp
145                 150                 155                 160

Ala Ser Asn Thr Gln Tyr Pro Cys Ala Ser Gly Lys Thr Tyr His Gly
                165                 170                 175

Arg Gly Pro Leu Gln Leu Ser Trp Asn Tyr Asn Tyr Gly Ala Ala Gly
            180                 185                 190

Ser Tyr Ile Gln Phe Asp Gly Leu Asn Asn Pro Glu Ile Val Gly Thr
        195                 200                 205

Asp Ser Thr Ile Ser Phe Lys Thr Ala Val Trp Phe Trp Met Val Asn
210                 215                 220

Ser Asn Cys His Thr Ala Ile Thr Ser Gly Gln Gly Phe Gly Ala Thr
225                 230                 235                 240

Ile Arg Ala Ile Asn Ser Met Glu Cys Asp Gly Gly Asn Ala Ala Thr
                245                 250                 255

Val Ala Ser Arg Val Asn Tyr Tyr Gln Lys Phe Cys Gln Gln Leu Asn
            260                 265                 270

Val Asp Thr Gly Ser Ala Leu Gln Cys
        275                 280

<210> SEQ ID NO 12
<211> LENGTH: 306
<212> TYPE: PRT
<213> ORGANISM: Cryptomeria japonica

<400> SEQUENCE: 12

Met Gly Gly Ser Arg Val Leu Ile Ile Gly Gly Thr Gly Tyr Ile Gly
1               5                   10                  15

Arg His Val Thr Asn Ala Ser Leu Ala Gln Gly His Pro Thr Phe Leu
            20                  25                  30

Leu Val Arg Glu Ile Thr Pro Ser Asn Pro Glu Lys Ala Gln Leu Leu
        35                  40                  45

Glu Ser Phe Thr Ser Lys Gly Ala Thr Leu Val Gln Gly Ser Ile Asp
    50                  55                  60

Asp His Ala Ser Leu Val Ala Ala Leu Lys Lys Val Asp Val Val Ile
65                  70                  75                  80

Ser Thr Leu Gly Ala Pro Gln Ile Ala Asp Gln Phe Asn Leu Ile Lys
                85                  90                  95

Ala Ile Lys Glu Val Gly Thr Ile Lys Arg Phe Phe Pro Ser Glu Phe
            100                 105                 110

Gly Asn Asp Val Asp Lys His His Ala Val Glu Pro Met Lys Ser Met
        115                 120                 125

Phe Asp Leu Lys Ile Lys Leu Arg Arg Thr Ile Glu Ala Glu Gly Ile
    130                 135                 140

Pro His Thr Tyr Val Val Pro His Cys Phe Ala Gly Tyr Phe Leu Thr
145                 150                 155                 160

Asn Leu Ala Gln Leu Gly Leu Ala Ala Pro Pro Arg Asp Lys Ile Val
                165                 170                 175
```

Ile Tyr Gly Asp Gly Thr Thr Lys Ala Val Tyr Met Lys Glu Asp
                180                 185                 190

Ile Gly Thr Phe Thr Ile Lys Ala Val Asp Asp Pro Arg Thr Leu Asn
            195                 200                 205

Lys Thr Leu Tyr Leu Lys Pro Pro Ala Asn Thr Ile Ser Thr Asn Asp
210                 215                 220

Leu Val Ala Leu Trp Glu Ala Lys Ile Gly Lys Thr Leu Glu Lys Val
225                 230                 235                 240

Tyr Leu Ser Glu Glu Gln Val Leu Lys Leu Leu Gln Asp Thr Pro Phe
                245                 250                 255

Pro Gly Thr Phe Met Val Ser Ile Phe His Thr Ile Tyr Val Lys Gly
            260                 265                 270

Asp Gln Thr Asn Phe Gln Ile Gly Pro Asp Gly Val Glu Ala Ser Ala
        275                 280                 285

Leu Tyr Pro Asp Val Lys Tyr Thr Thr Val Glu Glu Tyr Ile Ser Ala
290                 295                 300

Phe Val
305

<210> SEQ ID NO 13
<211> LENGTH: 165
<212> TYPE: PRT
<213> ORGANISM: Cryptomeria japonica

<400> SEQUENCE: 13

Met Ala Met Arg Met Lys Ser Ser Met Ser Ser Tyr Arg Phe Ser
1               5                   10                  15

Tyr Cys Gln Met Met Leu Val Leu Met Val Met Thr Leu Val Gln Ile
                20                  25                  30

Gly Ala Ala Gln Ser Asp Thr Asn Ser Cys Val Asn Ser Leu Val Pro
            35                  40                  45

Cys Ala Ser Tyr Leu Asn Ala Thr Thr Lys Pro Pro Asp Ser Cys Cys
        50                  55                  60

Val Pro Leu Leu Asn Val Ile Gln Thr Gln Gln Cys Leu Cys Asn
65                  70                  75                  80

Leu Leu Asn Ser Ser Ile Val Lys Gln Ser Ile Asn Ile Thr Gln
                85                  90                  95

Ala Leu Asn Ile Pro Arg Leu Cys Gly Asp Thr Asn Val Ser Thr Asp
            100                 105                 110

Ala Cys Ser Thr Asn Ala Thr Ala Asn Ala Pro Ser Ala Ser Thr Thr
        115                 120                 125

Pro Ser Val Pro Ala Asp Thr Gly Asp Ser Ser Gly Ile Gly Ala Thr
130                 135                 140

Ser Leu Gln Ile Phe Leu Pro Leu Leu Ala Val Phe Phe Leu Gly Val
145                 150                 155                 160

Phe Lys Ser Phe Pro
                165

<210> SEQ ID NO 14
<211> LENGTH: 472
<212> TYPE: PRT
<213> ORGANISM: Cryptomeria japonica

<400> SEQUENCE: 14

Met Ala Arg Arg Leu Cys Ser Phe Leu Leu Ser Phe Leu Ile Ile Val
1               5                   10                  15

```
Ser Val Trp Ala Glu Asn Ser Lys Phe Ala Arg Leu Asn Leu Ala Ser
            20                  25                  30

Phe Thr Trp Lys Asp Ala Glu Asp Asn Lys Asn Cys Ser Ala Gly Glu
            35                  40                  45

Leu Glu Thr Ser Ser Leu Ser Val Met His Ile Gln Gly Lys Cys Ser
    50                  55                  60

Pro Phe Arg Leu Leu Asn Ser Ser Trp Trp Thr Ala Val Ser Glu Ser
65                  70                  75                  80

Ile Lys Gly Asp Thr Ala Arg Tyr Arg Ala Met Val Lys Gly Gly Trp
                85                  90                  95

Ser Ala Gly Lys Thr Met Val Asn Pro Gln Glu Asp Ala Asp Ile Pro
            100                 105                 110

Leu Ala Ser Gly Gln Ala Glu Ser Ser Ser Asn Tyr Ile Ile Lys Leu
        115                 120                 125

Gly Phe Gly Thr Pro Pro Gln Ser Phe Tyr Thr Val Leu Asp Thr Gly
    130                 135                 140

Ser Asn Ile Ala Trp Ile Pro Cys Asn Pro Cys Ser Gly Cys Ser Ser
145                 150                 155                 160

Lys Gln Gln Pro Phe Glu Pro Ser Lys Ser Ser Thr Tyr Asn Tyr Leu
                165                 170                 175

Thr Cys Ala Ser Gln Gln Cys Gln Leu Leu Arg Val Cys Thr Lys Ser
            180                 185                 190

Asp Asn Ser Val Asn Cys Ser Leu Thr Gln Arg Tyr Gly Asp Gln Ser
        195                 200                 205

Glu Val Asp Glu Ile Leu Ser Ser Glu Thr Leu Ser Val Gly Ser Gln
    210                 215                 220

Gln Val Glu Asn Phe Val Phe Gly Cys Ser Asn Ala Ala Arg Gly Leu
225                 230                 235                 240

Ile Gln Arg Thr Pro Ser Leu Val Gly Phe Gly Arg Asn Pro Leu Ser
                245                 250                 255

Phe Val Ser Gln Thr Ala Thr Leu Tyr Asp Ser Thr Phe Ser Tyr Cys
            260                 265                 270

Leu Pro Ser Leu Phe Ser Ser Ala Phe Thr Gly Ser Leu Leu Leu Gly
        275                 280                 285

Lys Glu Ala Leu Ser Ala Gln Gly Leu Lys Phe Thr Pro Leu Leu Ser
    290                 295                 300

Asn Ser Arg Tyr Pro Ser Phe Tyr Tyr Val Gly Leu Asn Gly Ile Ser
305                 310                 315                 320

Val Gly Glu Glu Leu Val Ser Ile Pro Ala Gly Thr Leu Ser Leu Asp
                325                 330                 335

Glu Ser Thr Gly Arg Gly Thr Ile Ile Asp Ser Gly Thr Val Ile Thr
            340                 345                 350

Arg Leu Val Glu Pro Ala Tyr Asn Ala Met Arg Asp Ser Phe Arg Ser
        355                 360                 365

Gln Leu Ser Asn Leu Thr Met Ala Ser Pro Thr Asp Leu Phe Asp Thr
    370                 375                 380

Cys Thr Asn Arg Pro Ser Gly Asp Val Glu Phe Pro Leu Ile Thr Leu
385                 390                 395                 400

His Phe Asp Asp Asn Leu Asp Leu Thr Leu Pro Leu Asp Asn Ile Leu
                405                 410                 415

Tyr Pro Gly Asn Asp Gly Ser Val Leu Cys Leu Ala Phe Gly Leu
            420                 425                 430

Pro Pro Gly Gly Gly Asp Asp Val Leu Ser Thr Phe Gly Asn Tyr Gln
```

```
                435                 440                 445
Gln Gln Lys Leu Arg Ile Val His Asp Val Ala Glu Ser Arg Leu Gly
    450                 455                 460

Ile Ala Ser Gly Asn Cys Asp Gly
465                 470

<210> SEQ ID NO 15
<211> LENGTH: 348
<212> TYPE: PRT
<213> ORGANISM: Cryptomeria japonica

<400> SEQUENCE: 15

Met Glu Leu Leu Lys Gln His Arg Tyr Met Phe Leu Leu Ile Ser Cys
1               5                   10                  15

Ile Val Ile Leu Leu Asn Ser Met His Ala Asp Cys Glu Gln Ile Gly
            20                  25                  30

Val Asn Tyr Gly Met Asp Gly Asn Asn Leu Pro Ser Ala Gly Asp Val
        35                  40                  45

Val Ser Leu Met Lys Lys Asn Asn Ile Gly Lys Met Arg Ile Phe Gly
    50                  55                  60

Pro Asn Ala Asp Val Leu Arg Ala Phe Ala Asn Ser Arg Ile Glu Val
65                  70                  75                  80

Ile Val Gly Val Glu Asn Lys Gly Leu Glu Ala Val Ala Ser Ser Gln
                85                  90                  95

Asp Ser Ala Asn Gly Trp Val Asn Asp Asn Ile Lys Pro Phe Tyr Pro
            100                 105                 110

Ser Thr Asn Ile Lys Tyr Ile Ala Val Gly Asn Glu Val Leu Glu Met
        115                 120                 125

Pro Asp Asn Ala Gln Tyr Val Ser Phe Leu Val Pro Ala Ile Lys Asn
    130                 135                 140

Ile Gln Thr Ala Leu Glu Asn Ala Asn Leu Gln Asn Asn Ile Lys Val
145                 150                 155                 160

Ser Thr Ala His Ala Met Thr Val Ile Gly Thr Ser Ser Pro Pro Ser
                165                 170                 175

Lys Gly Thr Phe Lys Asp Ala Val Lys Asp Ser Met Ser Ser Ile Leu
            180                 185                 190

Gln Phe Leu Gln Asp His Gly Ser Pro Phe Met Ala Asn Val Tyr Pro
        195                 200                 205

Tyr Phe Ser Tyr Asp Gly Asp Arg Ser Ile Lys Leu Asp Tyr Ala Leu
    210                 215                 220

Phe Asn Pro Thr Pro Val Val Asp Glu Gly Leu Ser Tyr Thr Asn
225                 230                 235                 240

Leu Phe Asp Ala Met Val Asp Ala Val Leu Ser Ala Met Glu Ser Leu
                245                 250                 255

Gly His Pro Asn Ile Pro Ile Val Ile Thr Glu Ser Gly Trp Pro Ser
            260                 265                 270

Ala Gly Lys Ser Val Ala Thr Ile Glu Asn Ala Gln Thr Tyr Asn Asn
        275                 280                 285

Asn Leu Ile Lys His Val Leu Ser Asn Ala Gly Thr Pro Lys Arg Pro
    290                 295                 300

Gly Ser Ser Ile Glu Thr Tyr Ile Phe Ala Leu Phe Asn Glu Asn Leu
305                 310                 315                 320

Lys Gly Pro Ala Glu Val Glu Lys His Phe Gly Leu Phe Asn Pro Asp
                325                 330                 335
```

Glu Gln Pro Val Tyr Pro Val Lys Phe Ser Leu Asn
            340                 345

<210> SEQ ID NO 16
<211> LENGTH: 375
<212> TYPE: PRT
<213> ORGANISM: Chamaecyparis obtusa

<400> SEQUENCE: 16

Met Ala Ser Cys Thr Leu Leu Ala Val Leu Val Phe Leu Cys Ala Ile
1               5                   10                  15

Val Ser Cys Phe Ser Asp Asn Pro Ile Asp Ser Cys Trp Arg Gly Asp
            20                  25                  30

Ala Asn Trp Asp Gln Asn Arg Met Lys Leu Ala Asp Cys Ala Val Gly
        35                  40                  45

Phe Gly Ser Ser Ala Met Gly Gly Lys Gly Ala Phe Tyr Thr Val
    50                  55                  60

Thr Ser Ser Asp Asp Pro Val Asn Pro Ala Pro Gly Thr Leu Arg
65                  70                  75                  80

Tyr Gly Ala Thr Arg Glu Arg Ser Leu Trp Ile Ile Phe Ser Lys Asn
                85                  90                  95

Leu Asn Ile Lys Leu Asn Met Pro Leu Tyr Ile Ala Gly Asn Lys Thr
            100                 105                 110

Ile Asp Gly Arg Gly Ala Glu Val His Ile Gly Asn Gly Pro Cys
        115                 120                 125

Leu Phe Met Arg Thr Val Ser His Val Ile Leu His Gly Leu Asn Ile
    130                 135                 140

His Gly Cys Asn Thr Ser Val Ser Gly Asn Val Leu Ile Ser Glu Ala
145                 150                 155                 160

Ser Gly Val Val Pro Val His Ala Gln Asp Gly Asp Ala Ile Thr Met
                165                 170                 175

Arg Asn Val Thr Asp Val Trp Ile Asp His Asn Ser Leu Ser Asp Ser
            180                 185                 190

Ser Asp Gly Leu Val Asp Val Thr Leu Ala Ser Thr Gly Val Thr Ile
        195                 200                 205

Ser Asn Asn His Phe Phe Asn His His Lys Val Met Leu Leu Gly His
    210                 215                 220

Ser Asp Ile Tyr Ser Asp Asp Lys Ser Met Lys Val Thr Val Ala Phe
225                 230                 235                 240

Asn Gln Phe Gly Pro Asn Ala Gly Gln Arg Met Pro Arg Ala Arg Tyr
                245                 250                 255

Gly Leu Ile His Val Ala Asn Asn Tyr Asp Pro Trp Ser Ile Tyr
            260                 265                 270

Ala Ile Gly Gly Ser Ser Asn Pro Thr Ile Leu Ser Glu Gly Asn Ser
        275                 280                 285

Phe Thr Ala Pro Asn Asp Ser Asp Lys Lys Glu Val Thr Arg Arg Val
    290                 295                 300

Gly Cys Glu Ser Pro Ser Thr Cys Ala Asn Trp Val Trp Arg Ser Thr
305                 310                 315                 320

Gln Asp Ser Phe Asn Asn Gly Ala Tyr Phe Val Ser Ser Gly Lys Asn
                325                 330                 335

Glu Gly Thr Asn Ile Tyr Asn Asn Glu Ala Phe Lys Val Glu Asn
            340                 345                 350

Gly Ser Ala Ala Pro Gln Leu Thr Lys Asn Ala Gly Val Leu Thr Cys
        355                 360                 365

Ile Leu Ser Lys Pro Cys Ser
    370             375

<210> SEQ ID NO 17
<211> LENGTH: 367
<212> TYPE: PRT
<213> ORGANISM: Juniperus ashei

<400> SEQUENCE: 17

Met Ala Ser Pro Cys Leu Ile Ala Val Leu Val Phe Leu Cys Ala Ile
1               5                   10                  15

Val Ser Cys Tyr Ser Asp Asn Pro Ile Asp Ser Cys Trp Arg Gly Asp
            20                  25                  30

Ser Asn Trp Asp Gln Asn Arg Met Lys Leu Ala Asp Cys Ala Val Gly
        35                  40                  45

Phe Gly Ser Ser Thr Met Gly Gly Lys Gly Gly Asp Phe Tyr Thr Val
    50                  55                  60

Thr Ser Thr Asp Asp Asn Pro Val Asn Pro Thr Pro Gly Thr Leu Arg
65                  70                  75                  80

Tyr Gly Ala Thr Arg Glu Lys Ala Leu Trp Ile Ile Phe Ser Gln Asn
                85                  90                  95

Met Asn Ile Lys Leu Lys Met Pro Leu Tyr Val Ala Gly His Lys Thr
            100                 105                 110

Ile Asp Gly Arg Gly Ala Asp Val His Leu Gly Asn Gly Gly Pro Cys
        115                 120                 125

Leu Phe Met Arg Lys Val Ser His Val Ile Leu His Ser Leu His Ile
    130                 135                 140

His Gly Cys Asn Thr Ser Val Leu Gly Asp Val Leu Val Ser Glu Ser
145                 150                 155                 160

Ile Gly Val Glu Pro Val His Ala Gln Asp Gly Asp Ala Ile Thr Met
                165                 170                 175

Arg Asn Val Thr Asn Ala Trp Ile Asp His Asn Ser Leu Ser Asp Cys
            180                 185                 190

Ser Asp Gly Leu Ile Asp Val Thr Leu Gly Ser Thr Gly Ile Thr Ile
        195                 200                 205

Ser Asn Asn His Phe Phe Asn His His Lys Val Met Leu Leu Gly His
    210                 215                 220

Asp Asp Thr Tyr Asp Asp Lys Ser Met Lys Val Thr Val Ala Phe
225                 230                 235                 240

Asn Gln Phe Gly Pro Asn Ala Gly Gln Arg Met Pro Arg Ala Arg Tyr
                245                 250                 255

Gly Leu Val His Val Ala Asn Asn Tyr Asp Pro Trp Asn Ile Tyr
            260                 265                 270

Ala Ile Gly Gly Ser Ser Asn Pro Thr Ile Leu Ser Glu Gly Asn Ser
        275                 280                 285

Phe Thr Ala Pro Ser Glu Ser Tyr Lys Lys Glu Val Thr Lys Arg Ile
    290                 295                 300

Gly Cys Glu Ser Pro Ser Ala Cys Ala Asn Trp Val Trp Arg Ser Thr
305                 310                 315                 320

Arg Asp Ala Phe Ile Asn Gly Ala Tyr Phe Val Ser Ser Gly Lys Thr
                325                 330                 335

Glu Glu Thr Asn Ile Tyr Asn Ser Asn Glu Ala Phe Lys Val Glu Asn
            340                 345                 350

Gly Asn Ala Ala Pro Gln Leu Thr Lys Asn Ala Gly Val Val Thr

<210> SEQ ID NO 18
<211> LENGTH: 367
<212> TYPE: PRT
<213> ORGANISM: Juniperus virginiana

<400> SEQUENCE: 18

Met Ala Ser Pro Cys Leu Ile Ala Phe Leu Val Phe Leu Cys Ala Ile
1               5                   10                  15

Val Ser Cys Cys Ser Asp Asn Pro Ile Asp Ser Cys Trp Arg Gly Asp
            20                  25                  30

Ser Asn Trp Gly Gln Asn Arg Met Lys Leu Ala Asp Cys Ala Val Gly
        35                  40                  45

Phe Gly Ser Ser Thr Met Gly Gly Lys Gly Gly Asp Phe Tyr Thr Val
    50                  55                  60

Thr Ser Ala Asp Asp Asn Pro Val Asn Pro Thr Pro Gly Thr Leu Arg
65                  70                  75                  80

Tyr Gly Ala Thr Arg Glu Lys Thr Leu Trp Ile Ile Phe Ser Gln Asn
                85                  90                  95

Met Asn Ile Lys Leu Lys Met Pro Leu Tyr Val Ala Gly His Lys Thr
            100                 105                 110

Ile Asp Gly Arg Gly Ala Asp Val His Leu Gly Asn Gly Pro Cys
        115                 120                 125

Leu Phe Met Arg Lys Val Ser His Val Ile Leu His Gly Leu His Ile
    130                 135                 140

His Gly Cys Asn Thr Ser Val Leu Gly Asp Val Leu Val Ser Glu Ser
145                 150                 155                 160

Ile Gly Val Val Pro Val His Ala Gln Asp Gly Asp Ala Ile Thr Met
                165                 170                 175

Arg Asn Val Thr Asn Ala Trp Ile Asp His Asn Ser Leu Ser Asp Cys
            180                 185                 190

Ser Asp Gly Leu Ile Asp Val Thr Leu Gly Ser Thr Gly Ile Thr Ile
        195                 200                 205

Phe Asn Asn His Phe Phe Asn His His Lys Val Met Leu Leu Gly His
    210                 215                 220

Asp Asp Thr Tyr Asp Asp Asp Lys Ser Met Lys Val Thr Val Ala Phe
225                 230                 235                 240

Asn Gln Phe Gly Pro Asn Ala Gly Gln Arg Met Pro Arg Ala Arg Tyr
                245                 250                 255

Gly Leu Val His Val Ala Asn Asn Tyr Asp Pro Trp Asn Ile Tyr
            260                 265                 270

Ala Ile Gly Gly Ser Ser Asn Pro Thr Ile Leu Ser Glu Gly Asn Ser
        275                 280                 285

Phe Thr Ala Pro Asn Glu Asn Tyr Lys Tyr Glu Val Thr Lys Arg Ile
    290                 295                 300

Gly Cys Glu Ser Thr Ser Ala Cys Ala Asn Trp Val Trp Arg Ser Thr
305                 310                 315                 320

Arg Asp Ala Phe Ser Asn Gly Ala Tyr Phe Val Ser Ser Gly Lys Ile
                325                 330                 335

Glu Glu Thr Asn Ile Tyr Asn Ser Asn Glu Ala Phe Lys Val Glu Asn
            340                 345                 350

Gly Asn Ala Ala Pro Gln Leu Thr Lys Asn Ala Gly Val Val Ala
        355                 360                 365

<210> SEQ ID NO 19
<211> LENGTH: 367
<212> TYPE: PRT
<213> ORGANISM: Hexalectris arizonica

<400> SEQUENCE: 19

```
Met Ala Ser Pro Cys Leu Val Ala Val Leu Val Phe Leu Cys Ala Ile
1               5                   10                  15

Val Ser Cys Tyr Ser Asp Asn Pro Ile Asp Ser Cys Trp Arg Gly Asp
            20                  25                  30

Ser Asn Trp Asp Gln Asn Arg Met Lys Leu Ala Asp Cys Val Val Gly
        35                  40                  45

Phe Gly Ser Leu Thr Met Gly Gly Lys Gly Gly Glu Ile Tyr Thr Val
    50                  55                  60

Thr Ser Ser Asp Asp Asn Pro Val Asn Pro Thr Pro Gly Thr Leu Arg
65                  70                  75                  80

Tyr Gly Ala Thr Arg Glu Lys Ala Leu Trp Ile Ile Phe Ser Gln Asn
                85                  90                  95

Met Asn Ile Lys Leu Gln Met Pro Leu Tyr Val Ala Gly Tyr Lys Thr
            100                 105                 110

Ile Asp Gly Arg Gly Ala Asp Val His Leu Gly Asn Gly Gly Pro Cys
        115                 120                 125

Leu Phe Met Arg Thr Ala Ser His Val Ile Leu His Gly Leu His Ile
    130                 135                 140

His Gly Cys Asn Thr Ser Val Leu Gly Asp Val Leu Val Ser Glu Ser
145                 150                 155                 160

Ile Gly Val Glu Pro Val His Ala Gln Asp Gly Asp Ala Ile Thr Met
                165                 170                 175

Arg Asn Val Thr Asn Ala Trp Ile Asp His Asn Ser Leu Ser Asp Cys
            180                 185                 190

Ser Asp Gly Leu Ile Asp Val Thr Leu Gly Ser Thr Gly Ile Thr Ile
        195                 200                 205

Ser Asn Asn His Phe Phe Asn His His Lys Val Met Leu Leu Gly His
    210                 215                 220

Asp Asp Thr Tyr Asp Asp Asp Ile Ser Met Lys Val Thr Val Ala Phe
225                 230                 235                 240

Asn Gln Phe Gly Pro Asn Ala Gly Gln Arg Met Pro Arg Ala Arg Tyr
                245                 250                 255

Gly Leu Val His Val Ala Asn Asn Tyr Asp Gln Trp Asn Ile Tyr
            260                 265                 270

Ala Ile Gly Gly Ser Ser Asn Pro Thr Ile Leu Ser Glu Gly Asn Ser
        275                 280                 285

Pro Thr Ala Pro Ser Glu Ser Tyr Lys Lys Glu Val Thr Lys Arg Ile
    290                 295                 300

Gly Cys Glu Ser Thr Ser Ala Cys Ala Asn Trp Val Trp Arg Phe Thr
305                 310                 315                 320

Arg Asp Ala Phe Thr Asn Gly Ala Tyr Phe Val Ser Ser Gly Lys Ala
                325                 330                 335

Glu Glu Thr Asn Ile Tyr Asn Ser Asn Glu Ala Phe Lys Val Glu Asn
            340                 345                 350

Gly Asn Ala Ala Pro Gln Leu Thr Gln Asn Ala Gly Val Val Thr
        355                 360                 365
```

<210> SEQ ID NO 20

<211> LENGTH: 366
<212> TYPE: PRT
<213> ORGANISM: Juniperus oxycedrus

<400> SEQUENCE: 20

Met Ala Ser Pro Cys Leu Arg Ala Val Leu Val Phe Leu Cys Ala Ile
1               5                   10                  15

Val Ser Cys Tyr Ser Asp Asn Pro Ile Asp Ser Cys Trp Arg Gly Asp
            20                  25                  30

Ser Asn Trp Gly Gln Asn Arg Met Lys Leu Ala Asp Cys Val Val Gly
        35                  40                  45

Phe Gly Ser Ser Thr Met Gly Gly Lys Gly Glu Phe Tyr Thr Val
50                  55                  60

Thr Ser Ala Glu Asp Asn Pro Val Asn Pro Thr Pro Gly Thr Leu Arg
65                  70                  75                  80

Tyr Gly Ala Thr Arg Glu Lys Ala Leu Trp Ile Ile Phe Ser Gln Asn
                85                  90                  95

Met Asn Ile Lys Leu Lys Met Pro Leu Tyr Val Ala Gly His Lys Thr
            100                 105                 110

Ile Asp Gly Arg Gly Ala Asp Val His Leu Gly Asn Gly Gly Pro Cys
        115                 120                 125

Leu Phe Met Arg Lys Val Ser His Val Ile Leu His Gly Leu His Ile
130                 135                 140

Gly Cys Asn Thr Ser Val Leu Gly Asp Val Leu Val Ser Glu Ser Ile
145                 150                 155                 160

Gly Val Glu Pro Val His Ala Gln Asp Gly Asp Ala Ile Thr Met Arg
                165                 170                 175

Asn Val Thr Asn Ala Trp Ile Asp His Asn Ser Leu Ser Asp Cys Ser
            180                 185                 190

Asp Gly Leu Ile Asp Val Thr Leu Gly Ser Thr Gly Ile Thr Ile Ser
        195                 200                 205

Asn Asn His Phe Phe Asn His His Lys Val Met Leu Leu Gly His Asp
210                 215                 220

Asp Thr Tyr Asp Asn Asp Lys Ser Met Lys Val Thr Val Ala Phe Asn
225                 230                 235                 240

Gln Phe Gly Pro Asn Ala Gly Gln Arg Met Pro Arg Ala Arg Tyr Gly
                245                 250                 255

Leu Val His Val Ala Asn Asn Tyr Asp Pro Trp Asn Ile Tyr Ala
            260                 265                 270

Ile Gly Gly Ser Ser Asn Pro Thr Ile Leu Ser Glu Gly Asn Ser Phe
        275                 280                 285

Thr Ala Pro Ser Glu Ser Tyr Lys Lys Glu Val Thr Lys Arg Ile Gly
290                 295                 300

Cys Glu Ser Thr Ser Ala Cys Ala Asn Trp Val Trp Arg Ser Thr Arg
305                 310                 315                 320

Asp Ala Phe Thr Asn Gly Ala Tyr Phe Val Ser Ser Gly Lys Ile Glu
                325                 330                 335

Glu Thr Asn Ile Tyr Asn Ser Asn Glu Ala Phe Lys Val Glu Asn Gly
            340                 345                 350

Asn Ala Ala Pro Gln Leu Thr Lys Asn Ala Gly Val Val Thr
        355                 360                 365

<210> SEQ ID NO 21
<211> LENGTH: 367
<212> TYPE: PRT

<213> ORGANISM: Cupressus sempervirens

<400> SEQUENCE: 21

```
Met Asp Ser Pro Cys Leu Ile Ala Val Leu Val Phe Leu Cys Ala Ile
1               5                   10                  15

Val Ser Cys Tyr Ser Asp Asn Pro Ile Asp Ser Cys Trp Arg Gly Asp
            20                  25                  30

Ser Asn Trp Asp Gln Asn Arg Met Lys Leu Ala Asp Cys Ala Val Gly
        35                  40                  45

Phe Gly Ser Ser Thr Met Gly Gly Lys Gly Gly Asp Ile Tyr Thr Val
    50                  55                  60

Thr Ser Ala Glu Asp Asn Pro Val Asn Pro Thr Pro Gly Thr Leu Arg
65                  70                  75                  80

Tyr Gly Ala Thr Arg Glu Lys Ala Leu Trp Ile Ile Phe Ser Gln Asn
                85                  90                  95

Met Asn Ile Lys Leu Lys Met Pro Leu Tyr Val Ala Gly His Lys Thr
            100                 105                 110

Ile Asp Gly Arg Gly Ala Asp Val His Leu Gly Asn Gly Gly Pro Cys
        115                 120                 125

Leu Phe Met Arg Lys Val Ser His Val Ile Leu His Gly Leu His Ile
    130                 135                 140

His Gly Cys Asn Thr Ser Val Leu Gly Asn Val Leu Val Ser Glu Ser
145                 150                 155                 160

Ile Gly Val Glu Pro Val His Ala Gln Asp Gly Asp Ala Ile Thr Met
                165                 170                 175

Arg Asn Val Thr Asn Ala Trp Ile Asp His Asn Ser Leu Ser Asp Cys
            180                 185                 190

Ser Asp Gly Leu Ile Asp Val Thr Leu Ser Ser Thr Gly Ile Thr Ile
        195                 200                 205

Ser Asn Asn His Phe Phe Asn His His Lys Val Met Leu Leu Gly His
    210                 215                 220

Asp Asp Thr Tyr Asp Asp Asp Lys Ser Met Lys Val Thr Val Ala Phe
225                 230                 235                 240

Asn Gln Phe Gly Pro Asn Ala Gly Gln Arg Met Pro Arg Ala Arg Tyr
                245                 250                 255

Gly Leu Val His Val Ala Asn Asn Asn Tyr Asp Gln Trp Asn Ile Tyr
            260                 265                 270

Ala Ile Gly Gly Ser Ser Asn Pro Thr Ile Leu Ser Glu Gly Asn Ser
        275                 280                 285

Phe Ala Ala Pro Asn Glu Asn Tyr Lys Lys Glu Val Thr Lys Arg Ile
    290                 295                 300

Gly Cys Val Ser Thr Ser Ala Cys Ala Asn Trp Val Trp Arg Ser Thr
305                 310                 315                 320

Arg Asp Ala Phe Ser Asn Gly Ala Tyr Phe Val Ser Ser Gly Lys Thr
                325                 330                 335

Glu Glu Thr Asn Ile Tyr Thr Ser Asn Glu Ala Phe Lys Val Glu Asn
            340                 345                 350

Gly Asn Leu Ala Pro Gln Leu Thr Lys Asn Ala Gly Val Val Ala
        355                 360                 365
```

<210> SEQ ID NO 22
<211> LENGTH: 514
<212> TYPE: PRT
<213> ORGANISM: Chamaecyparis obtusa

```
<400> SEQUENCE: 22

Met Gly Met Lys Phe Met Ala Ala Val Ala Phe Leu Ala Leu Gln Leu
1               5                   10                  15

Ile Val Met Ala Ala Glu Asp Gln Ser Ala Gln Ile Met Leu Asp
            20                  25                  30

Ser Asp Ile Glu Glu Tyr Leu Arg Ser Asn Arg Ser Leu Lys Lys Leu
                35                  40                  45

Val His Ser Arg His Asp Ala Ala Thr Val Phe Asn Val Glu Gln Tyr
    50                  55                  60

Gly Ala Val Gly Asp Gly Lys His Asp Ser Thr Glu Ala Phe Ala Thr
65                  70                  75                  80

Thr Trp Asn Ala Ala Cys Lys Lys Ala Ser Ala Val Leu Leu Val Pro
                85                  90                  95

Ala Asn Lys Lys Phe Phe Val Asn Asn Leu Val Phe Arg Gly Pro Cys
            100                 105                 110

Gln Pro His Leu Ser Phe Lys Val Asp Gly Thr Ile Val Ala Gln Pro
        115                 120                 125

Asp Pro Ala Arg Trp Lys Asn Ser Lys Ile Trp Leu Gln Phe Ala Gln
130                 135                 140

Leu Thr Asp Phe Asn Leu Met Gly Thr Phe Val Ile Asp Gly Gln Gly
145                 150                 155                 160

Gln Gln Trp Trp Ala Gly Gln Cys Lys Val Val Asn Gly Arg Thr Val
                165                 170                 175

Cys Asn Asp Arg Asn Arg Pro Thr Ala Ile Lys Ile Asp Tyr Ser Lys
            180                 185                 190

Ser Val Thr Val Lys Glu Leu Thr Leu Met Asn Ser Pro Glu Phe His
        195                 200                 205

Leu Val Phe Gly Glu Cys Glu Gly Val Lys Ile Gln Gly Leu Lys Ile
    210                 215                 220

Lys Ala Pro Arg Asp Ser Pro Asn Thr Asp Gly Ile Asp Ile Phe Ala
225                 230                 235                 240

Ser Lys Arg Phe His Ile Glu Lys Cys Val Ile Gly Thr Gly Asp Asp
                245                 250                 255

Cys Ile Ala Ile Gly Thr Gly Ser Ser Asn Ile Thr Ile Lys Asp Leu
            260                 265                 270

Ile Cys Gly Pro Gly His Gly Ile Ser Ile Gly Ser Leu Gly Arg Asp
        275                 280                 285

Asn Ser Arg Ala Glu Val Ser His Val His Val Asn Arg Ala Lys Phe
290                 295                 300

Ile Asp Thr Gln Asn Gly Leu Arg Ile Lys Thr Trp Gln Gly Gly Ser
305                 310                 315                 320

Gly Leu Ala Ser Tyr Ile Thr Tyr Glu Asn Val Glu Met Ile Asn Ser
                325                 330                 335

Glu Asn Pro Ile Leu Ile Asn Gln Phe Tyr Cys Thr Ser Ala Ser Ala
            340                 345                 350

Cys Gln Asn Gln Arg Ser Ala Val Gln Ile Gln Gly Val Thr Tyr Lys
        355                 360                 365

Asn Ile His Gly Thr Ser Ala Thr Ala Ala Ala Ile Gln Leu Met Cys
    370                 375                 380

Ser Asp Ser Val Pro Cys Thr Gly Ile Gln Leu Ser Asn Val Ser Leu
385                 390                 395                 400

Lys Leu Thr Ser Gly Lys Pro Ala Ser Cys Val Asp Lys Asn Ala Arg
                405                 410                 415
```

```
Gly Phe Tyr Ser Gly Arg Leu Ile Pro Thr Cys Lys Asn Leu Arg Pro
                420                 425                 430

Gly Pro Ser Pro Lys Glu Phe Glu Leu Gln Gln Gln Pro Thr Thr Val
            435                 440                 445

Met Asp Glu Asn Lys Gly Ala Cys Ala Lys Gly Asp Ser Thr Cys Ile
        450                 455                 460

Ser Leu Ser Ser Pro Pro Asn Cys Lys Asn Lys Cys Lys Gly Cys
465                 470                 475                 480

Gln Pro Cys Lys Pro Lys Leu Ile Ile Val His Pro Asn Lys Pro Gln
                485                 490                 495

Asp Tyr Tyr Pro Gln Lys Trp Val Cys Ser Cys His Asn Lys Ile Tyr
                500                 505                 510

Asn Pro

<210> SEQ ID NO 23
<211> LENGTH: 507
<212> TYPE: PRT
<213> ORGANISM: Juniperus ashei

<400> SEQUENCE: 23

Met Ser Met Lys Phe Met Ala Ala Leu Ala Phe Leu Ala Leu Gln Leu
1               5                   10                  15

Ile Val Met Ala Ala Gly Glu Asp Gln Ser Ala Gln Ile Met Leu Asp
            20                  25                  30

Ser Asp Thr Lys Gln Tyr His Arg Ser Ser Arg Asn Leu Arg Lys Ala
        35                  40                  45

Val His His Ala Arg His Asp Val Ala Ile Val Phe Asn Val Glu His
    50                  55                  60

Tyr Gly Ala Val Gly Asp Gly Lys His Asp Ser Thr Asp Ala Phe Glu
65                  70                  75                  80

Lys Thr Trp Asn Ala Ala Cys Asn Lys Leu Ser Ala Val Phe Leu Val
                85                  90                  95

Pro Ala Asn Lys Lys Phe Val Val Asn Asn Leu Val Phe Tyr Gly Pro
            100                 105                 110

Cys Gln Pro His Phe Ser Phe Lys Val Asp Gly Thr Ile Ala Ala Tyr
        115                 120                 125

Pro Asp Pro Ala Lys Trp Leu Asn Ser Lys Ile Trp Met His Phe Ala
    130                 135                 140

Arg Leu Thr Asp Phe Asn Leu Met Gly Thr Gly Val Ile Asp Gly Gln
145                 150                 155                 160

Gly Asn Arg Trp Trp Ser Asp Gln Cys Lys Thr Ile Asn Gly Arg Thr
                165                 170                 175

Val Cys Asn Asp Lys Gly Arg Pro Thr Ala Ile Lys Ile Asp Phe Ser
            180                 185                 190

Lys Ser Val Thr Val Lys Glu Leu Thr Leu Thr Asn Ser Pro Glu Phe
        195                 200                 205

His Leu Val Phe Gly Glu Cys Asp Gly Val Lys Ile Gln Gly Ile Lys
    210                 215                 220

Ile Lys Ala Pro Arg Asp Ser Pro Asn Thr Asp Gly Ile Asp Ile Phe
225                 230                 235                 240

Ala Ser Lys Arg Phe Glu Ile Glu Lys Cys Thr Ile Gly Thr Gly Asp
                245                 250                 255

Asp Cys Val Ala Val Gly Thr Gly Ser Ser Asn Ile Thr Ile Lys Asp
            260                 265                 270
```

```
Leu Thr Cys Gly Pro Gly His Gly Met Ser Ile Gly Ser Leu Gly Lys
            275                 280                 285

Gly Asn Ser Arg Ser Glu Val Ser Phe Val His Leu Asp Gly Ala Lys
        290                 295                 300

Phe Ile Asp Thr Gln Asn Gly Leu Arg Ile Lys Thr Trp Gln Gly Gly
305                 310                 315                 320

Ser Gly Leu Ala Ser His Ile Thr Tyr Glu Asn Val Glu Met Ile Asn
                325                 330                 335

Ala Glu Asn Pro Ile Leu Ile Asn Gln Phe Tyr Cys Thr Ser Ala Ala
            340                 345                 350

Ala Cys Lys Asn Gln Arg Ser Ala Val Lys Ile Gln Asp Val Thr Phe
        355                 360                 365

Lys Asn Ile His Gly Thr Ser Ala Thr Ala Ala Ile Gln Leu Met
370                 375                 380

Cys Ser Asp Ser Val Pro Cys Ser Asn Ile Lys Leu Ser Asn Val Phe
385                 390                 395                 400

Leu Lys Leu Thr Ser Gly Lys Val Ala Thr Cys Val Asn Lys Asn Ala
                405                 410                 415

Asn Gly Tyr Tyr Thr Asn Pro Leu Asn Pro Ser Cys Lys Ser Leu His
            420                 425                 430

Pro Gly Arg Thr Pro Lys Glu Leu Glu Leu His Gln Lys Pro Thr Thr
        435                 440                 445

Leu Leu Met Asp Glu Lys Met Gly Ala Ser Leu Asn Ser Ser Pro Pro
    450                 455                 460

Asn Cys Lys Asn Lys Cys Lys Gly Cys Gln Pro Cys Lys Pro Lys Leu
465                 470                 475                 480

Ile Ile Val His Pro Asn Gln Pro Glu Asp Tyr Tyr Pro Gln Arg Trp
                485                 490                 495

Val Cys Ser Cys His Asn Lys Ile Tyr Asn Pro
            500                 505

<210> SEQ ID NO 24
<211> LENGTH: 384
<212> TYPE: PRT
<213> ORGANISM: Hexalectris arizonica

<400> SEQUENCE: 24

His Asp Val Ala Ile Val Phe Asn Val Glu His His Gly Ala Val Gly
1               5                   10                  15

Asp Gly Asn His Asp Ser Thr Ala Phe Glu Lys Thr Trp Asn Glu
            20                  25                  30

Ala Cys Lys Thr Leu Ser Ala Val Phe Leu Val Pro Ala Asn Lys Lys
        35                  40                  45

Phe Val Val Asn Asn Leu Val Phe Tyr Gly Pro Cys Gln Pro His
    50                  55                  60

Phe Ser Pro Lys Val Asp Gly Ile Ile Ala Ala Tyr Pro Asp Pro Val
65                  70                  75                  80

Lys Trp Lys Asn Ser Lys Ile Trp Met His Phe Ala Arg Leu Thr Asp
                85                  90                  95

Phe Asn Leu Met Gly Thr Gly Val Ile Asp Gly Gln Gly Ser Lys Trp
            100                 105                 110

Trp Ser Asp Gln Cys Lys Thr Val Asn Gly Arg Thr Val Cys Asn Asp
        115                 120                 125

Lys Gly Arg Pro Thr Ala Ile Lys Ile Asp Phe Ser Lys Ser Val Thr
```

```
                130                 135                 140
Val Lys Glu Leu Thr Leu Met Asn Ser Pro Glu Phe His Leu Val Phe
145                 150                 155                 160

Gly Glu Cys Asp Gly Val Lys Ile Gln Gly Ile Lys Ile Lys Ala Pro
                165                 170                 175

Lys Glu Ser Pro Asn Thr Asp Gly Ile Asp Ile Phe Gly Ser Lys Arg
                180                 185                 190

Phe Glu Ile Glu Lys Cys Ile Ile Gly Thr Gly Asp Asp Cys Val Ala
                195                 200                 205

Ile Gly Thr Gly Ser Ser Asn Ile Thr Ile Thr Asp Leu Thr Cys Gly
                210                 215                 220

Pro Gly His Gly Met Ser Ile Gly Ser Leu Gly Lys Gly Asn Ser Arg
225                 230                 235                 240

Ser Glu Val Ser Phe Val His Leu Asp Gly Ala Lys Phe Ile Asp Thr
                245                 250                 255

Gln Asn Gly Leu Arg Ile Lys Thr Trp Gln Gly Gly Ser Gly Leu Ala
                260                 265                 270

Ser His Ile Thr Tyr Glu Asn Val Glu Met Val Asn Ala Glu Asn Pro
                275                 280                 285

Ile Leu Ile Asn Gln Phe Tyr Cys Thr Ser Ala Ala Cys Glu Asn Gln
                290                 295                 300

Arg Ser Ala Val Lys Ile Glu Asp Val Trp Phe Lys Asn Ile His Gly
305                 310                 315                 320

Thr Ser Ala Thr Ala Ala Ile Gln Leu Met Cys Ser Asp Ser Val
                325                 330                 335

Pro Cys Ser Asn Ile Lys Leu Ser Asn Val Val Leu Lys Leu Ser Ser
                340                 345                 350

Gly Lys Val Ala Ala Cys Val Asn Lys Asn Ala Asn Gly Tyr Tyr Thr
                355                 360                 365

Asn Pro Leu Asn Pro Pro Cys Lys Ser Leu His Pro Gly Pro Thr Pro
                370                 375                 380

<210> SEQ ID NO 25
<211> LENGTH: 225
<212> TYPE: PRT
<213> ORGANISM: Juniperus ashei

<400> SEQUENCE: 25

Met Ala Arg Val Ser Glu Leu Ala Phe Leu Ala Ala Thr Leu Ala
1               5                   10                  15

Ile Ser Leu His Met Gln Glu Ala Gly Val Val Lys Phe Asp Ile Lys
                20                  25                  30

Asn Gln Cys Gly Tyr Thr Val Trp Ala Ala Gly Leu Pro Gly Gly Gly
                35                  40                  45

Lys Arg Leu Asp Gln Gly Gln Thr Trp Thr Val Asn Leu Ala Ala Gly
                50                  55                  60

Thr Ala Ser Ala Arg Phe Trp Gly Arg Thr Gly Cys Thr Phe Asp Ala
65                  70                  75                  80

Ser Gly Lys Gly Ser Cys Gln Thr Gly Asp Cys Gly Gly Gln Leu Ser
                85                  90                  95

Cys Thr Val Ser Gly Ala Val Pro Ala Thr Leu Ala Glu Tyr Thr Gln
                100                 105                 110

Ser Asp Gln Asp Tyr Tyr Asp Val Ser Leu Val Asp Gly Phe Asn Ile
                115                 120                 125
```

```
Pro Leu Ala Ile Asn Pro Thr Asn Ala Gln Cys Thr Ala Pro Ala Cys
    130                 135                 140

Lys Ala Asp Ile Asn Ala Val Cys Pro Ser Glu Leu Lys Val Asp Gly
145                 150                 155                 160

Gly Cys Asn Ser Ala Cys Asn Val Phe Lys Thr Asp Gln Tyr Cys Cys
                165                 170                 175

Arg Asn Ala Tyr Val Asp Asn Cys Pro Ala Thr Asn Tyr Ser Lys Ile
                180                 185                 190

Phe Lys Asn Gln Cys Pro Gln Ala Tyr Ser Tyr Ala Lys Asp Asp Thr
            195                 200                 205

Ala Thr Phe Ala Cys Ala Ser Gly Thr Asp Tyr Ser Ile Val Phe Cys
        210                 215                 220

Pro
225

<210> SEQ ID NO 26
<211> LENGTH: 225
<212> TYPE: PRT
<213> ORGANISM: Juniperus rigida

<400> SEQUENCE: 26

Met Ala Arg Val Ser Glu Leu Ala Leu Leu Val Ala Thr Leu Ala
1               5                   10                  15

Ile Ser Leu His Met Gln Glu Ala Gly Ala Val Lys Phe Asp Ile Lys
                20                  25                  30

Asn Gln Cys Gly Tyr Thr Val Trp Ala Ala Gly Leu Pro Gly Gly Gly
                35                  40                  45

Lys Arg Leu Asp Gln Gly Gln Thr Trp Thr Leu Asn Leu Ala Ala Gly
50                  55                  60

Thr Ala Ser Ala Arg Phe Trp Gly Arg Thr Gly Cys Thr Phe Asp Ala
65                  70                  75                  80

Ser Gly Lys Gly Ser Cys Lys Thr Gly Asp Cys Gly Gly Gln Leu Ser
                85                  90                  95

Cys Thr Val Ser Gly Ala Val Pro Ala Thr Leu Ala Glu Tyr Thr Gln
                100                 105                 110

Ser Asp Gln Asp Tyr Tyr Asp Val Ser Leu Val Asp Gly Phe Asn Ile
            115                 120                 125

Pro Leu Ala Ile Asn Pro Thr Asn Ala Gln Cys Thr Ala Pro Ala Cys
    130                 135                 140

Lys Ala Asp Ile Asn Ala Val Cys Pro Ser Glu Leu Lys Val Glu Gly
145                 150                 155                 160

Gly Cys Asn Ser Ala Cys Asn Val Phe Gln Thr Asp Gln Tyr Cys Cys
                165                 170                 175

Arg Asn Ala Tyr Val Asp Asn Cys Pro Ala Thr Asn Tyr Ser Lys Ile
                180                 185                 190

Phe Lys Asn Gln Cys Pro Gln Ala Tyr Ser Tyr Ala Lys Asp Asp Thr
            195                 200                 205

Ala Thr Phe Ala Cys Ala Ser Gly Thr Asp Tyr Ser Ile Val Phe Cys
        210                 215                 220

Pro
225

<210> SEQ ID NO 27
<211> LENGTH: 224
<212> TYPE: PRT
<213> ORGANISM: Cupressus sempervirens
```

<400> SEQUENCE: 27

Met Ala Arg Val Ser Glu Leu Ala Leu Leu Val Ala Thr Leu Ala
1               5                   10                  15

Ile Ser Leu His Met Gln Glu Ala Gly Ala Val Lys Phe Asp Ile Lys
            20                  25                  30

Asn Gln Cys Gly Tyr Thr Val Trp Ala Ala Gly Leu Pro Gly Gly Gly
        35                  40                  45

Lys Arg Leu Asp Gln Gly Gln Thr Trp Thr Val Asn Leu Ala Ala Gly
50                  55                  60

Thr Ala Ser Ala Arg Phe Trp Gly Arg Thr Gly Cys Thr Phe Asp Ala
65                  70                  75                  80

Ser Gly Lys Gly Ser Cys Arg Ser Gly Asp Cys Gly Gly Gln Leu Ser
                85                  90                  95

Cys Thr Val Ser Gly Ala Val Pro Ala Thr Leu Ala Glu Tyr Thr Gln
            100                 105                 110

Ser Asp Lys Asp Tyr Tyr Asp Val Ser Leu Val Asp Gly Phe Asn Ile
        115                 120                 125

Pro Leu Ala Ile Asn Pro Thr Asn Thr Lys Cys Thr Ala Pro Ala Cys
130                 135                 140

Lys Ala Asp Ile Asn Ala Val Cys Pro Ser Glu Leu Lys Val Asp Gly
145                 150                 155                 160

Gly Cys Asn Ser Ala Cys Asn Val Leu Gln Thr Asp Gln Tyr Cys Cys
                165                 170                 175

Arg Asn Ala Tyr Val Asp Asn Cys Pro Ala Thr Asn Tyr Ser Lys Ile
            180                 185                 190

Phe Lys Asn Gln Cys Pro Gln Ala Tyr Ser Tyr Ala Lys Asp Asp Thr
        195                 200                 205

Ala Thr Phe Ala Cys Ala Ser Gly Thr Asp Tyr Ser Ile Val Phe Cys
210                 215                 220

<210> SEQ ID NO 28
<211> LENGTH: 199
<212> TYPE: PRT
<213> ORGANISM: Hexalectris arizonica

<400> SEQUENCE: 28

Val Lys Phe Asp Ile Lys Asn Gln Cys Gly Tyr Thr Val Trp Ala Ala
1               5                   10                  15

Gly Leu Pro Gly Gly Gly Lys Glu Phe Asp Gln Gly Gln Thr Trp Thr
            20                  25                  30

Val Asn Leu Ala Ala Gly Thr Ala Ser Ala Arg Phe Trp Gly Arg Thr
        35                  40                  45

Gly Cys Thr Phe Asp Ala Ser Gly Lys Gly Ser Cys Arg Ser Gly Asp
    50                  55                  60

Cys Gly Gly Gln Leu Ser Cys Thr Val Ser Gly Ala Val Pro Ala Thr
65                  70                  75                  80

Leu Ala Glu Tyr Thr Gln Ser Asp Gln Asp Tyr Tyr Asp Val Ser Leu
                85                  90                  95

Val Asp Gly Phe Asn Ile Pro Leu Ala Ile Asn Pro Thr Asn Thr Lys
            100                 105                 110

Cys Thr Ala Pro Ala Cys Lys Ala Asp Ile Asn Ala Val Cys Pro Ser
        115                 120                 125

Glu Leu Lys Val Asp Gly Gly Cys Asn Ser Ala Cys Asn Val Leu Gln
130                 135                 140

```
Thr Asp Gln Tyr Cys Cys Arg Asn Ala Tyr Val Asn Asn Cys Pro Ala
145                 150                 155                 160

Thr Asn Tyr Ser Lys Ile Phe Lys Asn Gln Cys Pro Gln Ala Tyr Ser
                165                 170                 175

Tyr Ala Lys Asp Asp Thr Ala Thr Phe Ala Cys Ala Ser Gly Thr Asp
            180                 185                 190

Tyr Ser Ile Val Phe Cys Pro
        195

<210> SEQ ID NO 29
<211> LENGTH: 274
<212> TYPE: PRT
<213> ORGANISM: Pinus monticola

<400> SEQUENCE: 29

Met Gly Asn Ser Ser Gly Asn Ser Leu Met Val Leu Leu Leu Val Leu
1               5                   10                  15

Leu Leu Val Gly Val Thr Val Asn Ala Gln Asn Cys Gly Cys Ala Ser
            20                  25                  30

Gly Leu Cys Cys Ser Gln Tyr Gly Tyr Cys Gly Ser Ser Ser Ala Tyr
        35                  40                  45

Cys Gly Ala Gly Cys Lys Ser Gly Pro Cys Ser Gly Gly Ser Pro
    50                  55                  60

Ser Gly Gly Gly Ser Val Gly Thr Ile Ile Ser Gln Ser Phe Phe
65                  70                  75                  80

Asn Gly Leu Ala Gly Gly Ala Ala Ser Ser Cys Glu Gly Lys Gly Phe
                85                  90                  95

Tyr Thr Tyr Asn Ala Phe Ile Ala Ala Ala Asn Ala Tyr Ser Gly Phe
            100                 105                 110

Gly Thr Thr Gly Ser Ala Asp Val Thr Lys Arg Glu Leu Ala Ala Phe
        115                 120                 125

Leu Ala Asn Val Met His Gly Thr Gly Gly Met Cys Tyr Ile Asn Glu
    130                 135                 140

Arg Thr Pro Pro Met Ile Tyr Cys Met Ser Ser Ala Thr Trp Pro Cys
145                 150                 155                 160

Ala Ser Gly Lys Ser Tyr His Gly Arg Gly Pro Leu Gln Leu Ser Trp
                165                 170                 175

Asn Tyr Asn Tyr Gly Ala Ala Gly Gln Ser Ile Gly Phe Asp Gly Val
            180                 185                 190

Asn Asn Pro Glu Lys Val Gly Gln Asp Ser Thr Ile Ser Phe Lys Thr
        195                 200                 205

Ala Val Trp Phe Trp Met Lys Asn Ser Asn Cys His Ser Ala Ile Thr
    210                 215                 220

Ser Gly Gln Gly Phe Gly Gly Thr Ile Lys Ala Ile Asn Ser Gln Glu
225                 230                 235                 240

Cys Asn Gly Gly Asn Ser Gly Glu Val Asn Ser Arg Val Asn Tyr Tyr
                245                 250                 255

Lys Asn Ile Cys Ser Gln Leu Gly Val Asp Pro Gly Ala Asn Leu Ser
            260                 265                 270

Cys His

<210> SEQ ID NO 30
<211> LENGTH: 277
<212> TYPE: PRT
<213> ORGANISM: Pseudotsuga menziesii
```

-continued

<400> SEQUENCE: 30

```
Met Gly Lys Thr Gly Gly Glu Lys Trp Val Met Ala Leu Val Leu Val
1               5                   10                  15

Leu Leu Leu Leu Gly Val Ser Val Asn Ala Gln Asn Cys Gly Cys Ala
            20                  25                  30

Ser Gly Leu Cys Cys Ser Lys Tyr Gly Tyr Cys Gly Thr Thr Ser Ala
        35                  40                  45

Tyr Cys Gly Thr Gly Cys Arg Ser Gly Pro Cys Ser Ser Asn Ser Gly
50                  55                  60

Gly Gly Ser Pro Ser Gly Gly Gly Ser Val Gly Thr Ile Ile Ser
65                  70                  75                  80

Gln Ser Ile Phe Asn Gly Leu Ala Gly Ala Ala Ser Ser Cys Glu
            85                  90                  95

Gly Lys Gly Phe Tyr Thr Tyr Thr Ala Phe Ile Lys Ala Ala Ser Ala
        100                 105                 110

Tyr Ser Gly Phe Gly Thr Thr Gly Ser Asn Asp Val Lys Lys Arg Glu
    115                 120                 125

Leu Ala Ala Phe Phe Ala Asn Val Met His Glu Thr Gly Gly Leu Cys
130                 135                 140

Tyr Ile Asn Glu Arg Asn Pro Pro Met Ile Tyr Cys Asn Ser Ser Ser
145                 150                 155                 160

Thr Trp Pro Cys Ala Ser Gly Lys Ser Tyr His Gly Arg Gly Pro Leu
                165                 170                 175

Gln Leu Ser Trp Asn Tyr Asn Tyr Gly Ala Ala Gly Lys Ser Ile Gly
            180                 185                 190

Phe Asp Gly Leu Asn Asn Pro Glu Lys Val Gly Gln Asp Ala Thr Ile
        195                 200                 205

Ser Phe Lys Thr Ala Val Trp Phe Trp Met Asn Asn Ser Asn Cys His
210                 215                 220

Ser Ala Ile Thr Gly Gly Gln Gly Phe Gly Ala Thr Ile Lys Ala Ile
225                 230                 235                 240

Asn Ser Gly Glu Cys Asn Gly Gly Asn Ser Gly Glu Val Ser Ser Arg
                245                 250                 255

Val Asn Tyr Tyr Arg Lys Ile Cys Ser Gln Leu Gly Val Asp Pro Gly
            260                 265                 270

Ala Asn Val Ser Cys
        275
```

<210> SEQ ID NO 31
<211> LENGTH: 308
<212> TYPE: PRT
<213> ORGANISM: Pinus taeda

<400> SEQUENCE: 31

```
Met Gly Ser Arg Ser Arg Ile Leu Leu Ile Gly Ala Thr Gly Tyr Ile
1               5                   10                  15

Gly Arg His Val Ala Lys Ala Ser Leu Asp Leu Gly His Pro Thr Phe
            20                  25                  30

Leu Leu Val Arg Glu Ser Thr Ala Ser Ser Asn Ser Glu Lys Ala Gln
        35                  40                  45

Leu Leu Glu Ser Phe Lys Ala Ser Gly Ala Asn Ile Val His Gly Ser
    50                  55                  60

Ile Asp Asp His Ala Ser Leu Val Glu Ala Val Lys Asn Val Asp Val
65                  70                  75                  80
```

Val Ile Ser Thr Val Gly Ser Leu Gln Ile Glu Ser Gln Val Asn Ile
             85                  90                  95

Ile Lys Ala Ile Lys Glu Val Gly Thr Val Lys Arg Phe Phe Pro Ser
            100                 105                 110

Glu Phe Gly Asn Asp Val Asp Asn Val His Ala Val Glu Pro Ala Lys
            115                 120                 125

Ser Val Phe Glu Val Lys Ala Lys Val Arg Arg Ala Ile Glu Ala Glu
130                 135                 140

Gly Ile Pro Tyr Thr Tyr Val Ser Ser Asn Cys Phe Ala Gly Tyr Phe
145                 150                 155                 160

Leu Arg Ser Leu Ala Gln Ala Gly Leu Thr Ala Pro Pro Arg Asp Lys
                165                 170                 175

Val Val Ile Leu Gly Asp Gly Asn Ala Arg Val Val Phe Val Lys Glu
            180                 185                 190

Glu Asp Ile Gly Thr Phe Thr Ile Lys Ala Val Asp Asp Pro Arg Thr
            195                 200                 205

Leu Asn Lys Thr Leu Tyr Leu Arg Leu Pro Ala Asn Thr Leu Ser Leu
210                 215                 220

Asn Glu Leu Val Ala Leu Trp Glu Lys Lys Ile Asp Lys Thr Leu Glu
225                 230                 235                 240

Lys Ala Tyr Val Pro Glu Glu Glu Val Leu Lys Leu Ile Ala Asp Thr
                245                 250                 255

Pro Phe Pro Ala Asn Ile Ser Ile Ala Ile Ser His Ser Ile Phe Val
                260                 265                 270

Lys Gly Asp Gln Thr Asn Phe Glu Ile Gly Pro Ala Gly Val Glu Ala
                275                 280                 285

Ser Gln Leu Tyr Pro Asp Val Lys Tyr Thr Thr Val Asp Glu Tyr Leu
290                 295                 300

Ser Asn Phe Val
305

<210> SEQ ID NO 32
<211> LENGTH: 173
<212> TYPE: PRT
<213> ORGANISM: Picea abies

<400> SEQUENCE: 32

Met Asp Ser Arg Arg Leu Lys Arg Ser Gly Ile Val Cys Met Val Leu
1               5                   10                  15

Met Ser Met Leu Met Leu Val Val Cys Glu Asp Ser Asp Asn Thr Ala
                20                  25                  30

Cys Leu Ser Ser Leu Ser Ser Cys Ala Pro Tyr Leu Asn Ala Thr Thr
            35                  40                  45

Lys Pro Asp Ser Ser Cys Cys Ser Ala Leu Ile Ser Val Ile Asp Lys
    50                  55                  60

Asp Ser Gln Cys Leu Cys Asn Leu Leu Asn Ser Asp Thr Val Lys Gln
65                  70                  75                  80

Leu Gly Val Asn Val Thr Gln Ala Met Lys Met Pro Ala Glu Cys Gly
                85                  90                  95

Lys Asn Val Ser Ala Thr Gln Cys Asn Lys Thr Ala Thr Ser Gly Gly
            100                 105                 110

Ser Ser Val Gly Lys Thr Pro Thr Ser Thr Pro Pro Ser Ser Ala
            115                 120                 125

Thr Pro Ser Thr Thr Thr Ile Thr Lys Ser Asn Ser Asn Ala Ala Ala

```
            130                 135                 140
Ser Val Ser Val Lys Met Phe Pro Val Ala Ala Leu Val Phe Val Ala
145                 150                 155                 160

Val Ala Ser Val Leu Gly Leu Lys Gly Pro Cys Leu Arg
                165                 170
```

NUCLEIC ACIDS FOR TREATMENT OF ALLERGIES

CROSS-REFERENCE TO RELATED APPLICATIONS

This application is a divisional application of U.S. application Ser. No. 14/407,410, filed on May 6, 2015, which is a national stage of International Application No. PCT/US2012/042552, filed on Jun. 15, 2012. Both documents are hereby incorporated by reference in their entirety.

BACKGROUND OF THE INVENTION

Field of the Invention

The present invention relates to the fields of molecular biology and medicine. More specifically, the invention relates to nucleic acids for use as DNA vaccines, and methods of using them to treat subjects suffering from or susceptible to allergic reactions.

Discussion of Related Art

Allergy is a hypersensitivity disease characterized by the production of IgE antibodies against an allergen, or allergy-causing molecule. Allergies affect more than 25% of the population. Allergens can enter the body through many routes, including the respiratory tract, skin contact, ingestion, insect bite, or injection of a drug.

Allergy disease management comprises diagnosis and treatment. Allergists diagnose an allergy using a variety of techniques, such as a skin prick test, radioallergosorbent-based techniques, ELISA, or provocation test to demonstrate allergen specific IgE and to identify the allergen source. Treatment of allergy most often falls into two categories: avoidance and dosing with anti-histamines. A third alternative, allergy immunotherapy, requires that the patient receive weekly injections consisting of small amounts of the offending allergens in order to help the immune system reeducate its response to the allergen.

The use and generation of allergen fusion proteins are well known in the art. For example, U.S. Pat. No. 7,566,456 teaches a fusion protein with IgE and IgG binding domains as well as encoding an allergen. Further, WO 97/07218 teaches allergen-anti-CD32 fusion proteins for use in allergy immunotherapy. Neither of these documents, however, teaches how their respective fusion protein interacts with T cells through antigen presentation to induce or modify a Th1 response. Furthermore, there is no theoretical connection between directing the anti-CD32 containing vaccine to dendritic cells to effect a positive induction of Th1 cells. Both of these documents teach a composition that introduces an allergen therapeutically, such that the allergen can be found in the serum as an allergen-fusion protein.

It has been established by Toda et al., 2002 that a T cell epitope of an allergen, in this case a Cry J2 epitope located at amino acid 247-258, can be attached to a fusion protein and be used to conduct allergy-specific immunotherapy. The specific composition described by Toda et al., 2002 is the use of a DNA vaccine encoding the major CD4 T cell epitope of Cry J2, located at amino acids 247-258, attached to class II-associated invariant chain peptide (CLIP). CLIP contains a lysosomal/endosomal trafficking sequence and contains a domain that binds to the peptide binding groove of MHC II. Toda et al., 2002 shows that immunization with the Cry J2 peptide/CLIP DNA vaccine results in priming a mouse to a predominantly Th1 response, characterized by higher IFN-gamma and IgG2a production. However, Toda et al. does not teach the intracellular targeting of the entire protein coding sequence of an allergen useful for conducting allergy-specific immunotherapy.

U.S. Pat. No. 6,982,326 and U.S. Pat. No. 6,090,386 describe nucleic acid sequences coding for the *Cryptomeria japonica* major pollen allergens Cry J1, Cry J2, Jun s I, and Jun v I, and fragments or peptides thereof. The invention also provides purified Cry J1, Cry J2, Jun s I, and Jun v I, and at least one fragment thereof produced in a host cell transformed with a nucleic acid sequence coding for Cry J1, Cry J2, Jun s I, and Jun v I, or at least one fragment thereof, and fragments of Cry J1, Cry J2, Jun s I, or Jun v I, or at least one fragment thereof, and fragments of Cry J1, Cry J2, Jun s I, or Jun v I prepared synthetically. Cry J1, Cry J2, Jun s I, and Jun v I, and fragments thereof are disclosed as useful for diagnosing, treating, and preventing Japanese cedar pollinosis. The invention also provides isolated peptides of Cry J1 and Cry J2. Peptides within the scope of the invention comprise at least one T cell epitope, or preferably at least two T cell epitopes of Cry J1 or Cry J2. The invention also pertains to modified peptides having similar or enhanced therapeutic properties as the corresponding naturally-occurring allergen or portion thereof but having reduced side effects. Methods of treatment or of diagnosis of sensitivity to Japanese cedar pollens in an individual and therapeutic compositions, and multi-peptide formulations comprising one or more peptides of the invention are also provided. The invention does not teach how to combine the epitopes or allergens into a DNA vaccine with immunostimulatory properties.

U.S. Pat. No. 7,547,440 and U.S. Pat. No. 7,112,329 identify the T-cell epitope site on a Japanese cypress (hinoki) pollen allergen molecule by stimulating a T-cell line established from a patient suffering from Japanese cypress pollen allergy with an overlap peptide covering the primary structure of the Japanese cypress pollen allergen. The peptide is useful in peptide-based immunotherapy for patients with spring tree pollinosis including patients with Japanese cypress pollinosis having cross reactivity with Japanese cypress pollen. The peptide is also useful for diagnosing spring tree pollinosis. The invention is limited to diagnostics and polypeptide delivery of epitopes.

DNA vaccines have been developed as an alternative to traditional whole cell or whole virus vaccines. Generally speaking, DNA vaccines are engineered nucleic acids that include sequences encoding one or more epitopes. The nucleic acids are delivered to cells, typically antigen presenting cells (APCs), the nucleic acids are expressed, and the epitopes present on the expressed proteins are processed in the endosomal/lysosomal compartment, and ultimately presented on the surface of the cell. U.S. Pat. No. 5,633,234 to August et al. discloses and characterizes the endosomal/lysosomal targeting sequence of the lysosomal-associated membrane protein (LAMP). This patent identifies critical residues in the C-terminal region of the protein, which are necessary for targeting of the protein to the endosomal/lysosomal compartment. The patent discloses that fusion of antigenic peptides to the C-terminal LAMP targeting sequence can provide enhanced processing and presentation of epitopes for generation of an immune response.

In addition, U.S. patent application publication number 2004/0157307 to Harris et al. discloses the use of the LAMP lumenal domain as a "trafficking domain" to direct chimeric proteins expressed from DNA vaccines through one or more cellular compartments/organelles, such as through the lysosomal vesicular pathway. The chimeric proteins include the lumenal domain of a LAMP polypeptide, an antigenic domain comprising a peptide epitope sequence previously identified and selected from an antigen protein, a transmembrane domain, and an endosomal/lysosomal targeting sequence.

DNA vaccines have been proposed as a treatment of allergic disease (Raz et al., 1996; Hartl et al., 2004; Hsu et al., 1996; Crameri 2007; Weiss et al., 2006). The underlying rationale is that allergen protein encoded by a DNA vaccine will preferentially activate the allergen-specific Th1 cellular response with the production of interferons by APCs, natural killer (NK), and T cells, rather than the characteristic Th2-type response, such as secretion of IL-4, IL-5, and IL-13, and the formation of IgE by B lymphocytes and the maturation and recruitment of eosinophils in late-phase reactions. However, the mechanisms underlying the differential induction of the Th1 and Th2 T-cell phenotypes appear to involve a large number of factors, such as unique properties of the bacterial DNA of vaccine preparations, e.g., unmethylated and CpG DNA residues, the cytokine milieu elicited by innate immunity, and the cellular trafficking properties of the allergens (Chen et al., 2001; Kaech et al., 2002). No invention or method has successfully addressed the uncertainty of allergy treatment as conducted by delivery of nucleic acids encoding an allergen. Thus, to date such a method of allergy treatment has not been enabled. In addition, administration of DNA vaccines for the treatment of allergic disease has resulted in the secretion of the allergen peptide into the extracellular environment, potentially leading to accidental induction of an allergic response through activation of IgE.

SUMMARY OF THE INVENTION

The present invention provides nucleic acids (also referred to herein as "constructs") that encode allergenic proteins, allergenic polypeptides, and allergenic peptides. The nucleic acids are designed for delivery to immune cells and production of allergenic proteins, polypeptides, and peptides within those cells. The encoded proteins, polypeptides, and peptides have targeting sequences for targeting of the proteins to the MHC-II compartment for processing and display of one or more epitopes, resulting in an immune response to the epitope(s). In general, the nucleic acids comprise the following domains, which correlate to the respective domains of the encoded protein: a signal sequence domain; an intra-organelle stabilizing domain; an allergen domain; a transmembrane domain; and a cytoplasmic lysosome/endosome targeting domain.

Within the context of the encoded protein, the signal sequence is provided to direct the encoded protein to the endoplasmic reticulum or a lysosome. The intra-organelle stabilizing domain is a sequence that is designed to be proteolytically resistant and to protect the remaining portions of the protein, and in particular the allergen domain, from degradation prior to processing for epitope presentation by the cell. In exemplary embodiments, the intra-organelle stabilizing domain is the lumenal domain of LAMP-1. The allergen domain comprises the sequence of one or more allergenic epitopes that can serve to raise an immune response in an animal in which the epitopes are presented. Typically, the allergen domain comprises one or more allergen proteins, although in embodiments, immunogenic polypeptide or peptide fragments of allergenic proteins can be used. In exemplary embodiments discussed below, the epitope is an epitope of a plant allergen. In the encoded proteins of the invention, the allergen domain does not include a signal peptide, such as the signal peptide(s) naturally occurring as part of the allergen protein(s). The allergen domain can comprise a single allergenic protein, polypeptide, or peptide, or can comprise two or more allergenic proteins, polypeptides, or peptides. Where two or more allergens are present, each allergen can be from the same species/source or one or more can be from one or more different sources. Where two or more allergens are present, they are coordinately expressed to provide an equal number of copies of each coding region in the expressed protein. The transmembrane domain can be any sequence that is suitable for directing insertion and transfer of a protein through a membrane. Many such sequences are known in the art or can be easily designed. The lysosome/endosome targeting domain can be any sequence that is capable of directing the peptide to a lysosome or endosome. Such sequences are known in the art and are exemplified herein by the cytoplasmic tail sequence of LAMP-1.

As mentioned above, in preferred embodiments, the nucleic acids comprise an allergen domain that includes the entire allergenic coding sequence for an allergenic protein, but lacks the coding sequence for the allergen's signal sequence. In some embodiments, the nucleic acids of the invention do not comprise the entire allergenic coding sequence, but instead comprise only a sufficient amount of the coding sequence such that the encoded polypeptide, when expressed, is able to fold to achieve the natural three dimensional structure of at least one epitope present on the polypeptide. As in constructs comprising an entire allergen coding sequence, where less than the entire coding sequence is present, the nucleic acids construct also lacks the coding sequence for a naturally-occurring signal peptide for the allergenic polypeptide or peptide.

In preferred embodiments, the nucleic acid construct comprises the coding sequences for multiple allergenic proteins, polypeptides, and/or peptides in the allergen domain. Each allergen present can be from the same source, each from a different source, or any combination thereof.

The nucleic acids, and thus the encoded proteins, polypeptides, and peptides of the invention can be used in methods of treating subjects, and in particular animal subjects suffering from or potentially developing allergies. In general, a method of treating according to the present invention comprises administering a nucleic acid of the invention to a subject in an amount sufficient to deliver the nucleic acid to one or more immune cells, and preferably to one or more antigen presenting cells (APC) of the immune system. Once delivered, the nucleic acid is expressed, the encoded protein processed inside the cell, and the epitope(s) displayed on the surface of the cell. The method of treating can be considered a method of using the nucleic acids and proteins to provide a therapeutic or prophylactic immune response.

BRIEF DESCRIPTION OF THE DRAWINGS

FIG. 9A shows expression of the CryJ1-CryJ2 combined allergens (see FIG. 5) and the CryJ2 allergen alone (see FIG. 2) in constructs according to the invention, when assayed with anti-Cry J2 antibodies. FIG. 9B shows expression of the CryJ1-CryJ2 combined allergens and the CryJ1 allergen (lacking its native signal sequence; see FIG. 7), when assayed with anti-CryJ1 antibodies. FIG. 9B further shows that expression of the CryJ1 allergen is not detectable in a construct in which the natural signal sequence for the CryJ1 allergen is not removed (vector map not shown).

FIG. 10A shows that a significant increase in IgG1 production and detection is seen as a result of administration of the CryJ2-LAMP construct of the invention (see FIG. 2) as compared to a construct comprising a plasmid backbone fused to the CryJ2 coding sequence (see FIG. 8). FIG. 10B shows that a significant increase in IgG2a production and detection is seen as a result of administration of the CryJ2-LAMP construct of the invention (as per FIG. 10A) as compared to a construct comprising a plasmid backbone fused to the CryJ2 coding sequence (as per FIG. 10A).

FIG. 11A depicts IgG2a detection at 21 days and 28 days post injection of the DNA vaccine at various amounts ranging from 10 ug to 100 ug, as compared to injection of vector DNA alone. FIG. 11B depicts IgG1 detection at 21 days and 28 days post injection of the DNA vaccine at various amounts ranging from 10 ug to 100 ug, as compared to injection of vector DNA alone.

FIG. 12A shows the effect of IL-4. FIG. 12B shows the effect of IFN-gamma.

FIG. 13A shows IgG1 titers over time. FIG. 13B shows IgG2a titers over time.

DETAILED DESCRIPTION OF EXEMPLARY EMBODIMENTS

Figure 1:
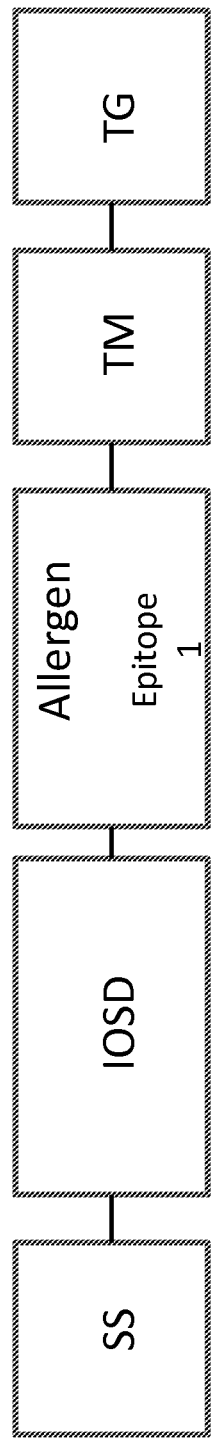
FIG. 1 is a schematic representation of a nucleic acid according to one embodiment of the invention in which a single antigen comprising a single epitope is provided in the allergen domain.

Reference will now be made in detail to various exemplary embodiments of the invention. It is to be understood that the following discussion of exemplary embodiments is not intended as a limitation on the invention, as broadly disclosed herein. Rather, the following discussion is provided to give the reader a more detailed understanding of certain aspects and features of the invention. The practice of the present invention employs, unless otherwise indicated, conventional molecular biology, microbiology, and recombinant DNA techniques within the skill of those in the art. Such techniques are explained fully in the literature known to the ordinary artisan in these fields, and thus need not be detailed herein. Likewise, practice of the invention for medical treatment follows standard protocols known in the art, and those protocols need not be detailed herein.

Before embodiments of the present invention are described in detail, it is to be understood that the terminology used herein is for the purpose of describing particular embodiments only, and is not intended to be limiting. Further, where a range of values is provided, it is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included in the invention. It is thus to be understood that, where a range of values is presented, each value within that range, and each range falling within that range, is inherently recited as well, and that the avoidance of a specific recitation of each and every value and each and every possible range of values is not an omission of those values and ranges, but instead is a convenience for the reader and for brevity of this disclosure.

Unless defined otherwise, all technical and scientific terms used herein have the same meaning as commonly understood by one of ordinary skill in the art to which the term belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited. The present disclosure is controlling to the extent it conflicts with any incorporated publication.

As used herein and in the appended claims, the singular forms "a", "an", and "the" include plural referents unless the context clearly dictates otherwise. Thus, for example, reference to "an allergen" includes a plurality of such allergens and reference to "the sample" includes reference to one or more samples and equivalents thereof known to those skilled in the art, and so forth. Furthermore, the use of terms that can be described using equivalent terms include the use of those equivalent terms. Thus, for example, the use of the term "subject" is to be understood to include the terms "animal", "human", and other terms used in the art to indicate one who is subject to a medical treatment.

As used herein, the term "comprising" is intended to mean that the constructs, compositions, and methods include the recited elements and/or steps, but do not exclude other elements and/or steps. "Consisting essentially of, when used to define constructs, compositions, and methods, means excluding other elements and steps of any essential significance to the recited constructs, compositions, and methods. Thus, a composition consisting essentially of the elements as defined herein would not exclude trace contaminants from the isolation and purification method and pharmaceutically acceptable carriers, such as phosphate buffered saline, preservatives, and the like. "Consisting of means excluding more than trace elements of other ingredients and substantial method steps for administering the compositions of this invention. Embodiments defined by each of these transition terms are within the scope of this invention.

A "chimeric DNA" is an identifiable segment of DNA within a larger DNA molecule that is not found in association with the larger molecule in nature. Thus, when the chimeric DNA encodes a protein segment, the segment coding sequence will be flanked by DNA that does not flank the coding sequence in any naturally occurring genome. In the case where the flanking DNA encodes a polypeptide sequence, the encoded protein is referred to as a "chimeric protein" (i.e., one having non-naturally occurring amino acid sequences fused together). Allelic variations or naturally occurring mutational events do not give rise to a chimeric DNA or chimeric protein as defined herein.

As used herein, the terms "polynucleotide" and "nucleic acid molecule" are used interchangeably to refer to polymeric forms of nucleotides of any length. The polynucleotides may contain deoxyribonucleotides, ribonucleotides, and/or their analogs. Nucleotides may have any three-dimensional structure, and may perform any function, known or unknown. The term "polynucleotide" includes, for example, single-, double-stranded and triple helical molecules, a gene or gene fragment, exons, introns, mRNA, tRNA, rRNA, ribozymes, antisense molecules, cDNA, recombinant polynucleotides, branched polynucleotides, aptamers, plasmids, vectors, isolated DNA of any sequence, isolated RNA of any sequence, nucleic acid probes, and primers. A nucleic acid molecule may also comprise modified nucleic acid molecules (e.g., comprising modified bases, sugars, and/or internucleotide linkers).

As used herein, the term "peptide" refers to a compound of two or more subunit amino acids, amino acid analogs, or peptidomimetics. The subunits may be linked by peptide bonds or by other bonds (e.g., as esters, ethers, and the like). The term "peptide" is used herein generically to refer to peptides (i.e., polyamino acids of from 2 to about 20 residues), polypeptides (i.e., peptides of from about 20 residues to about 100 residues), and proteins (i.e., peptides having about 100 or more residues).

As used herein, the term "amino acid" refers to either natural and/or unnatural or synthetic amino acids, including glycine and both D or L optical isomers, and amino acid analogs and peptidomimetics. A peptide of three or more amino acids is commonly called an oligopeptide if the peptide chain is short. While the term "protein" encompasses the term "polypeptide", a "polypeptide" may be a less than a full-length protein.

The term "allergen" refers to any naturally occurring protein or mixtures of proteins that have been reported to induce allergic, i.e., IgE mediated reactions upon their repeated exposure to an individual. An allergen is any compound, substance, or material that is capable of evoking an allergic reaction. Allergens are usually understood as a subcategory of antigens, which are compounds, substances, or materials capable of evoking an immune response. For carrying out the invention, the allergen may be selected, among other things, from natural or native allergens, modified natural allergens, synthetic allergens, recombinant allergens, allergoids, and mixtures or combinations thereof. Of particular interest are allergens that are capable of causing an IgE-mediated immediate type hypersensitivity.

Examples of naturally occurring allergens include pollen allergens (e.g., tree, weed, herb and grass pollen allergens), mite allergens (from e.g. house dust mites and storage mites), insect allergens (e.g., inhalant, saliva- and venom origin allergens), animal allergens from e.g. saliva, hair and dander from animals (e.g. dog, cat, horse, rat, mouse, etc.), fungi allergens and food allergens. The allergen may be in the form of an allergen extract, a purified allergen, a modified allergen or a recombinant allergen or a recombinant mutant allergen, an allergen fragment above 30 amino acids or any combination thereof.

In terms of their chemical or biochemical nature, allergens can represent native or recombinant proteins or peptides, fragments or truncated versions of native or recombinant proteins or peptides, fusion proteins, synthetic compounds (chemical allergens), synthetic compounds that mimic an allergen, or chemically or physically altered allergens, such as allergens modified by heat denaturation.

The classification of an allergen as a major allergen can be subject to several tests. An allergen is commonly classified as a major allergen if at least 25% of patients show strong IgE binding (score 3) and at least moderate binding (score 2) from 50% of the patients, the binding being determined by an CRIE (Crossed Radio Immune Electrophoresis) (CRIE Strong binding, i.e., visible IgE-binding on an X-ray film after one day; CRIE Moderate binding, i.e., binding after 3 days; CRIE Weak binding, i.e., binding after 10 days). Strong IgE binding from at least 10% of the patients classifies the allergen as an Intermediate allergen and clearly specific binding from less than 10% of the patients classifies it as a Minor allergen. Other methods may also be used in determining the IgE binding of for instance IgE-blots.

An "epitope" is a structure, usually made up of a short peptide sequence or oligosaccharide, that is specifically recognized or specifically bound by a component of the immune system. T-cell epitopes have generally been shown to be linear oligopeptides. Two epitopes correspond to each other if they can be specifically bound by the same antibody. Two epitopes correspond to each other if both are capable of binding to the same B cell receptor or to the same T cell receptor, and binding of one antibody to its epitope substantially prevents binding by the other epitope (e.g., less than about 30%, preferably, less than about 20%, and more preferably, less than about 10%, 5%, 1%, or about 0.1% of the other epitope binds).

As used herein, two nucleic acid coding sequences "correspond" to each other if the sequences or their complementary sequences encode the same amino acid sequences.

As used herein, a polynucleotide or polynucleotide region (or a polypeptide or polypeptide region) which has a certain percentage (for example, at least about 50%, at least about 60%), at least about 70%, at least about 80%, at least about 85%, at least about 90%, at least about 95%, at least about 99%) of "sequence identity" to another sequence means that, when maximally aligned, manually or using software programs routine in the art, that percentage of bases (or amino acids) are the same in comparing the two sequences.

Two nucleotide sequences are "substantially homologous" or "substantially similar" when at least about 50%, at least about 60%, at least about 70%, at least about 75%, and preferably at least about 80%, and most preferably at least about 90 or 95% of the nucleotides match over the defined length of the DNA sequences. Similarly, two polypeptide sequences are "substantially homologous" or "substantially similar" when at least about 40%, at least about 50%), at least about 60%, at least about 66%, at least about 70%, at least about 75%, and preferably at least about 80%, and most preferably at least about 90 or 95% or 98% of the amino acid residues of the polypeptide match over a defined length of the polypeptide sequence. Sequences that are substantially homologous can be identified by comparing the sequences using standard software available in sequence data banks. Substantially homologous nucleic acid sequences also can be identified in a Southern hybridization experiment under, for example, stringent conditions as defined for that particular system. Defining appropriate hybridization conditions is within the skill of the art. For example, stringent conditions can be: hybridization at 5×SSC and 50% formamide at 42° C., and washing at 0.1×SSC and 0.1% sodium dodecyl sulfate at 60° C.

"Conservatively modified variants" of domain sequences also can be provided. With respect to particular nucleic acid sequences, the term conservatively modified variants refers to those nucleic acids that encode identical or essentially identical amino acid sequences, or where the nucleic acid does not encode an amino acid sequence, to essentially identical sequences. Specifically, degenerate codon substitutions can be achieved by generating sequences in which the third position of one or more selected (or all) codons is substituted with mixed-base and/or deoxyinosine residues (Batzer, et al., 1991, Nucleic Acid Res. 19: 5081; Ohtsuka, et al., 1985, J. Biol. Chem. 260: 2605-2608; Rossolini et al., 1994, Mol. Cell. Probes 8: 91-98).

The term "biologically active fragment", "biologically active form", "biologically active equivalent", and "functional derivative" of a wild-type protein, means a substance that possesses a biological activity that is at least substantially equal (e.g., not significantly different from) the biological activity of the wild type protein as measured using an assay suitable for detecting the activity. For example, a biologically active fragment comprising a trafficking domain is one which can co-localize to the same compartment as a full length polypeptide comprising the trafficking domain.

A cell has been "transformed", "transduced", or "transfected" by exogenous or heterologous nucleic acids when such nucleic acids have been introduced inside the cell. Transforming DNA may or may not be integrated (covalently linked) with chromosomal DNA making up the genome of the cell. In prokaryotes, yeast, and mammalian cells for example, the transforming DNA may be maintained on an episomal element, such as a plasmid. In a eukaryotic cell, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations (e.g., at least about 10).

A "replicon" is any genetic element (e.g., plasmid, chromosome, virus) that functions as an autonomous unit of DNA replication in vivo.

As used herein, a "viral vector" refers to a virus or viral particle that comprises a polynucleotide to be delivered into a host cell, either in vivo, ex vivo, or in vitro. Examples of viral vectors include, but are not limited to, adenovirus vectors, adeno-associated virus vectors, retroviral vectors, and the like. In aspects where gene transfer is mediated by an adenoviral vector, a vector construct refers to the polynucleotide comprising the adenovirus genome or part thereof, and a selected, non-adeno viral gene, in association with adenoviral capsid proteins.

As used herein, a "nucleic acid delivery vector" is a nucleic acid molecule that can transport a polynucleotide of interest into a cell. Preferably, such a vector comprises a coding sequence operably linked to an expression control sequence. However, a polynucleotide sequence of interest does not necessarily comprise a coding sequence. For example, in one aspect, a polynucleotide sequence of interest is an aptamer which binds to a target molecule. In another aspect, the sequence of interest is a complementary sequence of a regulatory sequence that binds to a regulatory sequence to inhibit regulation of the regulatory sequence. In still another aspect, the sequence of interest is itself a regulatory sequence (e.g., for titrating out regulatory factors in a cell).

As used herein, a "nucleic acid delivery vehicle" is defined as any molecule or group of molecules or macromolecules that can carry inserted polynucleotides into a host cell (e.g., such as genes or gene fragments, antisense molecules, ribozymes, aptamers, and the like) and that occurs in association with a nucleic acid delivery vector as described above.

As used herein, "nucleic acid delivery" or "nucleic acid transfer" refers to the introduction of an exogenous polynucleotide (e.g., such as a transgene) into a host cell, irrespective of the method used for the introduction. The introduced polynucleotide may be stably or transiently maintained in the host cell. Stable maintenance typically requires that the introduced polynucleotide either contains an origin of replication compatible with the host cell or integrates into a replicon of the host cell such as an extra-chromosomal replicon (e.g., a plasmid) or a nuclear or mitochondrial chromosome.

As used herein, "expression" refers to the process by which polynucleotides are transcribed into mRNA and/or translated into peptides, polypeptides, or proteins. If the polynucleotide is derived from genomic DNA, expression may include splicing of the mRNA transcribed from the genomic DNA.

As used herein, "under transcriptional control" or "operably linked" refers to expression (e.g., transcription or translation) of a polynucleotide sequence which is controlled by an appropriate juxtaposition of an expression control element and a coding sequence. In one aspect, a DNA sequence is "operatively linked" to an expression control sequence when the expression control sequence controls and regulates the transcription of that DNA sequence.

As used herein, "coding sequence" is a sequence which is transcribed and translated into a polypeptide when placed under the control of appropriate expression control sequences. The boundaries of a coding sequence are determined by a start codon at the 5' (amino) terminus and a translation stop codon at the 3' (carboxyl) terminus. A coding sequence can include, but is not limited to, a prokaryotic sequence, cDNA from eukaryotic mRNA, a genomic DNA sequence from eukaryotic (e.g., mammalian) DNA, and even synthetic DNA sequences. A polyadenylation signal and transcription termination sequence will usually be located 3' to the coding sequence.

As used herein, a "genetic modification" refers to any addition to or deletion or disruption of a cell's normal nucleotide sequence. Any method that can achieve the genetic modification of APCs are within the spirit and scope of this invention. Art recognized methods include viral mediated gene transfer, liposome mediated transfer, transformation, transfection and transduction, e.g., viral-mediated gene transfer such as the use of vectors based on DNA viruses such as adenovirus, adeno-associated virus and herpes virus, as well as retroviral based vectors.

As used herein, "the lysosomal/endosomal compartment" refers to membrane-bound acidic vacuoles containing LAMP molecules in the membrane, hydrolytic enzymes that function in antigen processing, and MHC class II molecules for antigen recognition and presentation. This compartment functions as a site for degradation of foreign materials internalized from the cell surface by any of a variety of mechanisms including endocytosis, phagocytosis, and pinocytosis, and of intracellular material delivered to this compartment by specialized autolytic phenomena (see, for example, de Duve, Eur. J. Biochem. 137: 391, 1983). The term "endosome" as used herein encompasses a lysosome.

As used herein, a "lysosome-related organelle" refers to any organelle that comprises lysozymes and includes, but is not limited to, MIIC, CUV, melanosomes, secretory granules, lytic granules, platelet-dense granules, basophil granules, Birbeck granules, phagolysosomes, secretory lysosomes, and the like. Preferably, such an organelle lacks mannose 6-phosphate receptors and comprises LAMP, but might or might not comprise an MHC class II molecule. For reviews, see, e.g., Blott and Griffiths, Nature Reviews, Molecular Cell Biology, 2002; DellAngelica, et al., The FASEB Journal 14: 1265-1278, 2000.

As used herein a "LAMP polypeptide" refers to LAMP-1, LAMP-2, CD63/LAMP-3, DC-LAMP, or any lysosomal associated membrane protein, or homologs, orthologs, variants (e.g., allelic variants) and modified forms (e.g., comprising one or more mutations, either naturally occurring or engineered). In one aspect, a LAMP polypeptide is a mammalian lysosomal associated membrane protein, e.g., such as a human or mouse lysosomal associated membrane protein.

More generally, a "lysosomal membrane protein" refers to any protein comprising a domain found in the membrane of an endosomal/lysosomal compartment or lysosome-related organelle and which further comprises a lumenal domain.

As used herein, "targeting" denotes the polypeptide sequence that directs a chimeric protein of the invention to a preferred site, such as a cellular organelle or compartment where antigen processing and binding to MHC II occurs. As such, a "targeting domain" refers to a series of amino acids that are required for delivery to a cellular compartment/organelle. Preferably, a targeting domain is a sequence that binds to an adaptor or AP protein (e.g., such as an AP1, AP2, or AP3 protein). Exemplary targeting domain sequences are described in DellAngelica, 2000, for example.

As used herein, in vivo nucleic acid delivery, nucleic acid transfer, nucleic acid therapy, and the like, refer to the introduction of a vector comprising an exogenous polynucleotide directly into the body of an organism, such as a human or non-human mammal, whereby the exogenous polynucleotide is introduced into a cell of such organism in vivo.

As used herein, the term in situ refers to a type of in vivo nucleic acid delivery in which the nucleic acid is brought into proximity with a target cell (e.g., the nucleic acid is not administered systemically). For example, in situ delivery methods include, but are not limited to, injecting a nucleic acid directly at a site (e.g., into a tissue, such as a tumor or heart muscle), contacting the nucleic acid with cell(s) or tissue through an open surgical field, or delivering the nucleic acid to a site using a medical access device such as a catheter.

As used herein, the terms "isolated" and "purified" are used at times interchangeably to mean separated from constituents, cellular and otherwise, in which the polynucleotide, peptide, polypeptide, protein, antibody, or fragments thereof, are normally associated with in nature. For example, with respect to a polynucleotide, an isolated polynucleotide is one that is separated from the 5' and 3' sequences with which it is normally associated in the chromosome. As is apparent to those of skill in the art, a non-naturally occurring polynucleotide, peptide, polypeptide, protein, antibody, or fragments thereof, does not require "isolation" to distinguish it from its naturally occurring counterpart. Furthermore, the terms "isolated" and "purified" do not imply total isolation and total purity. These terms are used to denote both partial and total purity from some or all other substances naturally found in association with the polynucleotide, etc. Thus, these terms can mean isolation or purification from one naturally associated substance (e.g., isolation or purification of DNA from RNA), isolation or purification from other substances of the same general class of molecule (e.g., a particular protein showing 20% purity as compared to all proteins in a sample), or any combination. Isolation and purification can mean any level from about 1% to about 100%, including 100%. As such, an "isolated" or "purified" population of cells is substantially free of cells and materials with which it is associated in nature. By substantially free or substantially purified APCs is meant at least 50% of the population of cells are APCs, preferably at least 70%, more preferably at least 80%, and even more preferably at least 90% free of non-APCs cells with which they are associated in nature. Of course, those of skill in the art will recognize that all specific values, including fractions of values, are encompassed within these ranges without the need for each particular value to be listed herein. Each value is not specifically disclosed for the sake of brevity; however, the reader is to understand that each and every specific value is inherently disclosed and encompassed by the invention.

As used herein, a "target cell" or "recipient cell" refers to an individual cell or cell which is desired to be, or has been, a recipient of exogenous nucleic acid molecules, polynucleotides, and/or proteins. The term is also intended to include progeny of a single cell, and the progeny may not necessarily be completely identical (in morphology or in genomic or total DNA complement) to the original parent cell due to natural, accidental, or deliberate mutation. A target cell may be in contact with other cells (e.g., as in a tissue) or may be found circulating within the body of an organism.

The term "antigen presenting cell" or "APC" as used herein intends any cell that presents on its surface an antigen in association with a major histocompatibility complex molecule, or portion thereof, or, alternatively, one or more non-classical MHC molecules, or a portion thereof. Examples of suitable APCs are discussed in detail below and include, but are not limited to, whole cells such as macrophages, dendritic cells, B cells, hybrid APCs, and foster antigen presenting cells.

As used herein an "engineered antigen-presenting cell" refers to an antigen-presenting cell that has a non-natural molecular moiety on its surface. For example, such a cell may not naturally have a co-stimulator on its surface or may have additional artificial co-stimulator in addition to natural co-stimulator on its surface, or may express a non-natural class II molecule on its surface.

As used herein, the term "immune effector cells" refers to cells that are capable of binding an antigen and that mediate an immune response. These cells include, but are not limited to, T cells, B cells, monocytes, macrophages, NK cells, and cytotoxic T lymphocytes (CTLs), for example CTL lines, CTL clones, and CTLs from tumor, inflammatory, or other infiltrates.

As used herein, the terms "subject" and "patient" are used interchangeably to indicate an animal for which the present invention is directed. The term animal is to be understood to include humans and non-human animals; where a distinction between the two is desired, the terms human and/or non-human animal are used. In embodiments, the subject or patient is a vertebrate, preferably a mammal, more preferably a human. Mammals include, but are not limited to, murines, simians, humans, farm animals (e.g., bovines, ovines, porcines), sport animals (e.g. equines), and pets (e.g., canines and felines).

Clinical allergy symptoms are known to those of skill in the art, and an exhaustive listing herein is not required. Non-limiting examples include rhinitis, conjunctivitis, asthma, urticaria, eczema, which includes reactions in the skin, eyes, nose, upper and lower airways with common symptoms such as redness and itching of eyes and nose, itching and runny nose, coaching, wheezing, shortness of breath, itching, and swelling of tissue.

Examples of "immunological in vivo tests" are Skin Prick Test (SPT), Conjunctival Provocation Test (CPT), Bronchial Challenge with Allergen (BCA), and various clinical tests in which one or more allergy symptoms is monitored. See, for example, Haugaard et al., J Allergy Clin Immunol, Vol. 91, No. 3, pp 709-722, March 1993.

As used herein, the term "pharmaceutically acceptable carrier" encompasses any of the standard pharmaceutical carriers known in the art, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin Remington's Pharm. Sci., 15th Ed. (Mack Publ. Co., Easton (1975)).

As used herein, a "therapeutically effective amount" is used herein to mean an amount sufficient to prevent, correct, and/or normalize an abnormal physiological response. In one aspect, a "therapeutically effective amount" is an amount sufficient to reduce by at least about 30 percent, more preferably by at least 50 percent, most preferably by at least 90 percent, a clinically significant feature of pathology, such as for example, size of a tumor mass, antibody production, cytokine production, fever or white cell count, or level of histamine.

An "antibody" is any immunoglobulin, including antibodies and fragments thereof, that binds a specific epitope. The term encompasses polyclonal, monoclonal, and chimeric antibodies (e.g., bispecific antibodies). An "antibody combining site" is that structural portion of an antibody molecule comprised of heavy and light chain variable and hypervariable regions that specifically binds antigen. Exemplary antibody molecules are intact immunoglobulin molecules, substantially intact immunoglobulin molecules, and those portions of an immunoglobulin molecule that contains the paratope, including Fab, Fab', F(ab')$_2$, and F(v) portions, which portions are preferred for use in the therapeutic methods described herein.

The term "oromucosal administration" refers to a route of administration where the dosage form is placed under the tongue or anywhere else in the oral cavity to allow the active ingredient to come in contact with the mucosa of the oral cavity or the pharynx of the patient in order to obtain a local or systemic effect of the active ingredient. An example of an oromucosal administration route is sublingual administration. The term "sublingual administration" refers to a route of administration where a dosage form is placed underneath the tongue in order to obtain a local or systemic effect of the active ingredient. As used herein, the term "intradermal delivery" means delivery of the vaccine to the dermis in the skin. However, the vaccine will not necessarily be located exclusively in the dermis. The dermis is the layer in the skin located between about 1.0 and about 2.0 mm from the surface in human skin, but there is a certain amount of variation between individuals and in different parts of the body. In general, it can be expected to reach the dermis by going 1.5 mm below the surface of the skin. The dermis is located between the stratum corneum and the epidermis at the surface and the subcutaneous layer below. Depending on the mode of delivery, the vaccine may ultimately be located solely or primarily within the dermis, or it may ultimately be distributed within the epidermis and the dermis.

As used herein, the term "prevent" in the context of allergy immunotherapy, allergy treatment, or other terms that describe an intervention designed for an allergy patient, means the prevention of an IgE response in at least 20% of all patients. The term "prevent" does not mean total prevention from developing an IgE mediated disease in all patients, and such a definition is outside the scope of the present invention for treating allergy through a mechanism that reduces allergy symptoms, and is inconsistent with the use of the term in the art. It is well known to those skilled in the art of allergy immunotherapy that allergy treatments are not 100% effective in 100% of patients, and as such an absolute definition of "prevent" does not apply within the context of the present invention. The art-recognized concept of prevention is contemplated by the present invention.

The present invention provides polynucleic acids, polyaminoacids, and methods of treating subjects in need of the polynucleic acids and polyaminoacids. Broadly speaking, the polynucleic acids can be thought of as nucleic acid (e.g., DNA, RNA) vaccines for the intracellular production of allergenic sequences (polyaminoacids) that elicit a protective immune response within the body of the subject to whom the polynucleic acid is administered. The polynucleic acids, when administered, preferentially evoke a cell-mediated immune response via the MHC-II pathway and production of IgG antibodies by activating an allergen-specific T-helper type 1 (Th1) cellular response with the production of interferons by APCs, NK cells, and T cells rather than a Th2-type response, which involves production of IgE antibodies, granulocytes (e.g., eosinophils), and other substances. To an extent, both an MHC-II and an MHC-I response can be generated; however, the invention provides a response that is primarily or substantially an MHC-II response. Preferably, the nucleic acids do not encode an antibiotic resistance gene.

The invention is based, at least in part, on the recognition that a combination of certain structural, and thus functional, elements provides advantageous properties to the nucleic acid vaccines and the encoded allergens, and allows for allergy treatment methods that satisfy unmet needs in the art. In the various embodiments of the invention, which are intended to be understood as standing alone as independent embodiments and as embodiments that combine two or more features of the independent embodiments, the combinations include the use of a lysosomal trafficking domain to direct allergen amino acid sequences to lysosomes with MHC II proteins. Doing so allows for predominantly an IgG response as opposed to an IgE response to the allergen sequences. Yet further, independent embodiments or combinations of embodiments provide constructs containing a sufficient length of a nucleic acid sequence to encode an amino acid sequence that provides a naturally-occurring three-dimensional structure of an epitope. In preferred embodiments, the nucleic acid sequence provides/encodes the full-length allergen coding sequence, but which lacks any naturally-occurring signal peptide sequence associated with the allergen sequence. In other embodiments, the nucleic acid sequence encodes at least one allergenic region of an allergen, but not the full-length allergen protein (and also lacking the signal sequence, if one was naturally present). Although it is recognized in the art that an immune response can be generated against the primary sequence of an epitope, the present invention recognizes that nucleic acid vaccines for the production of an MHC-II immune response to encoded epitopes preferably uses nucleic acid constructs that encode enough sequence data to produce a correct three-dimensional peptide structure in the region comprising an allergenic epitope, at least at the time when the allergenic sequence is delivered to a lysosome for processing. While not being limited to any particular molecular theory, it is believed that delivery of a properly three-dimensionally folded protein, polypeptide, or peptide to an endosome improves processing and presentation of allergenic epitopes for an immune response.

As yet another example of an embodiment that can be implemented, alone or as part of a combination of embodiments, the expression of multiple allergens from a single construct is provided. To date, it has not been shown that a nucleic acid vaccine that is protective against an allergen can be effectively produced and used. The present invention not only provides an effective nucleic acid vaccine against an allergen, but further provides an effective nucleic acid vaccine against multiple allergens at the same time. The allergens can be allergens from the same source (e.g., a single plant), or can be allergens from two or more sources (e.g., a tree, a flower, a food, etc.). As above, the full-length allergen sequences can be used (lacking any naturally-associated signal sequence for the allergen), or allergenic portions can be used. In constructs comprising multiple allergen sequences, any mixture of full-length or truncated allergen sequences can be used. Further, as with other embodiments, it is preferred that naturally-occurring signal sequence for each allergen sequence be removed (i.e., the naturally-occurring signal sequences for each allergen sequence are not present in the constructs).

Although the use of signal sequences for the independent allergenic sequences within the allergen domain has been found to be detrimental to the function of the nucleic acid construct, it has been found that the use of signal sequence region or domain within the nucleic acid vaccine constructs is an important feature. As such, in embodiments, the nucleic acid vaccine includes at least one signal sequence within the signal sequence domain to direct the encoded peptide to and through a membrane. Although the amino acid sequence of the signal sequence may vary from construct to construct, and any known signal sequence can be selected, it has been found that in preferred embodiments, the signal sequence is present and provided in-frame with the coding sequence of the allergen sequence(s). The use of a single signal sequence is adequate to direct the entire encoded chimeric protein to and through a membrane. As such, signal sequences for each allergen sequence are not necessary and, in fact, have been found to be detrimental to proper localization, processing, and expression of allergen epitopes on immune cell surfaces.

And further, in specific embodiments and in combinations of embodiments, it has been found that sequestration, or physical protection, of allergen sequences during the transfer of the polypeptide from the cytoplasm to the endosome, including the time in the endosome prior to cleavage of the polypeptide into units for presentation at the cell surface, can be an important factor in providing a useful nucleic acid vaccine according to the invention. As such, in general, the invention includes a construct that comprises an intra-organelle stabilizing domain (IOSD) to protect allergen sequences.

The nucleic acid of the invention comprises at least the following domains: a signal sequence domain; an intra-organelle stabilizing domain; an allergen domain (which can comprise a single allergen or two or more allergens, each comprising one or more allergenic epitopes); a transmembrane domain; and a cytoplasmic lysosome/endosome targeting domain. The various domains are present on a single chimeric or engineered nucleic acid. The various domains can be combined in any linear order using techniques known and widely practiced in the art. In preferred embodiments, the domains are combined and arranged such that they comprise a single open reading frame encoding a chimeric protein, the open reading frame being operably linked to transcriptional elements sufficient for expression of the chimeric protein. The nucleic acid thus can be an expression vector, such as a plasmid, phagemid, viral vector, or the like. Preferably, the nucleic acid comprises transcriptional elements suitable for expression in mammalian cells, such as human cells. Such expression vector elements and expression vectors are known and widely used in the art, as exemplified by U.S. patent application publication number 2004/0157307, which is incorporated herein by reference. A non-limiting example of a plasmid backbone for use in creating nucleic acid constructs according to the invention is referred to at times herein as a "pITI" plasmid, the sequence of which is provided as SEQ ID NO: 1.

Figure 3:
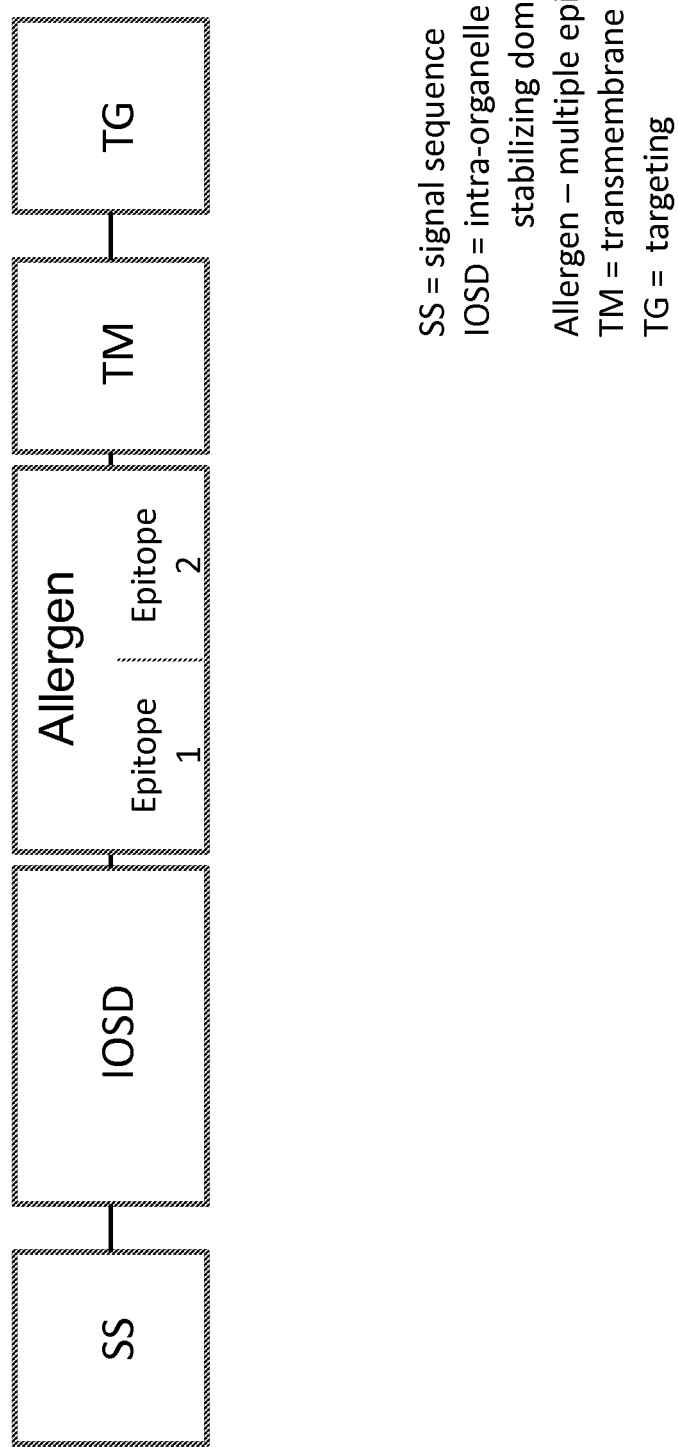
FIG. 3 is a schematic representation of a nucleic acid according to an alternative embodiment of the invention, in which multiple epitope sequences of a single allergen are provided in the allergen domain.
Figure 4:
FIG. 4 is a schematic representation of a nucleic acid according to an alternative embodiment of the invention, in which multiple different allergen sequences are provided in the allergen domain.

Three exemplary configurations of the nucleic acid of the invention are depicted schematically in FIGS. 1, 3, and 4, respectively. FIG. 1 shows a sequential arrangement of domains in which a single allergen comprising a single epitope is included in the encoded chimeric protein. FIG. 3 shows a sequential arrangement of domains in which multiple different epitopes of a single allergen are included in the encoded chimeric protein within the allergen domain. The two epitopes are arranged such that they are in the same reading frame and are thus both produced as part of the chimeric protein. Those of skill in the art will immediately recognize that three or more epitopes can be provided in the same reading frame within the epitope domain using standard molecular biology techniques. FIG. 4 shows a sequential arrangement of domains in which two different allergens are present in the allergen domain. Of course, the skilled artisan will recognize that each allergen sequence can contain one or multiple allergenic epitopes. Based on these three schematic representations of embodiments of the nucleic acids of the invention, the reader will immediately recognize that any number of allergens, from any number of sources, and containing any number of epitopes, can be included within the allergen domain, and can be linked in-frame using standard molecular biology techniques.

Figure 2:
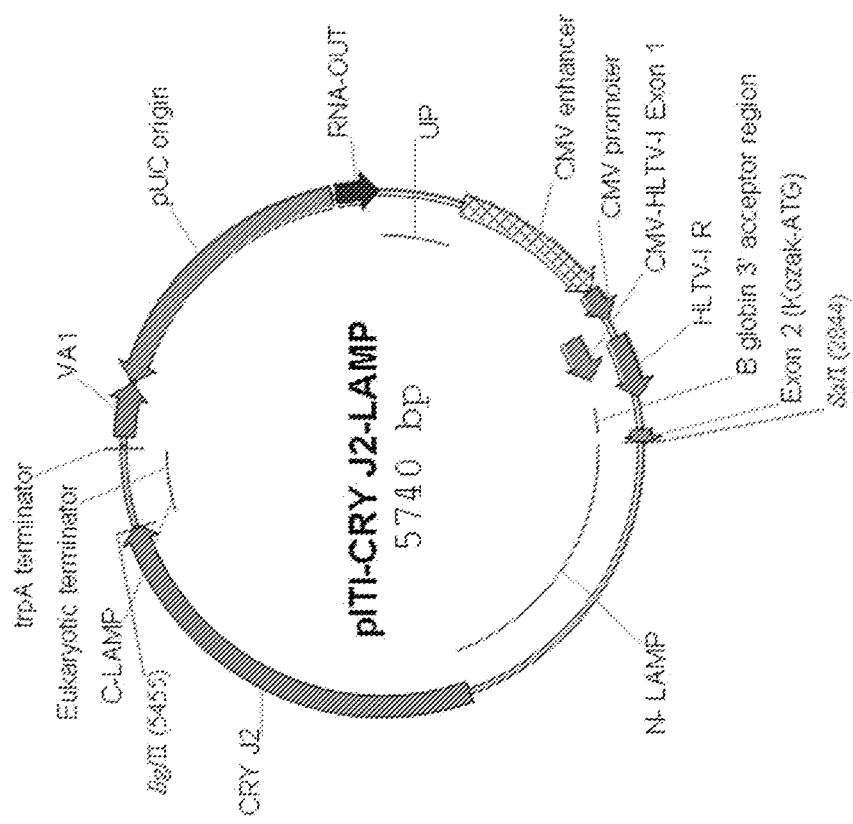
FIG. 2 shows a vector map of a nucleic acid according to the invention, in which the allergen domain comprises the CryJ2 allergen (an allergen from C. japonica), but without a signal sequence, inserted between human LAMP N-terminal sequences (SS and ISOD) and human LAMP C-terminal sequences (TM and TG).

FIG. 2 depicts a vector map of a nucleic acid according to one embodiment of the invention ("pITI-CRY J2-LAMP"; also referred to herein at times as "CRYJ2-LAMP"), which generally relates to the embodiment of the invention depicted schematically in FIG. 1. The vector or delivery vehicle includes a plasmid backbone with a pUC origin of replication and various transcription and expression elements for production of the encoded protein. More specifically, it includes the sequence of the pITI backbone (SEQ ID NO: 1). It is to be noted that the nucleic acid construct does not include an antibiotic resistance gene, in accordance with preferred embodiments of the invention. The nucleic acid further comprises sequences for the encoded protein, which comprises an N-terminal region of the human LAMP protein, which includes a signal sequence and an intra-organelle stabilizing domain. The nucleic acid further provides sequences for the encoded protein that comprises the CryJ2 allergen sequence (lacking its signal sequence) fused in-frame to the N-terminal region of the LAMP protein. The nucleic acid further includes sequences encoding a portion of the C-terminal region of the human LAMP protein, which includes a transmembrane region and a targeting region. The coding region for the CRY J2-LAMP chimeric protein sequence is provided as SEQ ID NO:2. The amino acid sequence for the CRY J2-LAMP chimeric protein is provided as SEQ ID NO:3.

In exemplary embodiments, the invention also relates to nucleic acid constructs for the delivery and expression of other allergens of *C. japonica*, including the CryJ1 allergen. Using the same plasmid backbone, a pITI-CRYJ1-LAMP construct has been created. The chimeric protein can elicit an MHC II type immune response. The coding region for the pITI-CRYJ1-LAMP construct is presented as SEQ ID NO:4. The amino acid sequence for the CRY J1-LAMP chimeric protein is provided as SEQ ID NO:5.

Figure 5:
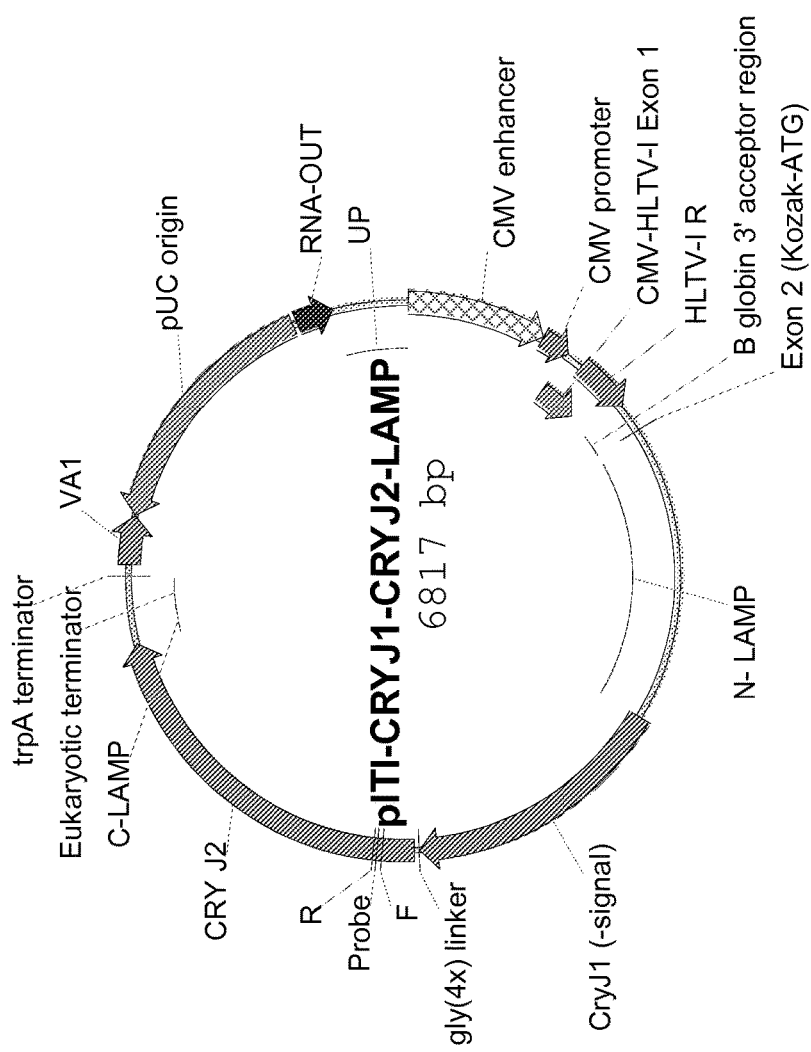
FIG. 5 shows a vector map of a nucleic acid according to the invention in which the allergen domain comprises the allergen sequences (without signal peptides) for the allergens CryJ1 (an allergen from *C. japonica*) and CryJ2 (an allergen from *C. japonica*).

As shown in FIGS. 3 and 4, the allergen domain can include an allergen having multiple allergenic epitopes, or can include multiple allergens (each having one or more allergenic epitopes). FIG. 5 depicts a vector map of a particular exemplary embodiment of a nucleic acid construct in which the allergen domain includes two allergenic sequences. In this exemplary embodiment, the allergen domain contains the CryJ1 and CryJ2 allergens (each lacking its natural signal sequence) of *C. japonica* fused in-frame and fused at the N-terminal end with a LAMP signal sequence domain and intra-organelle stabilizing domain. The CryJ1-CryJ2 sequences are also fused at the C-terminal end with a LAMP transmembrane domain and targeting domain. The full nucleotide sequence of the coding region for the chimeric protein is presented as SEQ ID NO:6. The full amino acid sequence of the encoded chimeric protein is presented as SEQ ID NO:7, in which: residues 1-27 represent the signal sequence for the chimeric protein; residues 28-380 represent the intra-organelle stabilizing domain (sequence taken from human LAMP); residues 381 and 382 represent a linker; residues 383-735 represent the coding region of the CryJ1 (without its signal sequence); residues 736-741 represent a linker region; residues 742-1232 represent the coding region for the CryJ2 allergen; residues 1233-1234 represent a linker region; residues 1235-1258 represent the transmembrane and targeting domain; and residues 1259-1270 represent additional C-terminal residues.

Figure 6A:
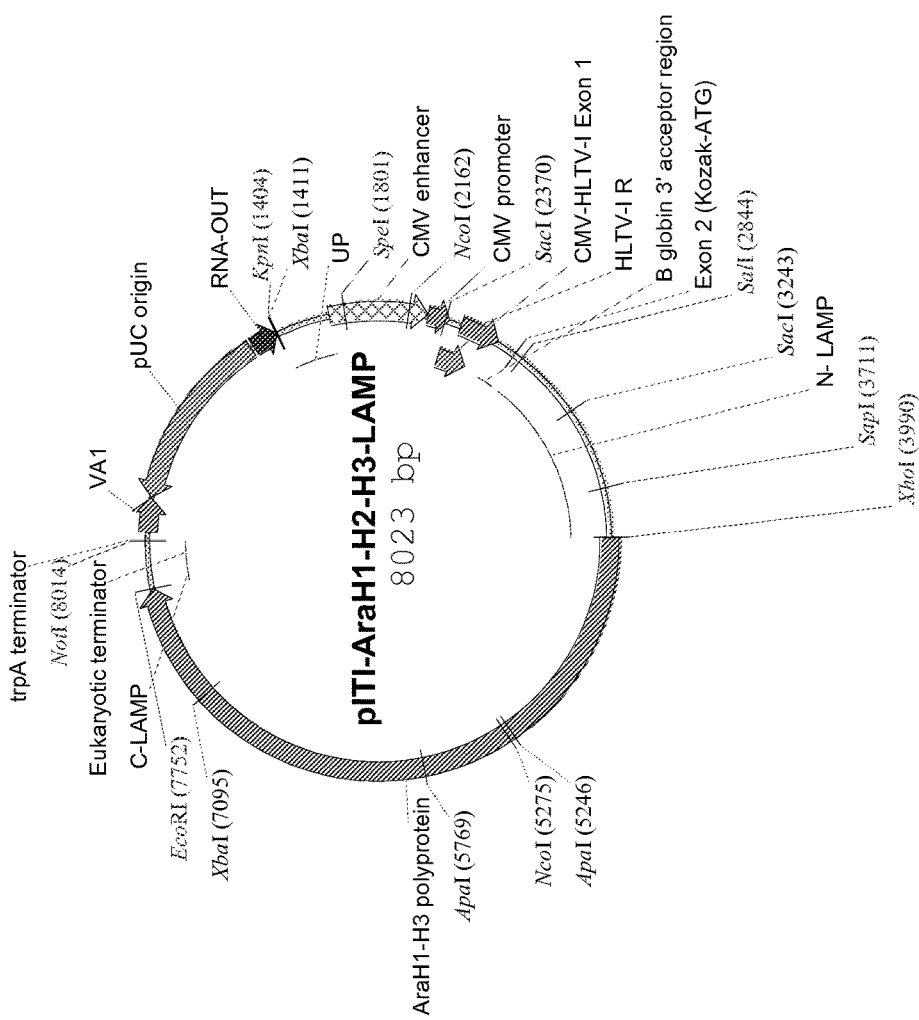
FIG. 6A shows a vector map of a nucleic acid that includes three peanut allergens (AraH1, AraH2, and AraH3, all lacking signal sequences) in the allergen domain.

The nucleic acid constructs of the invention are essentially limitless in the number of allergens that can be coordinately produced. As such, two, three, four, five, six, ten, twenty, or more different allergens (from the same or a mixture of different sources) can be included in the nucleic acid constructs of the invention. FIG. 6A presents a vector map of another exemplary nucleic acid according to an embodiment of the invention. The vector or delivery vehicle includes a plasmid backbone with a pUC origin of replication and various transcription and expression elements for production of the encoded protein. The backbone can be, but is not necessarily, the pITI backbone of SEQ ID NO: 1. The nucleic acid further comprises sequences for the encoded protein, which comprises an N-terminal region of the human LAMP protein, which includes a signal sequence domain and an intra-organelle stabilizing domain. The nucleic acid further provides sequences for an encoded chimeric protein that comprises the peanut allergen polyprotein AraH1/AraH2/AraH3. The nucleic acid further includes sequences encoding a portion of the C-terminal region of the human LAMP protein, which includes a transmembrane region and a targeting region. The nucleotide sequence for the coding region of the chimeric protein is provided as SEQ ID NO: 8 The chimeric protein encoded by the vector of FIG. 6A is presented schematically in FIG. 6B (and as SEQ ID NO:9).

The domains present in the nucleic acids of the invention are described in more detail below with respect to the functions provided by the encoded chimeric proteins. It is to be understood that practice of the invention is not dependent upon or limited by any particular nucleic acid or protein sequence, but rather it is the combination of elements and domains that provides the advantages and properties to the constructs. It is also to be understood that the description relating to the various domains of the nucleic acid construct, when discussed in the context of the physical and functional characteristics of the encoded protein, and vice versa. It is sufficient to apprise one of skill in the art of the physical and functional characteristics of either the nucleic acids or the proteins. It is a simple matter using computers and the degeneracy of the genetic code to arrive at all possible nucleic acid molecules encoding known protein sequences and to arrive at proteins encoded by nucleic acids. Thus reference to a physical or functional characteristic of a particular protein sequence immediately discloses to the skilled artisan all of the possible nucleic acid sequences associated with that physical or functional characteristic, and vice versa.

It is also well within the skill of those of skill in the art to design and combine two or more nucleic acid molecules or sequences to arrive at a sequence encoding a chimeric protein according to the invention. Likewise, it is well within the skilled artisan's abilities to select and combine transcription and translation control elements to express the coding sequences and chimeric proteins in vivo or in vitro as desired. Accordingly, these commonly used techniques need not be discussed in detail herein to enable one to practice the present invention.

The nucleic acid of the invention comprises a signal sequence domain. The signal sequence domain contains a signal sequence that is provided for insertion of the encoded chimeric protein into a biological membrane that defines the border between an external environment and an internal environment. The signal sequence also directs transfer of the protein from the external environment to the internal environment. The general structure of a signal sequence is well known in the art, as are numerous examples of particular signal sequences. The practitioner is free to select any appropriate signal sequence according to the various selection parameters for each embodiment falling within the scope of this invention. In exemplary embodiments, the signal sequence is one that directs the chimeric protein to the endoplasmic reticulum. It is important to note at this juncture that the signal sequence domain is the only portion of the chimeric protein that contains a signal sequence. As such, the naturally-occurring signal sequences of allergens residing in the allergen domain have been removed prior to inclusion of the allergen sequences in the construct. It has been found that removal of these individual signal sequences improves the overall performance of the construct in vivo.

The nucleic acid of the invention comprises an intra-organelle stabilizing domain (IOSD). The IOSD comprises a sequence that encodes an amino acid sequence that binds, via chemical bonds, to one or more sequences in the allergen domain and protects those sequences from degradation (e.g., proteolysis) prior to arrival of the chimeric protein in the endosomal/lysosomal compartment. In essence, the IOSD can be envisioned as a protective cap for the allergen domain sequences, shielding those sequences, and in particular allergenic epitope sequences, from proteolytic enzymes, low pH, and other protein-destabilizing substances and conditions. The IOSD can be any of a number of known or engineered sequences, including, but not limited to, a LAMP polypeptide lumenal domain and the macrosialin/CD68 protein, which is a heavily glycosylated transmembrane protein that is expressed in macrophages and macrophage-like cells as a late endosomal protein. The key feature of the IOSD is the ability of the IOSD to bind to and protect the allergen domain from proteolysis until the MHC class II molecule is released from the invariant peptide. In this way, the three-dimensional structures of the allergenic epitope(s) are preserved until active MHC class II molecules are available for interaction. In preferred embodiments, the IOSD comprises all or part of the sequence of a lysosomal protein. In some embodiments, the IOSD is a protein or polypeptide other than a LAMP polypeptide lumenal domain, such as, but not limited to, macrosialin/CD68.

The nucleic acid construct of the invention comprises an allergen domain. The allergen domain comprises one or more sequences that encode allergen proteins, polypeptides, or peptides, which comprise one or more allergenic epitopes. The allergen domain does not include signal sequences from the allergens present. Numerous proteinaceous allergens are known in the art, and any one or combination of allergens and/or allergenic epitopes can be used in accordance with the present invention. Where less than a full-length allergenic sequence is used, preferably, one or more epitopes of the full-length allergen protein are provided in the context of their natural positions within the allergenic protein. More specifically, the present invention provides for improved nucleic acid vaccines, in which the vaccines encode chimeric proteins that retain or substantially retain their three dimensional structure until MHC class II molecules are competent to bind to epitopes on the chimeric proteins. In this way, an improved immune response can be elicited, as compared to delivery to the MHC class II molecules of short peptides, which generally will lack appropriate three dimensional structures. Accordingly, it is preferred that the allergen domain encode relatively long amino acid sequences that include one or more epitopes, if originally present on the allergen protein.

The allergen domain can include two or more allergens, each containing one or more allergenic epitopes. It is known that certain allergenic proteins contain two or more epitopes. As a preferred embodiment of the invention uses an entire allergenic coding region (i.e., the coding region lacking a signal sequence), or a substantial portion thereof, of an allergenic protein, certain allergen domains will include two or more epitopes in their naturally-occurring relationship. Alternatively, two or more known epitopes can be fused into one coding region. Yet again, in exemplary embodiments, two or more allergenic proteins, or allergenic regions thereof, are present in the allergen domain. Where two or more epitopes are engineered to be present in a single epitope domain, the epitopes can be from the same antigenic protein. Alternatively, they can be from two different proteins of the same species. Yet again, they can be from the same protein of two different species. Furthermore, they can be from two or more different proteins from two or more different species. In essence, any combination of epitopes from the same or different proteins from the same or different species is contemplated by this invention. Likewise, the order of the various allergens and epitopes can be varied in any way imaginable. The mixing of allergenic proteins and/or allergenic peptides from multiple species allows the creation of a robust nucleic acid vaccine that can provide treatment for allergies to a single source organism (e.g., particular species of tree) based on multiple allergens, as well as treatment for allergies to multiple source organisms (e.g., multiple plants that release spores during the same season of the year) based on multiple allergens. The ability to combat multiple allergies from a single nucleic acid vaccine has not been proven to date.

The nucleic acid construct of the invention further comprises a transmembrane domain. Transmembrane domains are well known and well characterized physical and functional elements of proteins that exist partially on both sides of a biological membrane. In essence, a transmembrane domain is a linear sequence of amino acids that are generally hydrophobic or lipophilic in nature and which function to anchor a protein at a biological membrane. Generally, such sequences are 20-25 residues in length. Those of skill in the art are well aware of such sequences and can easily obtain or engineer a suitable transmembrane sequence for use in the present invention.

In addition to the elements discussed above, the nucleic acid of the invention comprises a targeting domain. The targeting domain is a sequence that encodes an amino acid sequence that functions to target the encoded chimeric protein to the endosomal/lysosomal compartment. While not so limited in its identity, in preferred embodiments, the targeting domain comprises the C-terminal cytoplasmic targeting sequence of the LAMP polypeptide, DC-LAMP, LAMP2, LAMP-3, LIMP II, ENDOLYN, or macrosialin/CD68.

In embodiments, the nucleic acid of the invention comprises, as part of the allergen domain, the sequence of SEQ ID NO:2 (i.e., the Cry J2 nucleotide sequence lacking its signal sequence) or another sequence encoding SEQ ID NO: 3 (i.e., the Cry J2 protein sequence lacking its signal sequence) in the allergen domain. SEQ ID NO:2 consists of nucleotides encoding the full protein coding sequence of Cry J2, with the exception of its signal sequence (i.e., SEQ ID NO:2), a pectate lysase protein found in the pollen of *Cryptomeria japonica*. Cry J2 is well known in the art to be correlated with seasonal and persistent allergies in areas where cedar pollen is present. IgE specific to Cry J2 is commonly found in allergic patients in areas near cedar groves. It is to be noted that, in the Sequence Listing provided as part of the disclosure of the invention, the signal sequence for each allergen, if present, is noted. It is to be understood that, within the context of the constructs of the invention, these signal sequences are not present.

In other embodiments, the nucleic acid comprises the sequence of SEQ ID NO:4 (i.e., the Cry J1 nucleotide sequence, lacking its signal sequence) or another sequence encoding SEQ ID NO:5 (i.e., the Cry J2 protein sequence lacking its signal sequence). In yet other embodiments, the nucleic acid comprises the sequence of both SEQ ID NO:2 and SEQ ID NO:4, or other sequences encoding SEQ ID NO:3 and SEQ ID NO:5, respectively. In embodiments, the nucleic acid comprises one or more of the other sequences disclosed herein, such as those encoding any of the following allergens: Cry J3 (Cry J3.8; *C. japonica*; SEQ ID NO: 10; signal sequence is residues 1-26), CJP-4 (*C. japonica*; SEQ ID NO: 11), CJP-6 (*C. japonica*; SEQ ID NO: 12), CJP-8 (*C. japonica*; SEQ ID NO: 13; signal sequence is residues 1-35), CPA63 (*C. japonica*; SEQ ID NO: 14; signal sequence is residues 1-20), CJP38 (*C. japonica*; SEQ ID NO: 15; signal sequence is residues 1-28), Cha o 1 (*C. obtuse*; SEQ ID NO: 16; signal sequence is residues 1-21), Jun a 1 (*J. ashei*; SEQ ID NO: 17; signal sequence is residues 1-21), Jun v 1 (*J. virginiana*: SEQ ID NO: 18; signal sequence is residues 1-21), Cup a 1 (*H. arizonica*; SEQ ID NO: 19; signal sequence is residues 1-21), Jun o 1 (*J. oxycedrus*; SEQ ID NO:20; signal sequence is residues 1-21), Cup s 1 (*C. sempervirens*; SEQ ID NO:21; signal sequence is residues 1-21) Cha o 2 (*C. obtuse*; SEQ ID NO:22; signal sequence is residues 1-22), Jun a 2 (*J. ashei*; SEQ ID NO:23; signal sequence is residues 1-22), Cup a 2 (*H. arizonica*; SEQ ID NO:24), Jun a 3 (*J. ashei*; SEQ ID NO:25; signal sequence is residues 1-16), Jun r 3 (*J. rigida*; SEQ ID NO:26; signal sequence is residues 1-26), Cup s 3 (*C. sempervirens*; SEQ ID NO:27; signal sequence is residues 1-26), Cup a 3 (*H. arizonica*; SEQ ID NO:28), Ch4A (*P. monticola*; SEQ ID NO:29; signal sequences is from residues 1-25), Ch4-1 (*P. menziesii*; SEQ ID NO:30; signal sequence is residues 1-26), PT-1 (*P. taeda*; SEQ ID NO:31), and LTP (*P. abies*; SEQ ID NO:32; signal sequence is from residues 1-25). Nucleic acid and amino acid sequences not listed with reference to SEQ ID NOs are also publicly available. It is a mere matter of computer program implementation to arrive at protein sequences according to the present invention based on the nucleic acid sequences. Of course, biochemically homologous sequences to these protein sequences are encompassed by these embodiments. For example, sequences showing 30% or more identity, such as 40% or more, 50% or more, 75% or more, 90% or more 95% or more, 98% or more, or 99% or more to the disclosed sequences are encompassed by these embodiments. It is to be understood that this concept applies not only to the particular sequences of allergens disclosed herein, but to all protein and nucleic acid sequences provided herein. Further, as stated above, each value within the disclosed ranges are understood to be specifically encompassed by the present disclosure.

In a particular instance of the invention, a DNA vaccine comprising SEQ ID NO:2 or another sequence encoding SEQ ID NO: 3 within the allergen domain is provided. When such a vaccine is administered to a patient for whom there is considerable evidence of a Japanese red cedar allergy, the vaccine results in the de novo synthesis of a fusion or chimeric (these terms used interchangeably herein) protein comprising the allergen Cry J2 (presented within SEQ ID NO:3). Due to the combination of domains present on the chimeric protein, the protein is directed from the endoplasmic reticulum into the endolysosomal pathway, resulting in the processing of the fusion protein into epitopes in MHC vesicles, some of which become bound to MHC class II molecules, leading to an enhanced humoral immune response.

In another instance of the invention, a DNA vaccine comprising the sequence of SEQ ID NO:4 or another sequence encoding SEQ ID NO:5 within the allergen domain is provided. When such a vaccine is administered to a patient for whom there is considerable evidence of a Japanese red cedar allergy, the vaccine results in the de novo synthesis of a fusion or chimeric (these terms used interchangeably herein) protein comprising the allergen Cry J1 (found within the sequence of SEQ ID NO:4). Due to the combination of domains present on the chimeric protein, the protein is directed from the endoplasmic reticulum into the endolysosomal pathway, resulting in the processing of the fusion protein into epitopes in MHC vesicles, some of which become bound to MHC class II molecules, leading to an enhanced humoral immune response.

In another instance of the invention, a DNA vaccine comprising SEQ ID NO:6 within the allergen domain is provided. When such a vaccine is administered to a patient for whom there is considerable evidence of a Japanese red cedar allergy, the vaccine results in the de novo synthesis of a fusion or chimeric (these terms used interchangeably herein) protein comprising the allergens CryJ1 and Cry J2 (SEQ ID NO:7). Due to the combination of domains present on the chimeric protein, the protein is directed from the endoplasmic reticulum into the endolysosomal pathway, resulting in the processing of the fusion protein into epitopes in WIC vesicles, some of which become bound to MHC class II molecules, leading to an enhanced humoral immune response.

In another instance of the invention, a nucleic acid encoding the full protein coding sequence of Jun a1, a pectate lysase belonging to the genus *Juniperus ashei*, is provided in the allergen domain. Jun a1 demonstrates a high degree of sequence identity with Cry J1 and both retains a similar enzymatic activity to Cry J1 and possesses a high similarity in known epitopes.

Other polypeptides are well known to be cross-reactive to Cry J1 and that this cross-reactivity is due to shared epitopes related to the enzymatic activity of pectate lysase family polypeptides. The family includes the major allergen of Japanese cypress (*Chamaecyparis obtusa* (Ch o 1)), and includes allergens from: *Juniperus ashei* (Jun a 1), *Juniperus virginiana* (Jun v 1), *Cuppressus arizonica* (Cup a 1), *Juniperus oxycedrus* (Jun o 1), and *Cupressus sempervirens* (Cup s 1). It has been observed in the literature that there is strong cross-reactivity among allergic patients to pollen from the cedar family (*Cupressus*). Table I, below, depicts a table showing levels of cross-reactivity among related proteins. While the invention is described in detail with regard to Cry J1 and Cry J2, it is to be understood that one or more of the allergens disclosed herein and particularly in Table I can be used in addition to or as alternatives to the Cry J1 and Cry J2 sequences.

TABLE 1

*Cryptomeria japonica* cross-reactivity to other allergens

| *Cryptomeria Japonica* | Cha o1 | Jun a1 | Jun v1 | Cup a1 | Jun o1 | Cup s1 | Cha o2 | Jun a2 | Cup a2 | Jun a3 | Jun r3 | Cup S3 | Cup A3 |
|---|---|---|---|---|---|---|---|---|---|---|---|---|---|
| Cry J1 | 80% | 79% | 80% | 75% | 85% | 85% | | | | | | | |
| Cry J2 | | | | | | | 74% | 71% | 80% | | | | |
| Cry J3 | | | | | | | | | | 86% | 87% | 85% | 87% |

| *Cryptomeria Japonica* | Ch4A | Ch4-1 | PT-1 | LTP |
|---|---|---|---|---|
| CJP-4 | 70% | 57% | | |
| CJP-6 | | | 74% | |
| CJP-8 | | | | 45% |
| CPA63 | | | | |

It is well known in the art that certain sites for inserting a nucleotide sequence for a coding region into the nucleotide sequence for a different coding region (i.e., fusion sites) are more favorable than others. The location of the allergen sequence taught in, for example, FIGS. 1-5 is taught as the favorable location for using the composition taught in the present invention. It is within the scope of the present invention to move the location of the allergen sequence to other locations, such as within the luminal domain of a LAMP polypeptide or other intra-organelle stabilizing domain. However, it is preferred that the allergen is not placed within the coding region of either the transmembrane or cytoplasmic domain. In a preferred instance of the invention, the allergen sequence is inserted into the luminal domain of a LAMP polypeptide within 5 amino acids from the junction with the transmembrane domain and up to 20 amino acids on the 5' N terminal side of a LAMP polypeptide luminal domain.

The nucleic acid of the invention can be provided as a purified or isolated molecule. The nucleic acid also can be provided as part of a composition. The composition can consist essentially of the nucleic acid, meaning that the nucleic acid is the only nucleic acid in the composition suitable for expression of a coding sequence. Alternatively, the composition can comprise a nucleic acid of the invention. In exemplary embodiments, the composition is a pharmaceutical composition comprising the nucleic acid of the invention along with one or more pharmaceutically acceptable substances or carriers. In some embodiments, the composition comprises a substance that promotes uptake of the nucleic acid by a cell. In some embodiments, the composition comprises a targeting molecule that assists in delivering the nucleic acid to a specific cell type, such as an immune cell (e.g., and APC). In embodiments, the nucleic acid is part of a delivery vehicle or delivery vector for delivery of the nucleic acid to a cell or tissue.

In a particular instance of the invention, the composition comprises a mixture of two DNA vaccines, where one vaccine comprises the sequence of one allergen and where the other vaccine comprises the sequence of another allergen. The two vaccine constructs can be mixed together at a ratio of 1:1, 1:2, 1:3, 1:4, sequentially up to 1:10. The preferred ratio is 1:1.

In a particular instance of the invention, the nucleic acids of Cry J1, Cry J2, and/or Jun a2 are present within a nucleic acid delivery vector. In a preferred embodiment of the invention, the nucleic acid delivery vector does not contain an antibiotic resistance gene, such as the nucleic acid delivery vector taught by U.S. patent application publication number 2008/006554, or vectors that are disclosed in or result from U.S. patent application publication number 2006/003148. In a particular instance of the invention, the nucleic acid is a viral vector, such as an adenoviral vector.

The nucleic acids and compositions are novel and useful as agents for reducing allergic reactions in patients. For example, the nucleic acids and compositions are useful in reducing pollinosis in patients with a demonstrated allergic reaction correlated with Japanese red cedar pollen, or from a homologous pollen or allergen. As another non-limiting example, the nucleic acids are useful for reducing food allergies, such as allergy to peanuts or other nuts. Delivery of nucleic acids and compositions to treat pollinosis from Japanese red cedar pollen, such that the nucleic acids and compositions transfect an antigen presenting cell, results in an increase in serum levels of immunoglobulin G (IgG) specific to epitopes contained within Cry J1 and/or Cry J2. This response is useful for the reduction of allergy symptoms. Delivery of allergens for other allergies, including ragweed, other tree pollens, and foods also result in increase in serum levels of IgG.

Methods of treating subjects in need are also provided by this invention. The methods are methods of prophylactically treating or therapeutically treating a subject suffering from or at risk of developing an allergic reaction to one or more allergens. The method comprises administering to the subject a DNA vaccine according to the invention in an amount sufficient to cause uptake of and expression of the DNA vaccine by an APC. Expression of the DNA vaccine results in presentation of the encoded allergenic epitope(s) on the APC, and development of an IgG immune response.

In a particular instance of the invention, SEQ ID NO:2, SEQ ID NO:4, and/or another allergen encoding sequence are administered to a cell. In preferred embodiments, the cell is an antigen presenting cell, such as a dendritic cell. Preferably, the dendritic cell is a human dendritic cell. The present invention can be administered by methods known in the art to be effective delivery methods for nucleic acid vaccines, including intramuscular injection, subcutaneous injection, electroporation, gene gun vaccination, or liposome-mediated transfer.

This invention provides a formulation useful for the treatment of pollinosis correlated with Japanese red cedar pollen. It has previously been determined that delivering a DNA plasmid encoding the protein coding sequence of an allergen to an animal can increase IFN-gamma production and lower IL-4 production, which is useful in treating animals allergic to the specific allergen. The present invention provides an improved DNA vaccine composition for treating patients with an allergy correlated to Japanese red cedar pollen. The fusion protein of the invention has a specific intracellular trafficking pattern that intersects with MHC class II vesicles, and results in enhanced presentation of allergen epitopes to the immune system, specifically resulting in an enhanced antibody response. Nucleic acids and compositions provided by the present invention are useful for conducting allergy immunotherapy.

The present invention provides a formulation that when administered to a cell results in an increased specific antibody response. The increased antibody response to the allergen is useful for treating an IgE-mediated allergic disease. IgE has certain properties related to its cellular restriction and the resulting intracellular signaling upon binding cognate allergen. IgE is generated against an allergen when B cells receive IL-4 secreted by Th2 cells. This helps instruct B cells to produce IgE class antibodies. Upon secretion by B cells, IgE binds to Fc-eRI, its high affinity receptor expressed by mast cells and eosinophils, resulting in these cells and the animal becoming sensitized to future allergen exposure. Consequently, the symptoms of allergy can be triggered upon the ingestion, inhalation, or mucosal contact with an allergen. Due to the binding properties of antibodies, it has been proposed that one way of reducing allergy symptoms is to chelate free allergen available for binding by IgE through competition with other antibody classes. In particular, an allergy formulation that increases IgG has been proposed to be an pathway for reducing allergic disease. The invention described herein induces enhanced IgG production, thus causing a decrease in the ratio of IgE to IgG in a clinically significant manner. The results of studies that have been conducted indicate that at day 98, the level of IgG induced by a Cry J2-LAMP construct is greater than that induced by delivery of nucleotides encoding unmodified Cry J2.

In another instance of the invention, a method is taught for selecting pectate lysase polypeptides found in the pollen of a cedar tree, for determining the degree of sequence homology with the amino acid or nucleic acid sequence of a Cry J1, a pectate lysase, so that a new composition of matter similar to Cry J1 can be generated, and so that administration of the homologous composition of matter to a patient would produce a therapeutic result useful for treating allergies correlated with cedar pollen.

EXAMPLES

The invention will now be described with reference to exemplary embodiments of the invention. The following examples are intended to give the reader a better understanding of the construction and activity of the constructs of the invention, and should not be construed as a limitation on the scope of the invention.

Example 1: General Materials and Methods

Immunizations and Sera Collection

Six to eight week old female BALB/c mice were purchased from Harlan Laboratories, Frederick, Md. and maintained at our animal facility in Rockville, Md. The DNA immunizations were given either intramuscularly or intradermal with 50 ug of plasmid DNA in a volume of 100 ul of sterile PBS. Sera were obtained by orbital bleed and stored at −20° C. for later analysis. For sensitization, mice were injected with either 5 ug/ml of recombinant CRYJ2 (rCRYJ2) or recombinant CRYJ1 (rCYRJ1) together with 100 ul of alum (2 mg/ml) in a total volume of 200 ul. Mice were bled weekly and sera were analyzed for CRYJ specific antibodies by ELISA.

Guinea Pigs

Female Guinea pigs were purchased and housed at Spring Valley Laboratories (Woodline, Md.). The DNA immunizations were given intramuscularly with 100 ug of plasmid DNA in a volume of 200 ul of sterile saline. Sera were obtained by cardiac bleed and store at 20° C. for later analysis.

Detection of CYRJ2-Specific Immunoglobulin Responses

Nunc Maxisorp immunoassay plates were coated with rCRYJ2 at a concentration of 5 ug/ml in PBS overnight at 4° C. After blocking with 1% BSA in PBS, sera were diluted in PBS containing 0.05% Tween-20 (PBS-T) added and incubated for 1 hour. The IgG, IgG1, or IgG2a bound to the CRYJ2 immobilized on the wells was detected using peroxidase conjugated goat anti-mouse IgG, IgG1 or IgG2a antibodies (Jackson Laboratories). TMB substrate (KPL) was added and the enzymatic activity stopped with TMB Stop Solution. The plates were read at 450 nm. In some instances, Sure Stop Solution (KPL) was used and plates were read at 650 nm.

Preparation of Splenocytes for Cytokine Measurements

Spleens were removed aseptically and teased to prepare a single-cell suspension. To study the primary response, splenocytes were cultured in 24-well plates ($4\times10^5$ cells/well) in the presence or absence of 10 ug/ml, 5 ug/ml, or 2.5 ug/ml of rCRYJ2 for 72 hours.

Cytokine Assays

Supernatants were assayed for the presence of IFN-gamma and IL-4 by ELISA. Matched antibody pairs were used for IFN-gamma and IL-4 and done according to manufacturer's instructions. The standard curves were generated with mouse recombinant IFN-gamma and IL-4. All antibodies and cytokines were purchased from Invitrogen, Carlsbad, Calif. The detection limits of IFN-gamma and IL-4 assays were 20 and 10 pg/ml in respective.

Example 2: Expression of Allergens from Constructs

Figure 7:
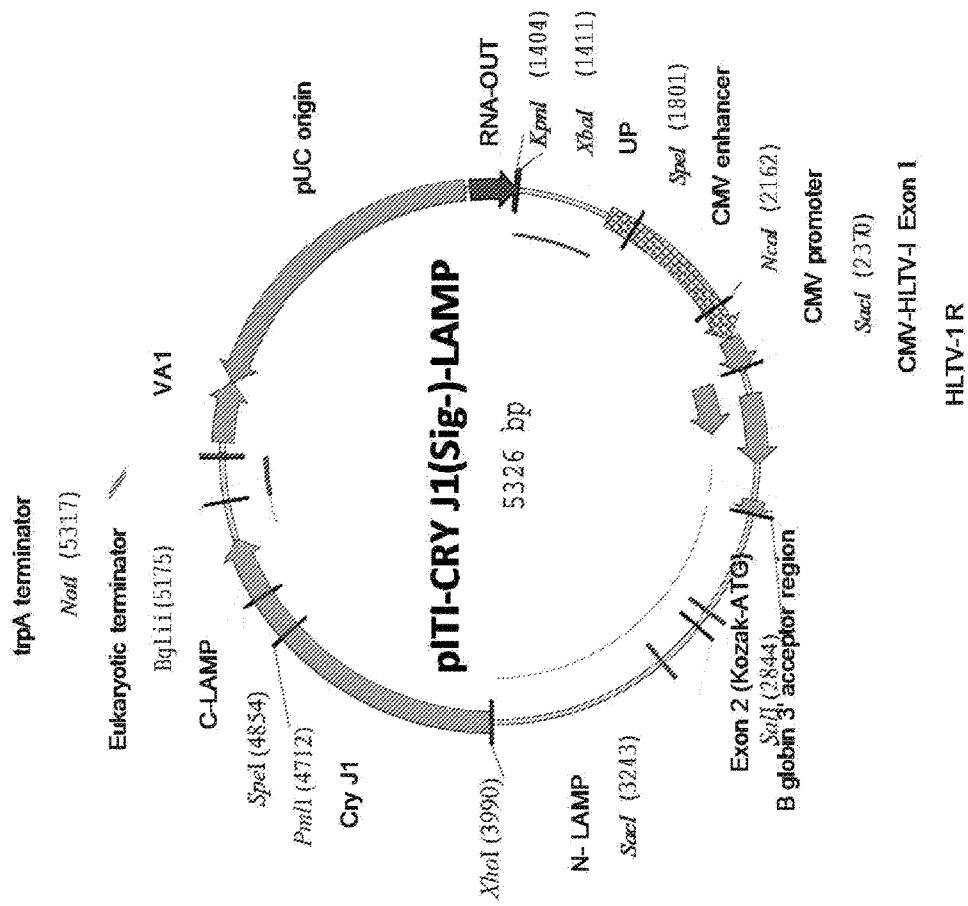
FIG. 7 shows a vector map of a nucleic acid according to the present invention, depicting the absence of the naturally-occurring signal sequence for the CryJ1 allergen sequence. This particular construct is used in experiments detailed below to show the importance of removal of the natural signal sequence of allergen sequences.
Figure 8:
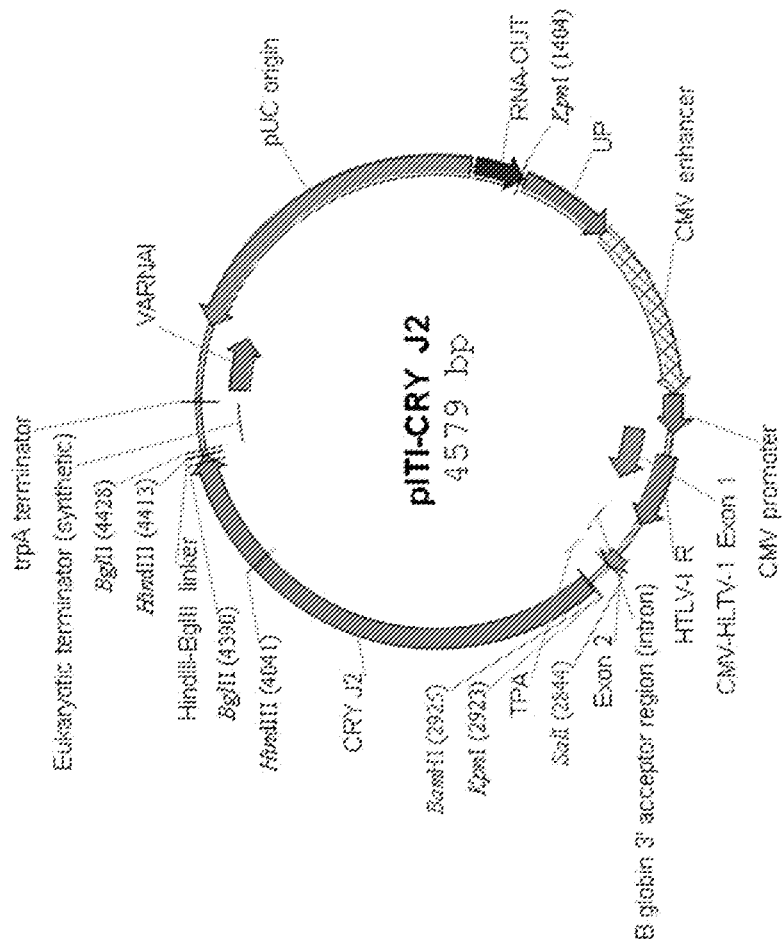
FIG. 8 shows a vector map of a nucleic acid construct not encompassed by the present invention, in which the CryJ2 allergen is encoded on a plasmid backbone, but in the absence of the SS, IOS, TM, and TG domains. This construct is used as a comparative control in experiments detailed below.

To show that the nucleic acid constructs of the invention can be used to express one or multiple allergens in transformed cells, human 293 cells were transfected with the CryJ2-LAMP plasmid, CryJ1+J2-LAMP plasmid (FIG. 4), CryJ1-LAMP plasmid, CryJ1 plasmid (lacking the CryJ1 signal sequence; FIG. 7), and the base plasmid vector alone (negative control; SEQ ID NO: 1). The results of the experiments are shown in FIG. 9.

Figure 9A:
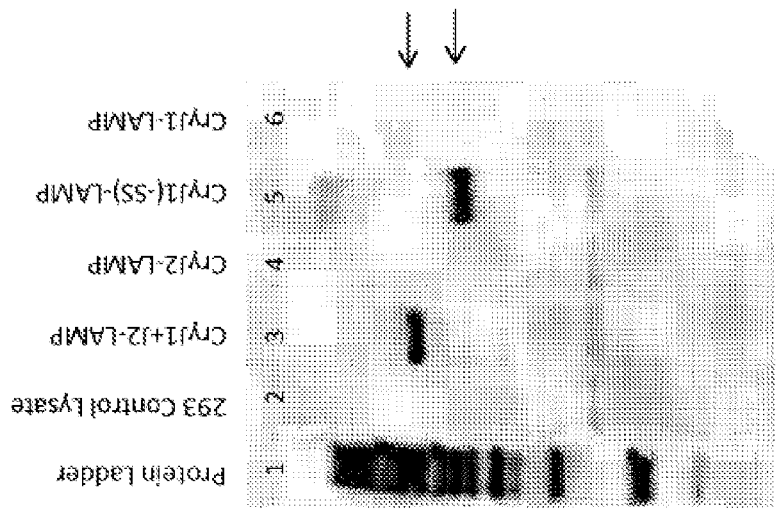
FIG. 9A and FIG. 9B show Western blots depicting expression of constructs according to the invention in 293 cells.

FIG. 9A shows the results of the transfection reactions, with detection using an anti-Cry J2 antibody. Briefly, thirty micrograms of cell lysate was electrophoresed, then transferred to a membrane for immunoblotting. Proteins were detected by immunoblotting with a CryJ2 monoclonal antibody, followed by chemiluminescence. As can be seen from the Figure, constructs comprising the CryJ2 allergen alone, and the CryJ1+CryJ2 allergens were detected (lanes 2 and 3), whereas other allergens were not. In this experiment, the naturally-occurring signal sequences for the CryJ1 and CryJ2 allergens were removed prior to the experiment, except for the construct in lane 5. These results show not only that the constructs of the invention are suitable for expression of allergens, but also that multiple allergens can be co-expressed.

Figure 9B:
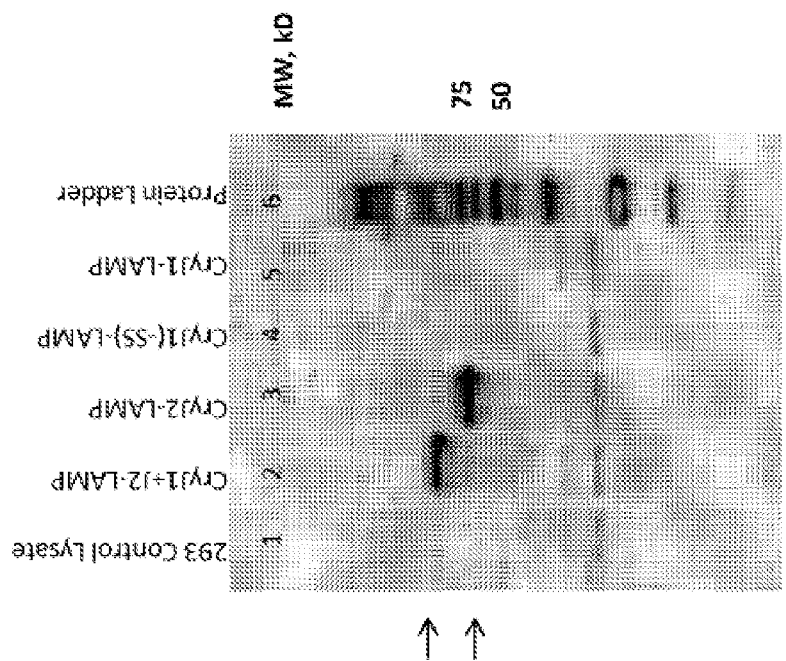
Figure 10A:
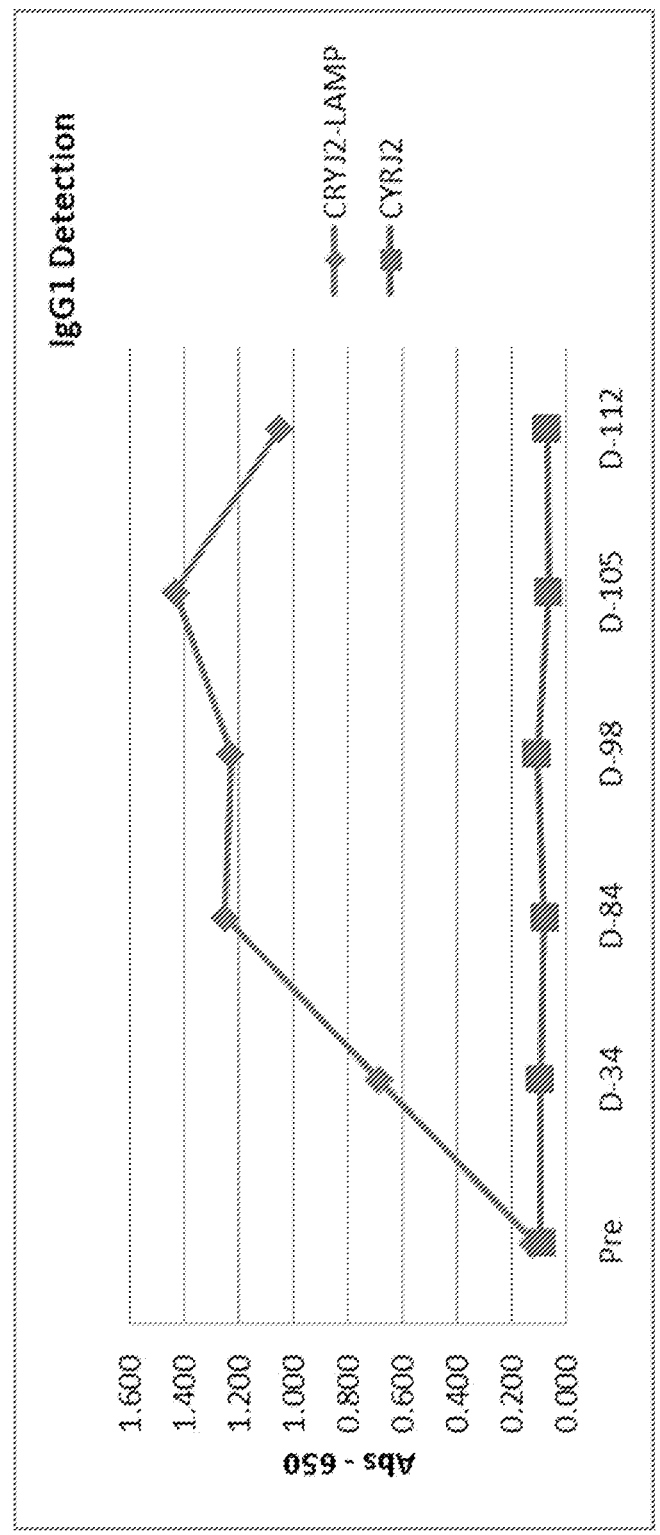
FIG. 10A and FIG. 10B show line graphs depicting the effectiveness of nucleic acid constructs according to the present invention as compared to other constructs comprising allergen sequences.
Figure 10B:
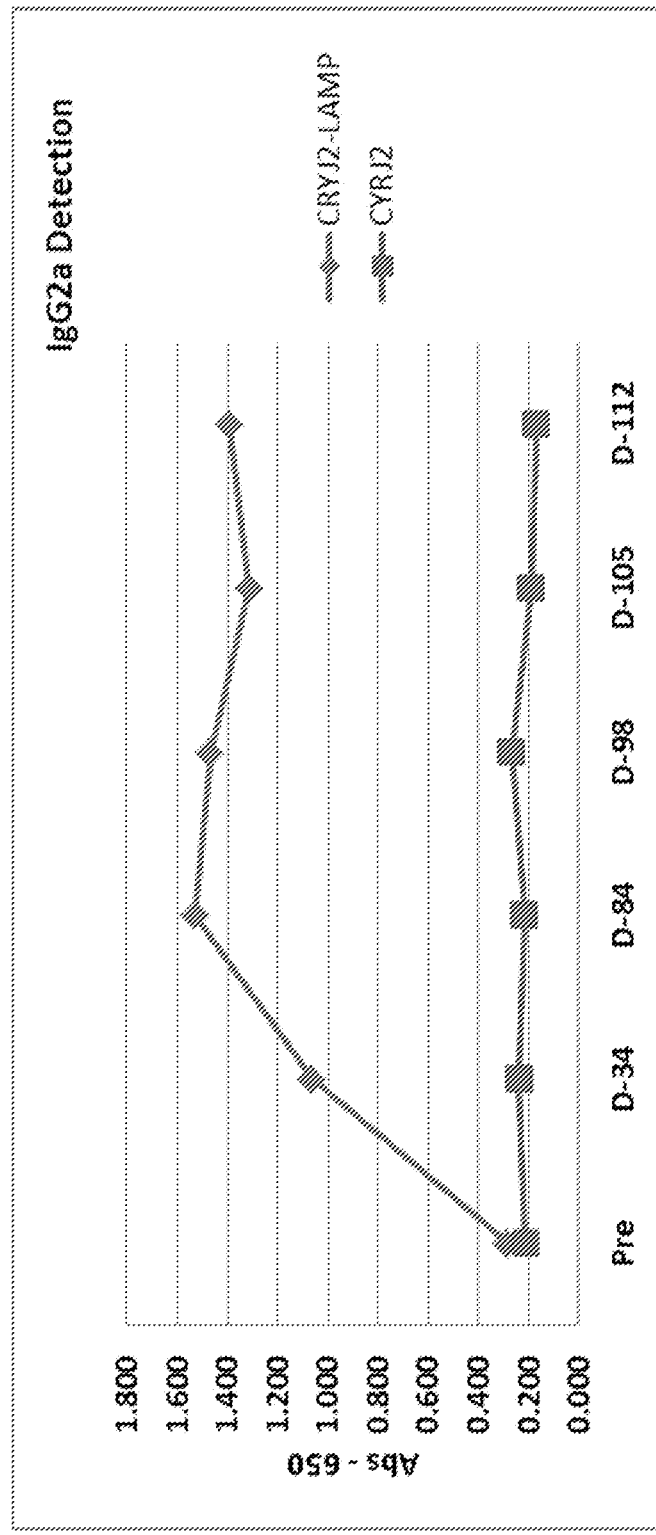
Figure 11A:
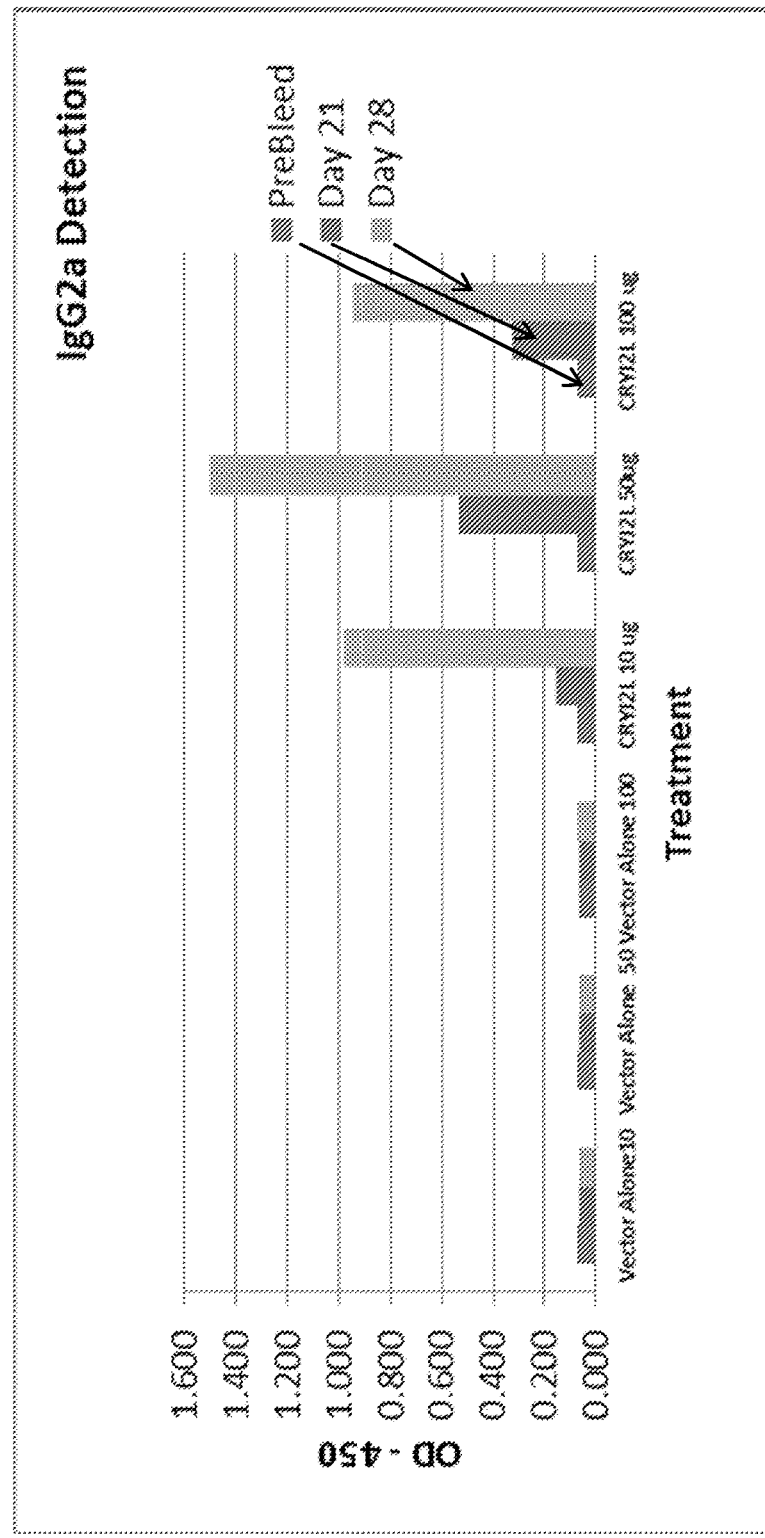
FIG. 11A and FIG. 11B depict bar graphs showing dosing effects of the CryJ2-LAMP construct in mice.
Figure 11B:
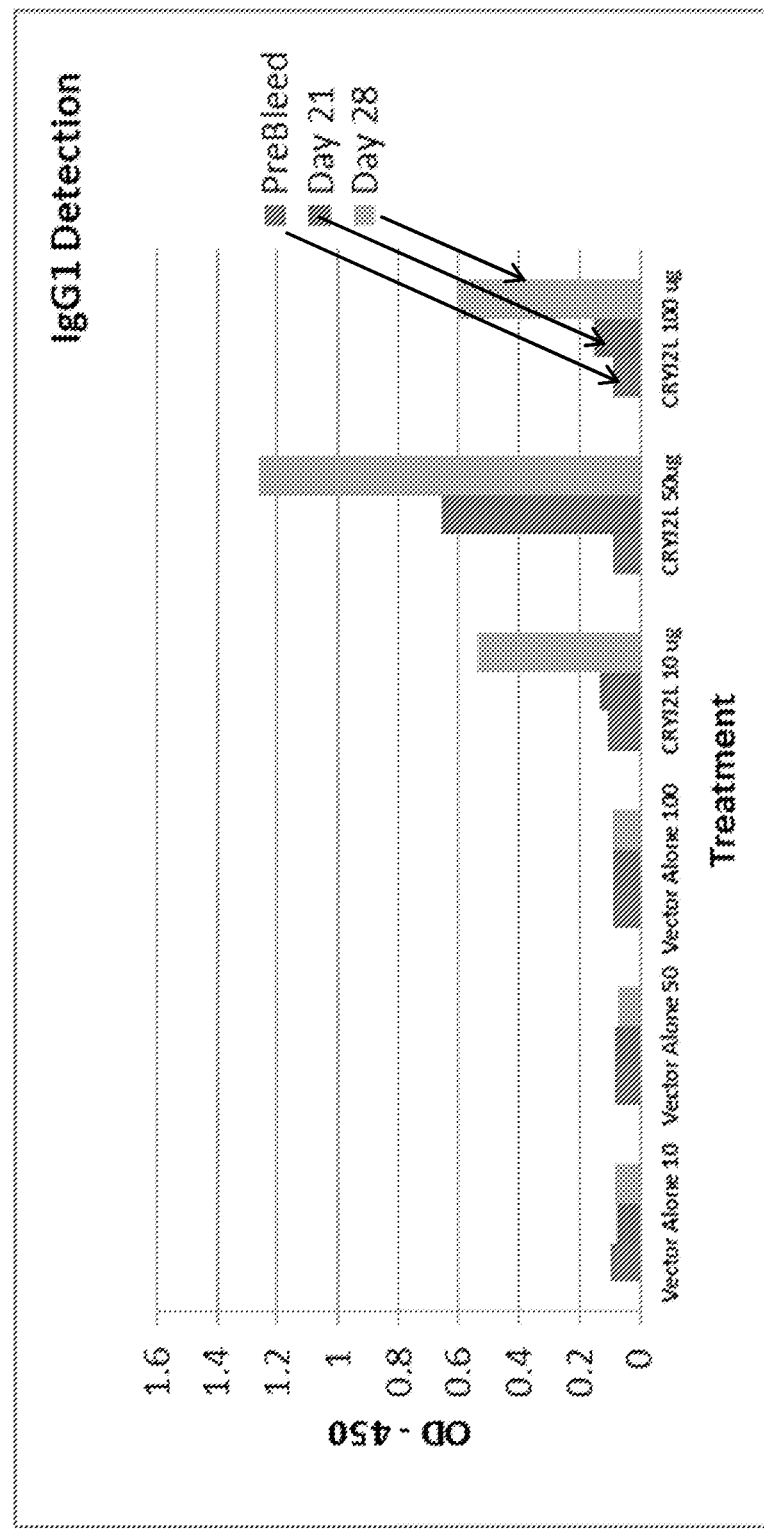

FIG. 9B shows the results of the transfection reactions, with detection using an anti-CryJ1 antibody. Briefly, thirty micrograms of cell lysate was electrophoresed, then transferred to a membrane for immunoblotting. Proteins were detected by immunoblotting with a CryJ1 monoclonal antibody, followed by chemiluminescence. As can be seen from the Figure, constructs comprising the CryJ1+CryJ2 allergens (lacking natural signal sequences) were detected (lane 3), as was the construct comprising the CryJ1 allergen in which the naturally-occurring signal sequence had been removed (lane 5). However, the construct in which the Cry1 allergen, which included its natural signal sequence, was not detected. These results show that the constructs of the invention are suitable for expression and detection of multiple allergens, and that removal of naturally-occurring signal sequences is important in expressing and detecting products.

Example 3: Data Supporting MHC II Processing Pathway for Constructs

To determine if chimeric proteins produced from the constructs of the invention are processed through the MHC II pathway, a set of experiments was performed to compare the immune response to the CryJ2 protein when administered as a coding region on a plasmid or as an allergen domain on a construct according to the present invention. The results are presented in FIGS. 10A and 10B.

More specifically, the figure shows the CryJ2 specific response following four DNA immunizations and crude pollen extract sensitization. Groups of mice (n=5) were immunized subcutaneously with either CRYJ2-LAMP plasmid DNA or CRYJ2 plasmid (see FIG. 8) DNA on days 0, 7, 14, and 21. Six weeks (day 77) following the last DNA immunization, the mice were sensitized with crude pollen extract in alum and given a booster three weeks (day 91) later. The data show the values generated from the pooled sera for each time point. IgG1 (FIG. 10A) and IgG2a (FIG. 10B) response in mice receiving CRYJ2-LAMP DNA remained elevated through day 112 and well above those mice that received CRYJ2 plasmid DNA that did not include LAMP. Delivery of allergens by way of constructs according to the invention thus provide a superior MHC II response than delivery of allergens without the context of the constructs of the invention.

Example 4: Dosing Rationales—Comparison of Immune Response to Different Doses of Constructs and to Vector Alone FIG. 11 shows a CryJ2-specific response following four DNA immunizations at different levels of dosing, for both IgG2a production and IgG1 production. Groups of mice (n=5) were given either 10 ug, 50 ug, or 100 ug of CRYJ2-LAMP plasmid DNA or Vector DNA intramuscularly on days 0, 7, 14, and 21. Three weeks following the last DNA immunization, the mice were sacrificed and spleens removed for Cytokine Induction assays.

The data show the values generated from the pooled sera for each vaccine dose. All three concentrations of CRYJ2-LAMP plasmid DNA gave IgG1 and IgG2a responses, with the 50 ug dose appearing to have given the highest antibody response. Vector alone, at any of the concentrations, did not induce any antibody response. These data show that there is a dose-dependent response for invoking an immune response, and that the immune response is, at least in part, an MHC II type response.

Example 5: Further Data Showing an Immune Response Via the MHC II Pathway

In this set of experiments, secretion of cytokines in supernatants of stimulated spleen cells was determined using IL-4 and IFN-gamma as markers. Specifically, spleen cells of mice (n=3) were harvested at day 42 and cultured in the presence of 10 ug/ml, 5 ug/ml, 2.5 ug/ml, or no rCRYJ2. Spleen cells from naive mice were used as a negative control. IL-4 and IFN-gamma levels of rCRYJ2 stimulated splenocytes were measured by ELISA in pg/ml.

The data are presented in FIGS. 12A and 12B. The data show that mice receiving 50 ug of CRYJ2-LAMP plasmid DNA had a significantly higher expression of IFN-gamma (an established biomarker for activation of the MHC II immune response pathway) than those receiving the lower dose of plasmid DNA. There was very little response seen of IL-4 levels in any of the groups, an established biomarker for the MHC I pathway. There was also very little response, if any, with IL-5 (data not shown). These results indicate that Cry J2-LAMP DNA immunization induced the recruitment of Th1 memory cells and not Th2 cells, as indicated by the production of IFN-gamma and not IL-4 after stimulation with the recombinant Cry J2 protein.

Example 6: Studies on the Therapeutic Effect of Immunization with CryJ2-LAMP DNA Vaccine in Previously CryJ2 Sensitized Mice To study the therapeutic effects of the DNA-LAMP-CryJ2 vaccine, groups of mice (n=5) were sensitized with three injections of 5 ug of rCRYJ2 recombinant protein and four weeks later, treated with four injections of CRYJ2-LAMP plasmid DNA given in a weekly (7 day) intervals. The DNA immunizations induced a booster effect for IgG2a and a transient increase for IgG1 antibodies indicating a Th1-directed modulatory effect of the DNA vaccine. Two additional DNA immunizations on days 167 and 174 boosted the CRYJ2 specific IgG2a response and almost no change in IgG1 response. Visual examination of the mice revealed no physical distress or skin reactions. There were also no changes in appetite nor did they appear lethargic. The effects on IgG1 and IgG2a titers are shown in FIGS. 13A and 13B, respectively.

Example 7: Induction of IFN-Gamma and IL-4 in Mouse Spleen Cell Cultures

The therapeutic effect of CryJ2-LAMP DNA vaccine was also studied in terms of cytokine induction. Spleen cells of mice (n=3) were harvested at day 183 and stimulated with varying concentrations of rCRYJ2. Spleen cells from naive mice were used as a negative control. IL-4 and IFN-gamma levels of rCRYJ2 stimulated splenocytes were measured by ELISA in pg/ml. Significantly elevated expression of IFN-gamma was detected in the CRYJ2-LAMP vaccinated group compared with that in the vector group. However, IL-4 expression showed no difference from the vector group. The increase in IFN-gamma as a result of Cry J2-LAMP DNA immunization presumably involves the recruitment of antigen-specific Th1 cells and the creation of a Th1 cytokine milieu. Data obtained from this experiment is presented in FIGS. 14A and 14B.

Example 8: Detection of Circulating CryJ2 Protein in Sera

Figure 12A:
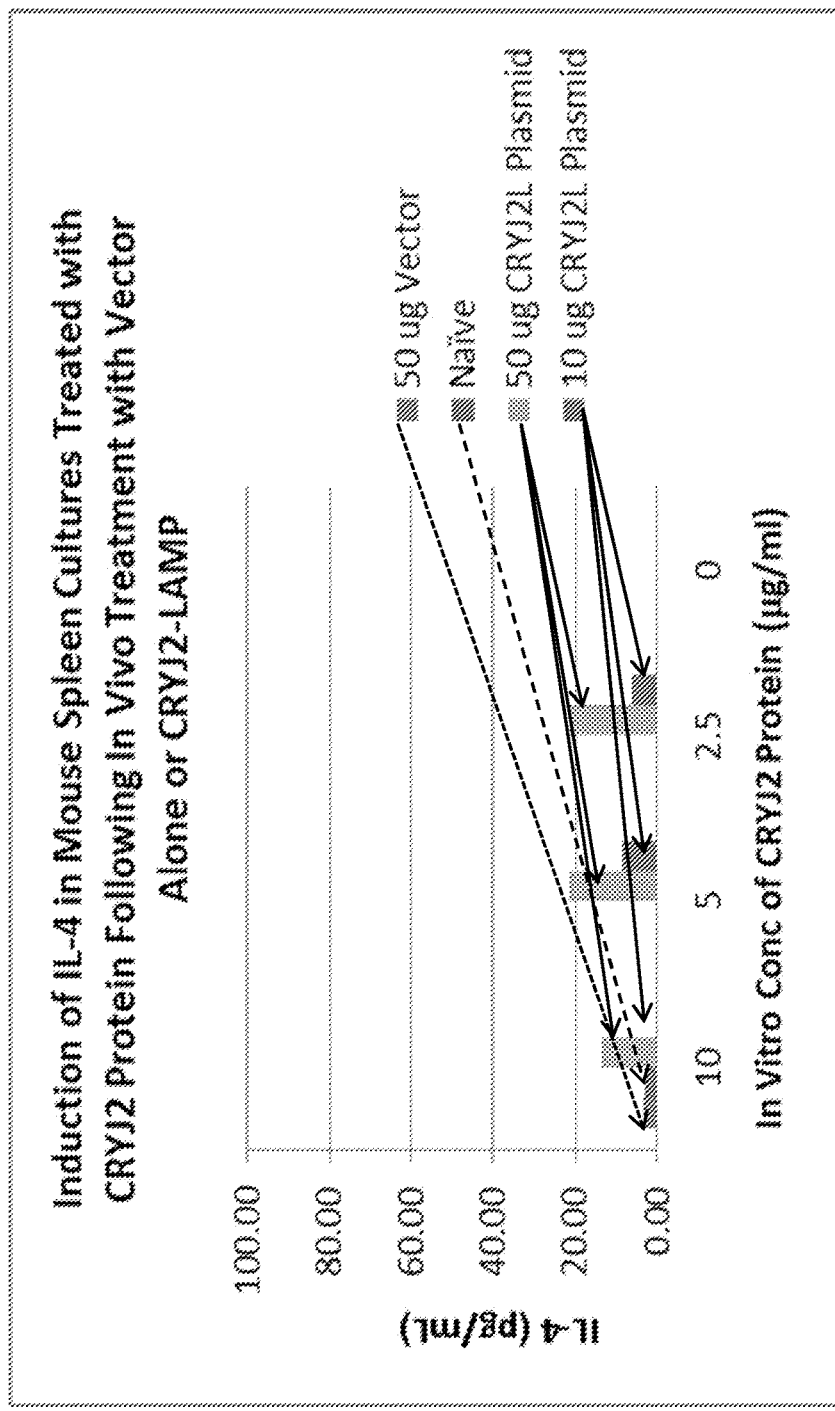
FIG. 12A and FIG. 12B depict bar graphs showing the effect on induction of IL-4 and IFN-gamma in mouse spleen cultures treated with the CryJ2-LAMP construct of the invention as compared to vector alone.
Figure 12B:
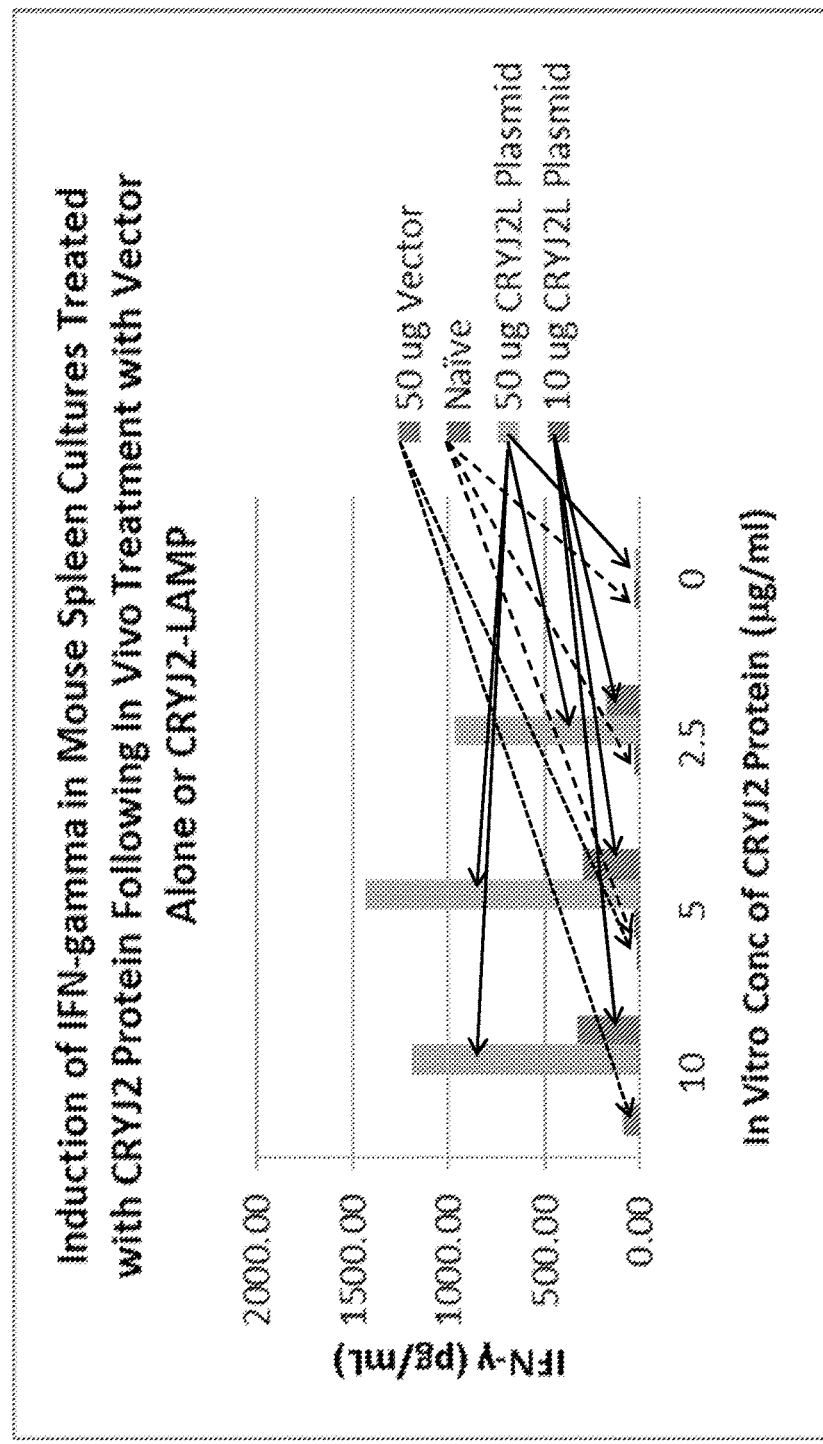
Figure 13A:
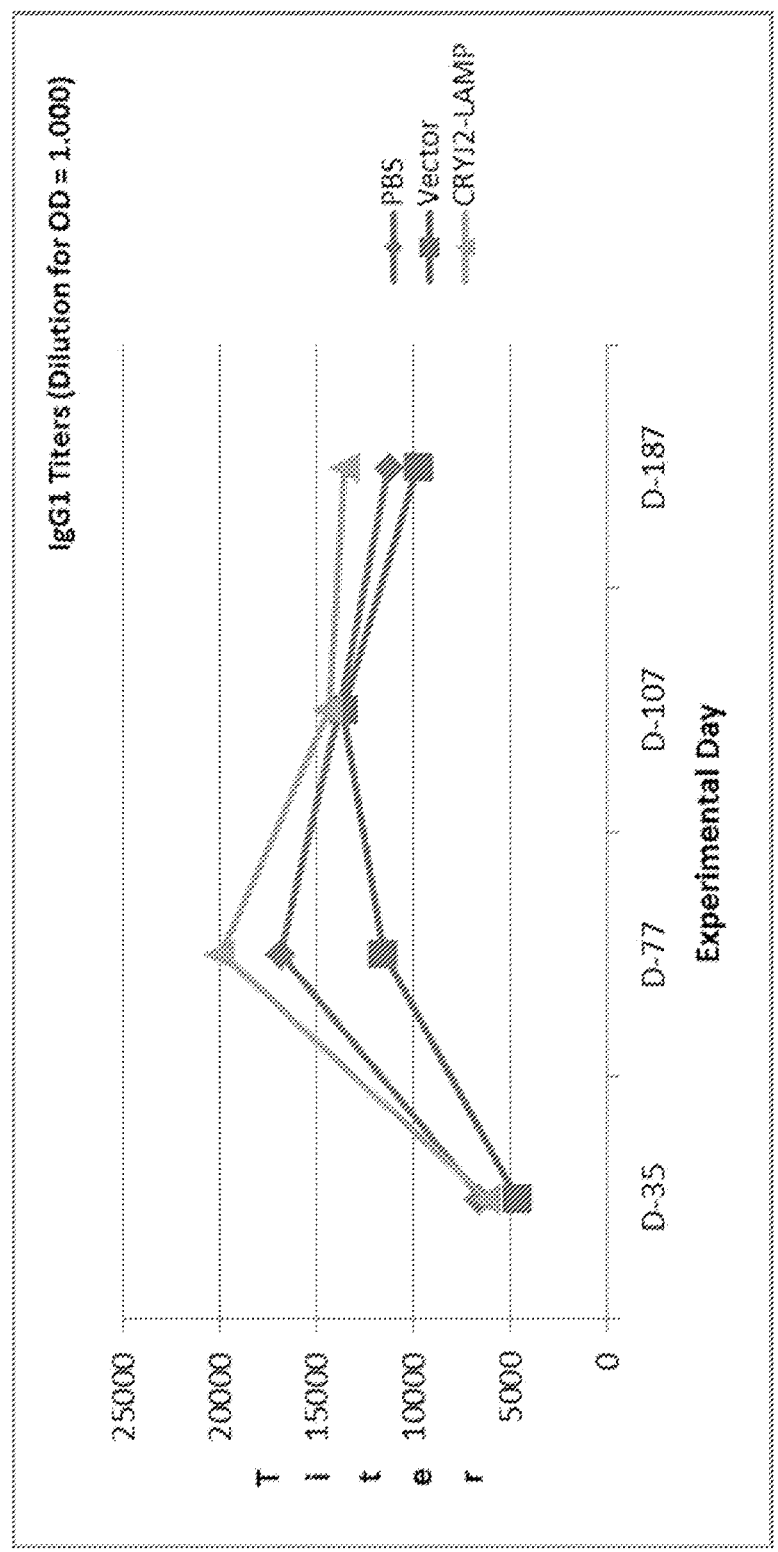
FIG. 13A and FIG. 13B depict line graphs showing the effectiveness of immunization of previously sensitized mice with the CryJ2-LAMP DNA vaccine.
Figure 13B:
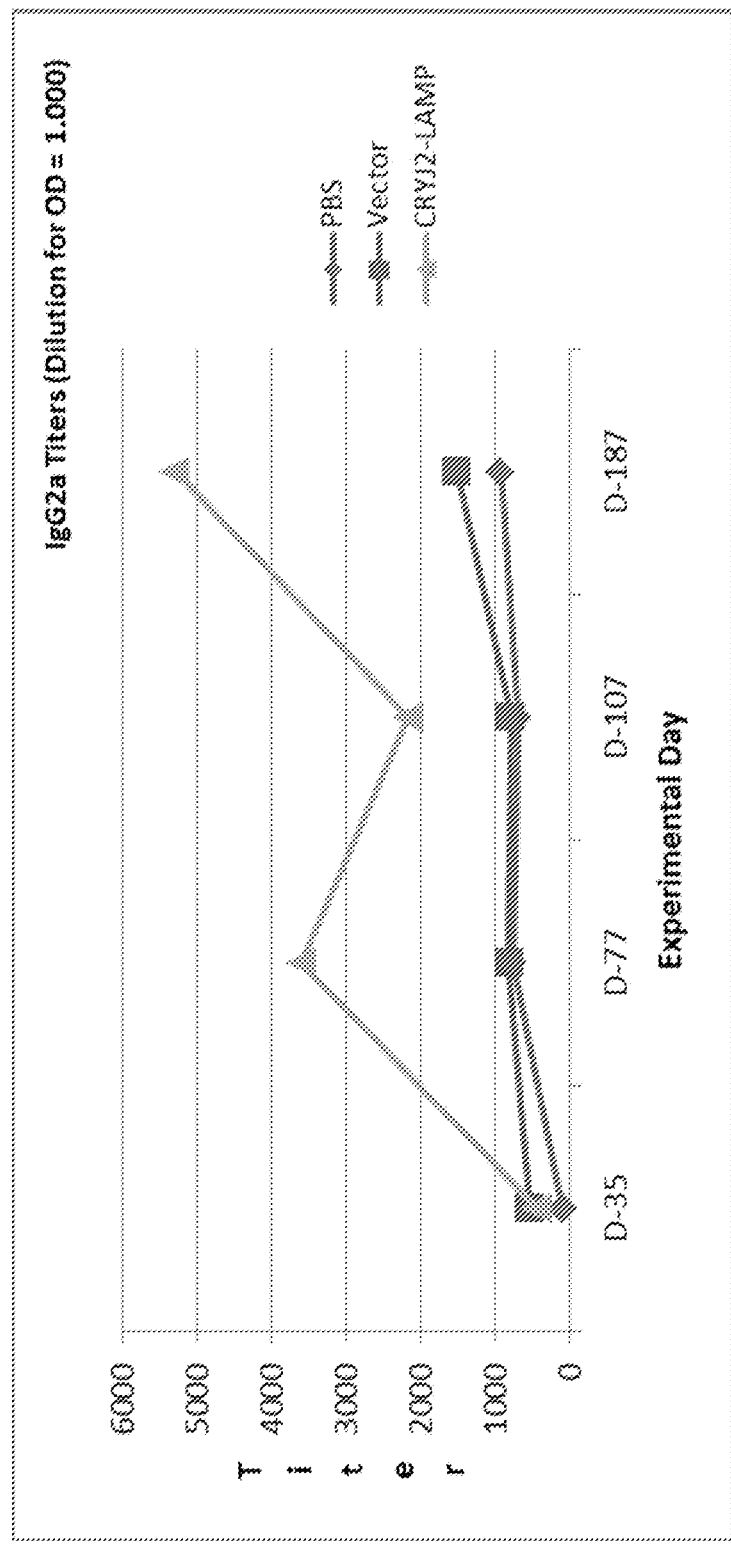
Figure 14A:
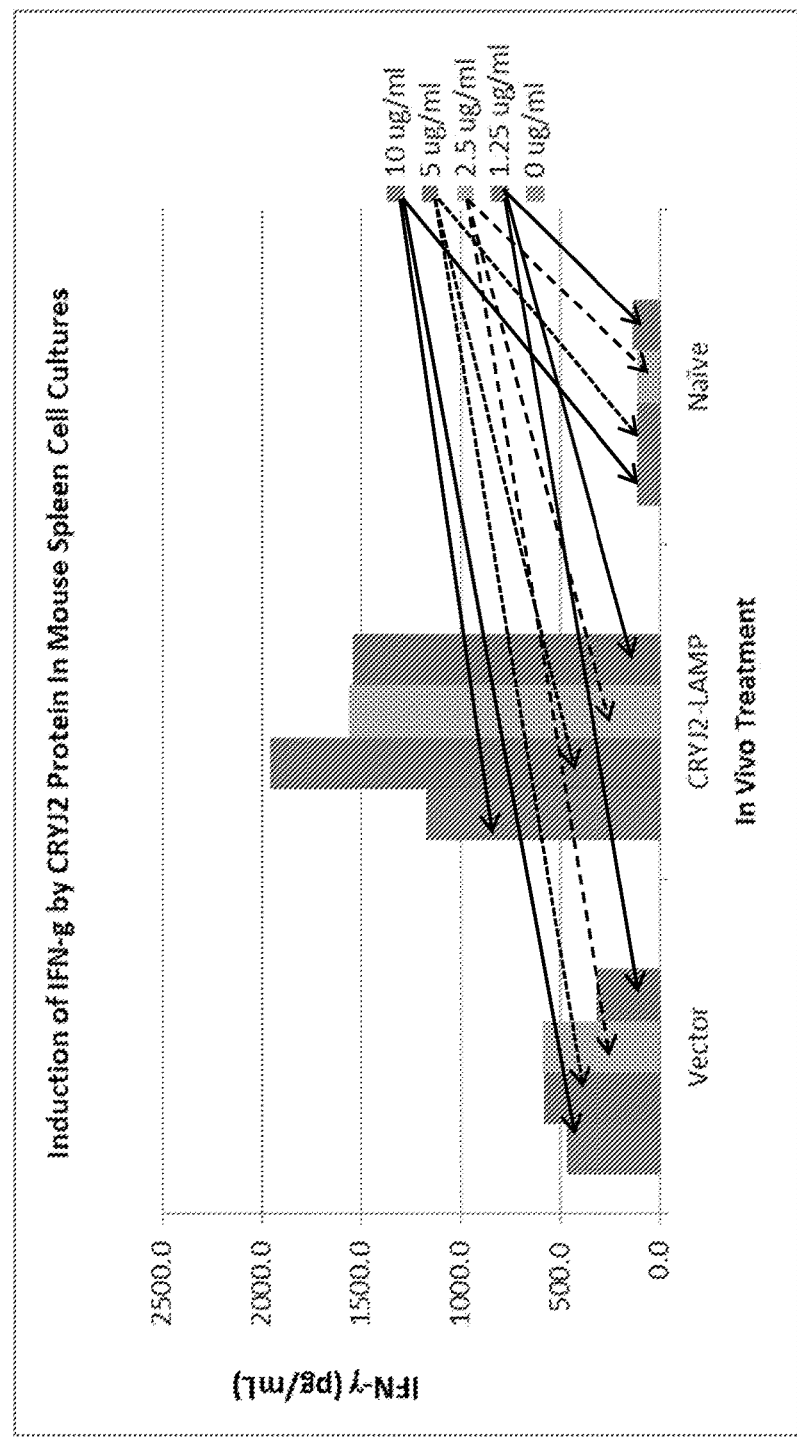
FIG. 14A and FIG. 14B depict bar graphs showing induction of IFN-g (FIG. 14A) and IL-4 (FIG. 14B) in mouse spleen cell cultures.
Figure 14B:
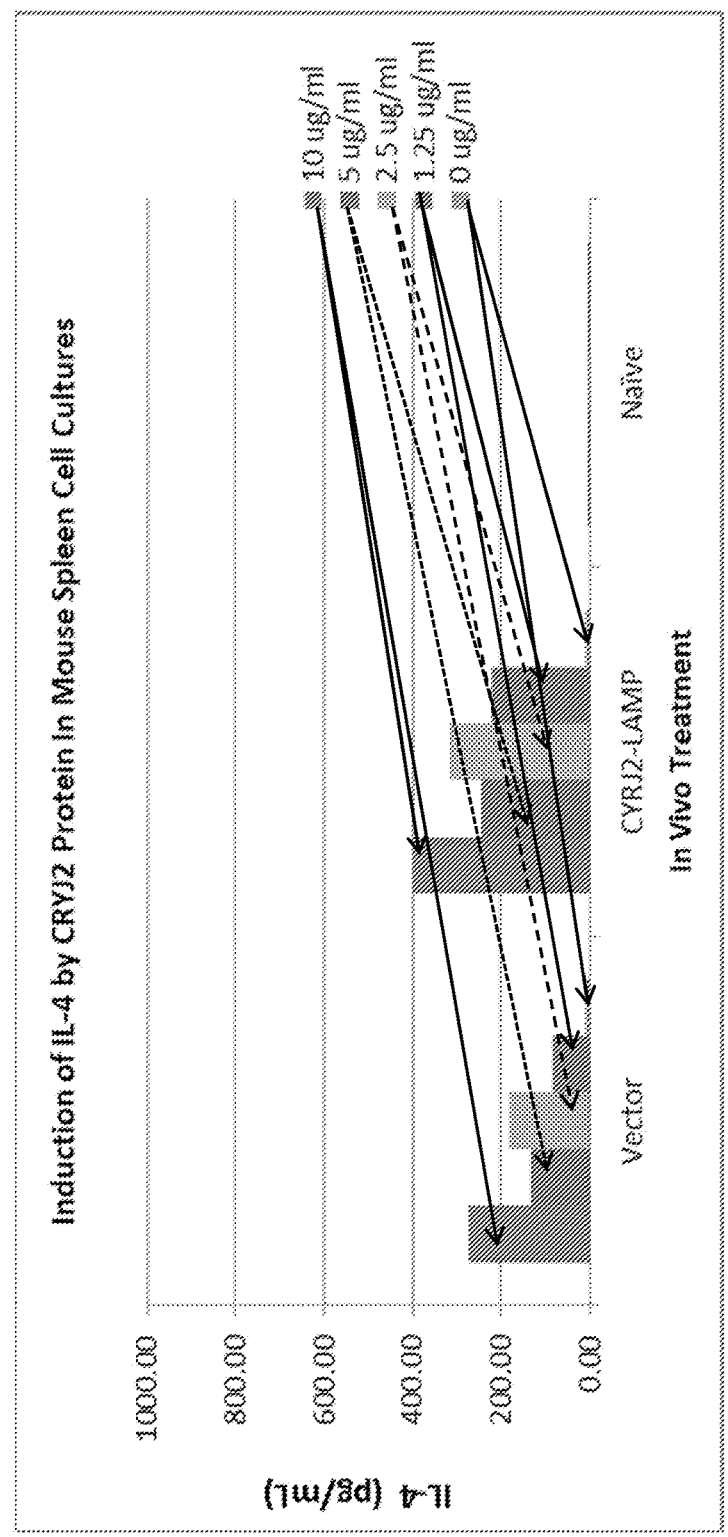
Figure 15:
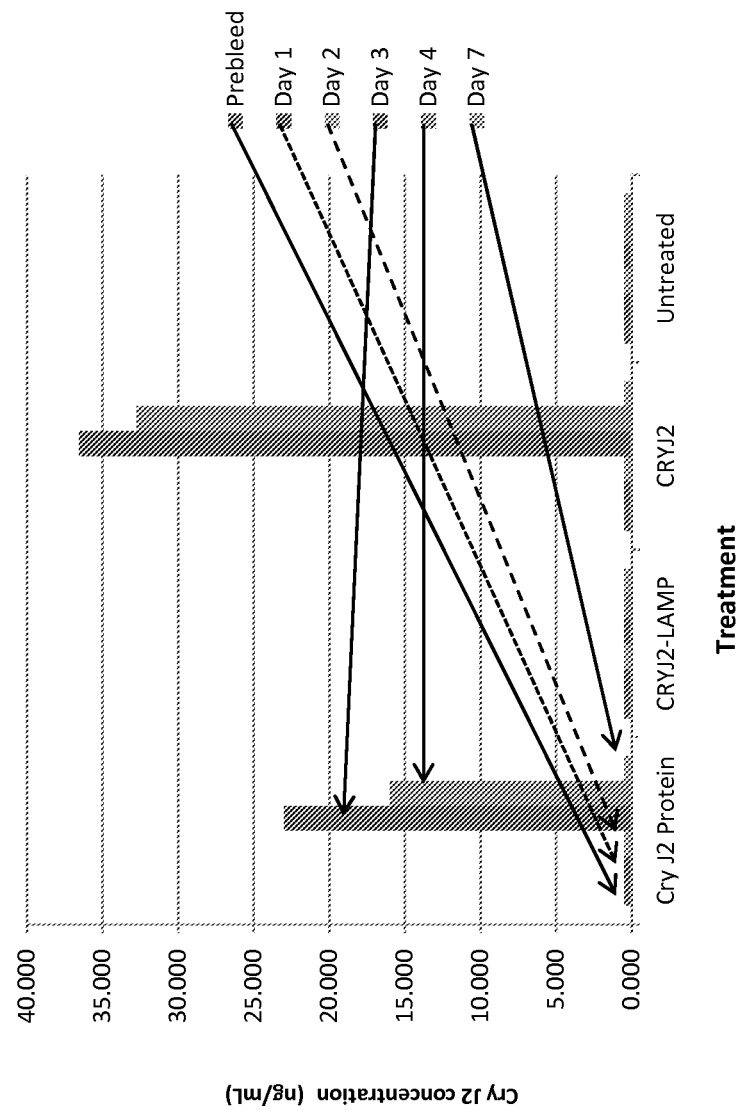
FIG. 15 depicts a bar graph showing quantitation of circulating CryJ2 protein in immunized mice.

Mice were immunized with Cry J2 protein, pDNA-Cry J2 (no LAMP) and Cry J2-LAMP-vax. Serum samples were taken at days 0, 1, 2, 3, 4, and 7 and evaluated for the presence of free Cry J2 protein in a sensitive sandwich immunoassay. Free Cry J2 was detected in the protein and non-LAMP immunization. However, no free allergen was detected in any time point in any experiment with Cry J2-LAMP-vax immunized mice (minimum detectable level 2 ng/ml). Data supporting these statements are provided in FIG. 12.

LAMP vaccines according to the invention will be the only formulations that treat allergies without introducing free allergen into the patient systemically. This is unlike traditional immunotherapy which can sometimes result in anaphylactic reactions due to systemic introduction of allergen. This experiment shows that mice which received the Cry J2-LAMP DNA plasmid did not have free Cry J2 protein and thus not released into the systemic circulation as seen with mice given protein alone or Cry J2 DNA without LAMP.

Example 9: Effectiveness of DNA Vaccines in Guinea Pigs

Figure 16A:
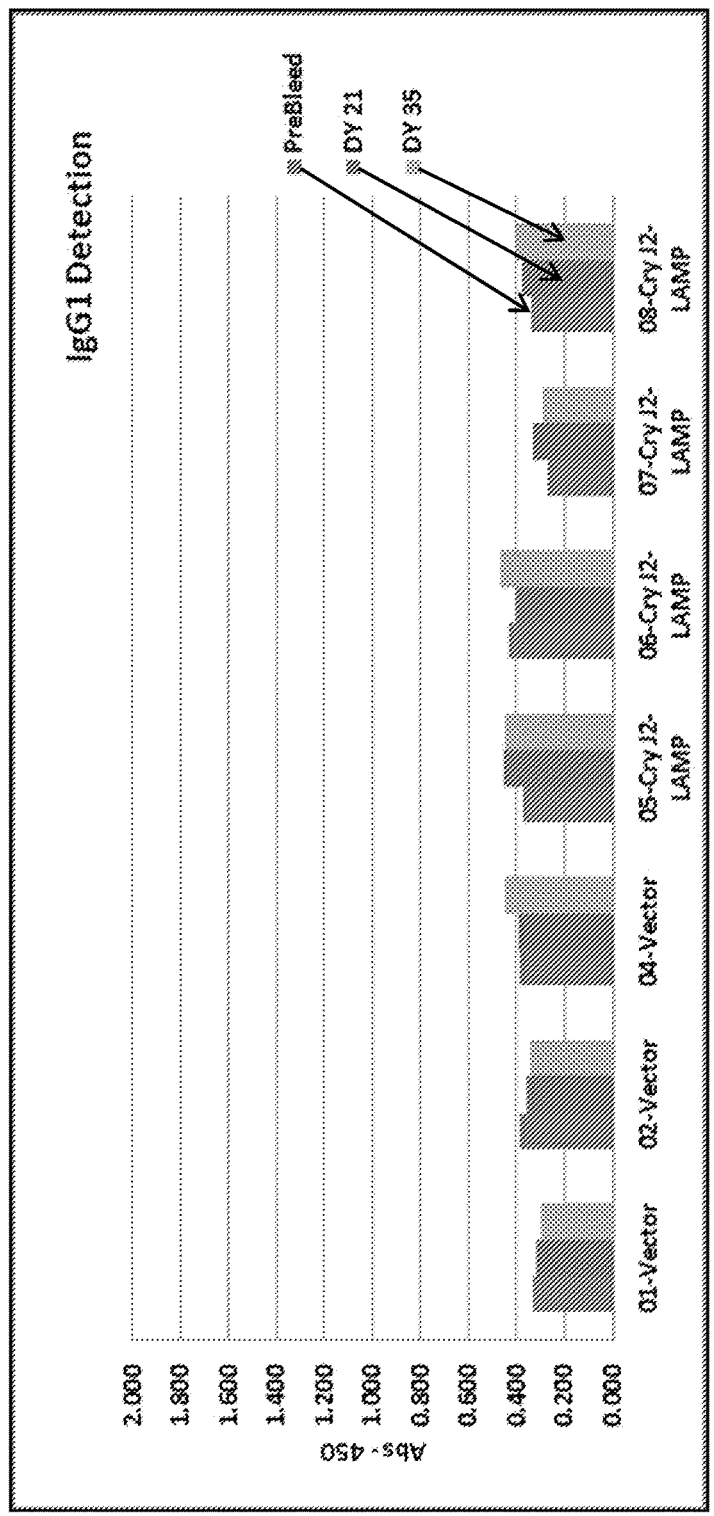
FIG. 16A and FIG. 16B depict bar graphs of guinea pig data, showing IgG1 detection (FIG. 16A) and IgG2 detection (FIG. 16B) for guinea pigs immunized with the CryJ2-LAMP construct and challenged with recombinant CryJ2.
Figure 16B:
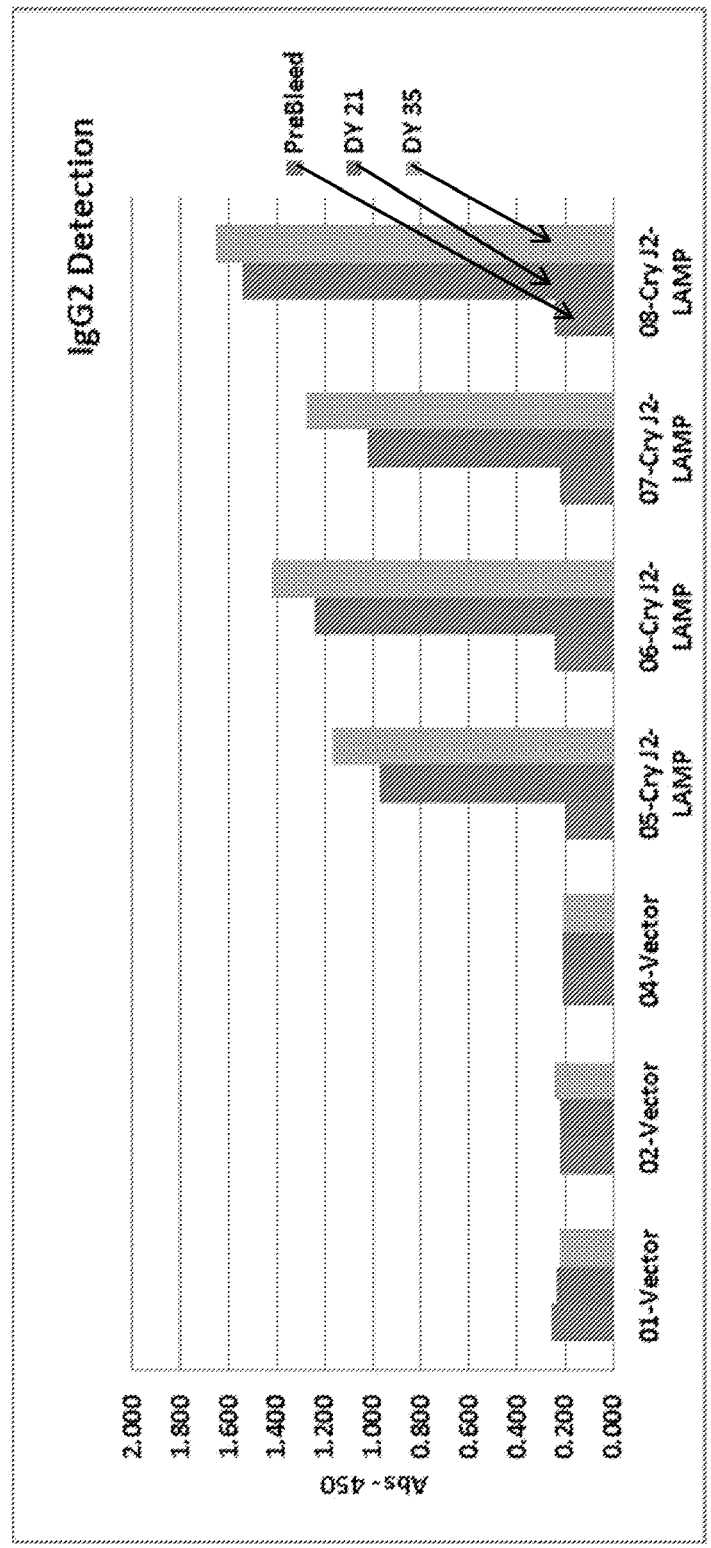

To expand the scientific understanding of the function of the present nucleic acid constructs in other mammals, studies were performed in female guinea pigs immunized with the CryJ2-LAMP DNA vaccine, then challenged with recombinant CryJ2 protein. The results of the studies are shown in FIGS. 16A and 16B.

Specifically, female guinea pigs received intramuscular injections of 100 ug of CRYJ2-LAMP DNA Vaccine or vector alone on days 0, 7, and 14. Four weeks following the last DNA vaccine immunization on day 14, the guinea pigs received subcutaneous injections of 10 ug/ml of rCRYJ2 protein/alum on days 42 and 49. Serum samples were obtained from guinea pigs on days 0, 21, 35, 63, and 77. The data show that the mean absorbance values for the guinea pigs receiving CRYJ2-LAMP DNA increased through day 35 for IgG2 with little or no IgG1 response. The increase in IgG2a is consistent with what is typically seen in a Th1 biased response.

Figure 17:
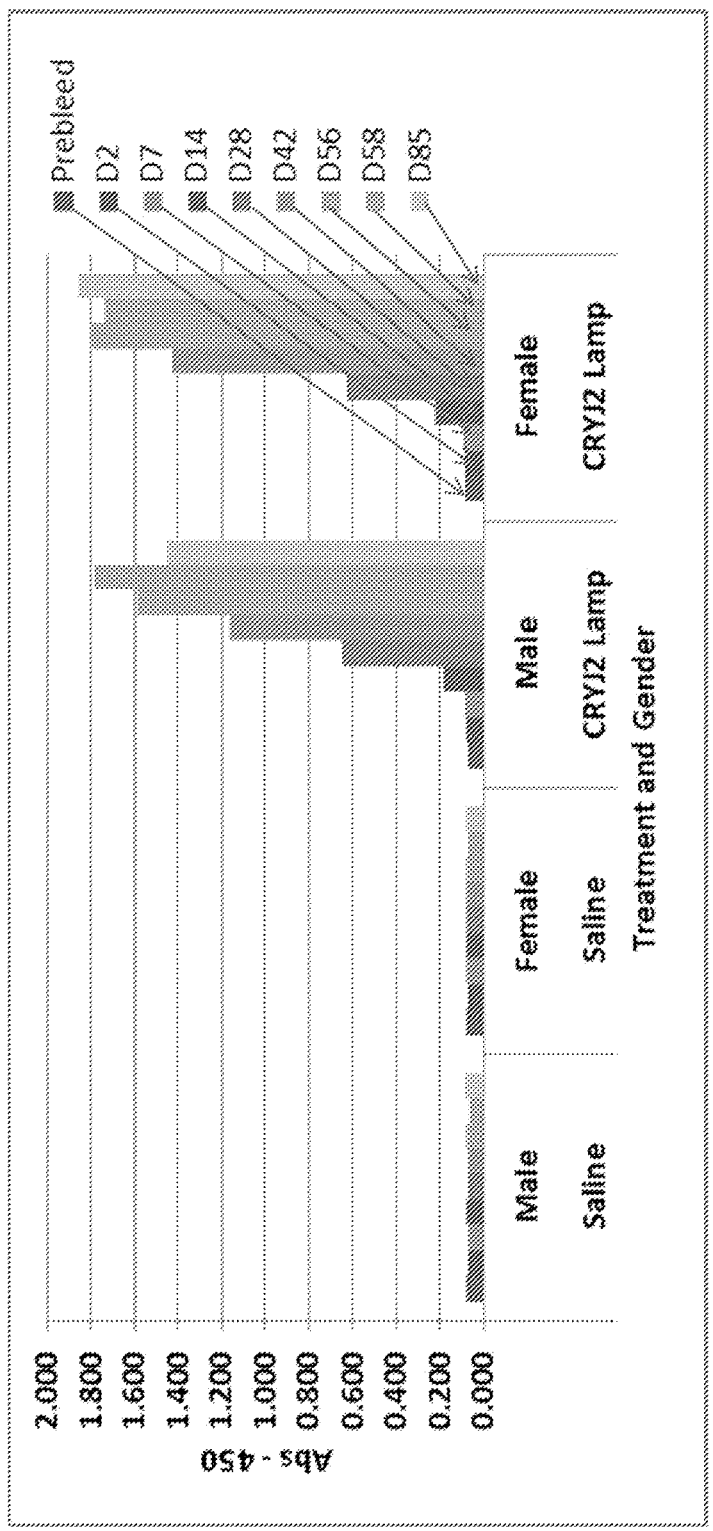
FIG. 17 depicts a bar graph showing the Anti-CryJ2 response in New Zealand white rabbits immunized with CryJ2-LAMP DNA vaccine during an 85 day toxicology GLP safety study.

Example 10: Further Investigation in Other Mammals—Toxicology Data Showing Safety New Zealand White rabbits received intramuscular injections of 4.128 mg of CRYJ2-LAMP DNA. Age and gender-matched control rabbits received saline alone. Rabbits were immunized on days 1, 14, 28, 42, and 56. Serum samples were obtained from rabbits on days 1, 14, 28, 42, 56, 58, and 85. Mean absorbance values of rabbit serum at 1:100 following multiple IM injections of CryJ2-LAMP plasmid or saline are shown in FIG. 17. As can be seen from the Figure, the data show that the mean absorbance values for the rabbits receiving saline are less than 0.100. The absorbance values of rabbits in the groups treated with CRYJ2-LAMP DNA generally increased through day 42 and in some cases increased through day 85.

Example 11: Applicability to Food Allergies

Over the last 25 years, 8 significant peanut allergens have been identified based on sensitization in peanut allergic patients. Three major peanut allergens are most commonly recognized by IgE of peanut allergic individuals: 65-100% recognize Ara h1, a 63.5 kDa seed storage vicilin family protein; 71-100% recognize Ara h2, a 17 kDa seed storage conglutin family protein; and 45-95% recognize Ara h3, a 14 kDa seed storage glycinin family protein. In addition to being a common causative agent in triggering peanut-dependent allergic reactions and anaphylaxis, these three proteins also appear to promote stronger allergic reactions. Targeting these allergens as the basis for peanut allergy immunotherapy has the potential of providing the broadest protection from strong allergic reactions among the diverse population of peanut allergies. Phase I clinical trials are currently underway that use hypo allergenic forms of the three major allergens and a heat killed bacterium adjuvant as allergy immunotherapy. This trial is ongoing, but the eventual commercialization of such a therapy will be a challenge due to a highly complex manufacturing process.

Figure 6B:
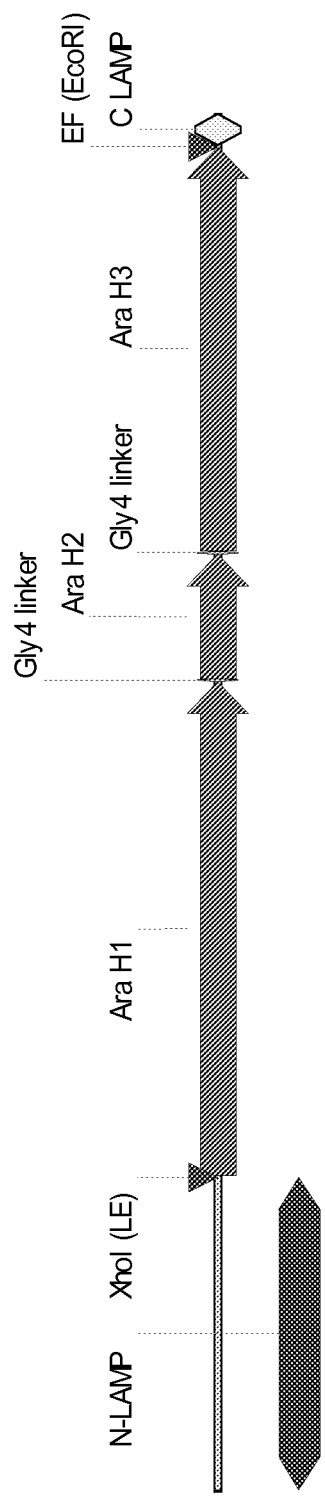
FIG. 6B shows a schematic of the protein encoded by the nucleic acid of FIG. 6A.

To address the rising incidence of food allergies, and in particular peanut allergy, a nucleic acid construct according to the invention was created. The construct is depicted in FIG. 6A, and a schematic of the encoded chimeric protein is depicted in FIG. 6B, as discussed above. This construct can be used to generate a predominantly MHC II response in subjects to which it is administered. The presence of the three most common peanut allergens in a single chimeric protein allows for a broad immunization, which will treat the vast majority of peanut allergies in the population.

Figure 18:
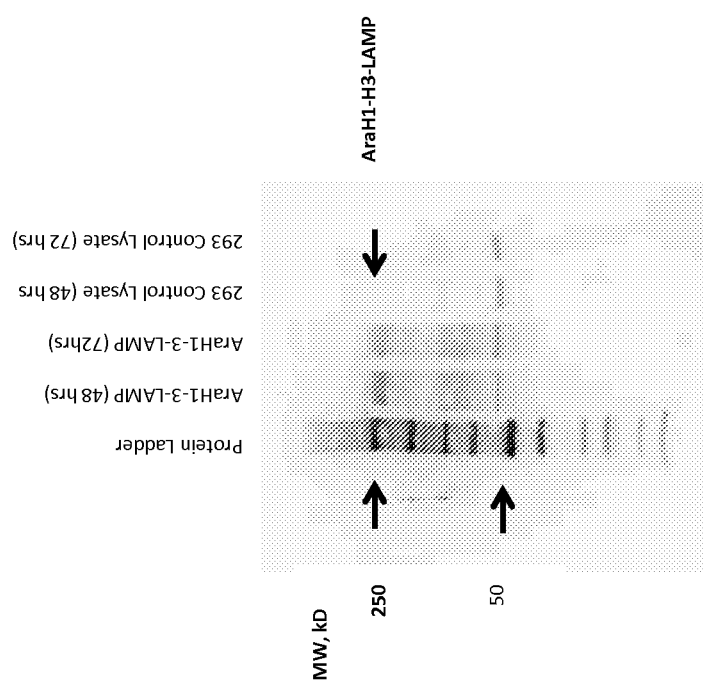
FIG. 18 depicts a Western blot showing co-expression of peanut allergens H1, H2, and H3 from a construct according to the present invention.

The construct was expressed and the results shown in FIG. 18. FIG. 19 shows that all three allergens can be expressed and detected as a single poly-protein on Western blots.

It will be apparent to those skilled in the art that various modifications and variations can be made in the practice of the present invention and in construction of the nucleic acid constructs without departing from the scope or spirit of the invention. Other embodiments of the invention will be apparent to those skilled in the art from consideration of the specification and practice of the invention. It is intended that the specification and examples be considered as exemplary only, with a true scope and spirit of the invention being indicated by the following claims.

Further Sequences for Sequence Listing

In addition to the sequences provided in the formal Sequence Listing provided as part of this application, the following sequences comprise part of the present disclosure:

1. The nucleotide sequence of the coding region for the Cry 1-Cry2-LAMP chimeric construct, as follows:

2.

```
Cry J1 + J2-LAMP
                                                          SEQ ID NO: 6
ccgcctaatg agcgggcttt tttttcttag ggtgcaaaag gagagcctgt aagcgggcac    60
tcttccgtgg tctggtggat aaattcgcaa gggtatcatg gcggacgacc ggggttcgag   120
ccccgtatcc ggccgtccgc cgtgatccat gcggttaccg cccgcgtgtc gaacccaggt   180
```

-continued

```
gtgcgacgtc agacaacggg ggagtgctcc ttttggcttc cttccccttc ttccgcttcc    240
tcgctcactg actcgctgcg ctcggtcgtt cggctgcggc gagcggtatc agctcactca    300
aaggcggtaa tacggttatc cacagaatca ggggataacg caggaaagaa catgtgagca    360
aaaggccagc aaaaggccag gaaccgtaaa aaggccgcgt tgctggcgtt tttccatagg    420
ctccgccccc ctgacgagca tcacaaaaat cgacgctcaa gtcagaggtg gcgaaacccg    480
acaggactat aaagatacca ggcgtttccc cctggaagct ccctcgtgcg ctctcctgtt    540
ccgaccctgc cgcttaccgg atacctgtcc gcctttctcc cttcgggaag cgtggcgctt    600
tctcatagct cacgctgtag gtatctcagt tcggtgtagg tcgttcgctc caagctgggc    660
tgtgtgcacg aacccccccgt tcagcccgac cgctgcgcct tatccggtaa ctatcgtctt    720
gagtccaacc cggtaagaca cgacttatcg ccactggcag cagccactgg taacaggatt    780
agcagagcga ggtatgtagg cggtgctaca gagttcttga agtggtggcc taactacggc    840
tacactagaa gaacagtatt tggtatctgc gctctgctga agccagttac cttcggaaaa    900
agagttggta gctcttgatc cggcaaacaa accaccgctg gtagcggtgg ttttttttgtt    960 tgcaagcagc agattacgcg cagaaaaaaa ggatctcaag aagatccttt gatcttttct   1020
acggggtctg acgctcagtg gaacgaaaac tcacgttaag ggattttggt catgagatta   1080
tcaaaaagga tcttcaccta gatccttttta aattaaaaat gaagttttaa atcaatctaa   1140
agtatatatg agtaaacttg gtctgacagt taccaatgct taatcagtga ggcacctatc   1200
tcagcgatct gtctatttcg ttcatccata gttgcctgac tcctgcaaac cacgttgtgg   1260
tagaattggt aaagagagtc gtgtaaaata tcgagttcgc acatcttgtt gtctgattat   1320 tgattttttgg cgaaaccatt tgatcatatg acaagatgtg tatctacctt aacttaatga   1380
ttttgataaa aatcattagg taccccggct ctagatggca tgacattaac ctataaaaat   1440
aggcgtatca cgaggccctt tcgtctcgcg cgtttcggtg atgacggtga aaacctctga   1500
cacatgcagc tcccggagac ggtcacagct tgtctgtaag cggatgccgg gagcagacaa   1560
gcccgtcagg gcgcgtcagc gggtgttggc gggtgtcggg gctggcttaa ctatgcggca   1620
tcagagcaga ttgtactgag agtgcaccat atgcggtgtg aaataccgca cagatgcgta   1680
aggagaaaat accgcatcag attggctatt ggccattgca tacgttgtat ccatatcata   1740
atatgtacat ttatattggc tcatgtccaa cattaccgcc atgttgacat tgattattga   1800
ctagttatta atagtaatca attacggggt cattagttca tagcccatat atggagttcc   1860
gcgttacata acttacggta aatggcccgc ctggctgacc gcccaacgac ccccgcccat   1920
tgacgtcaat aatgacgtat gttcccatag taacgccaat agggactttc cattgacgtc   1980
aatgggtgga gtatttacgg taaactgccc acttggcagt acatcaagtg tatcatatgc   2040
caagtacgcc ccctattgac gtcaatgacg gtaaatggcc cgcctggcat tatgcccagt   2100
acatgacctt atgggacttt cctacttggc agtacatcta cgtattagtc atcgctatta   2160
ccatggtgat gcggttttgg cagtacatca atgggcgtgg atagcggttt gactcacggg   2220
gatttccaag tctccacccc attgacgtca atgggagttt gttttggcac caaaatcaac   2280
gggactttcc aaaatgtcgt aacaactccg ccccattgac gcaaatgggc ggtaggcgtg   2340
tacggtggga ggtctatata agcagagctc gtttagtgaa ccgtcagatc gcctggagac   2400
gccatccacg ctgttttgac ctccatagaa gacaccggga ccgatccagc ctccgcggct   2460
cgcatctctc cttcacgcgc ccgccgccct acctgaggcc gccatccacg ccggttgagt   2520
cgcgttctgc cgcctcccgc ctgtggtgcc tcctgaactg cgtccgccgt ctaggtaagt   2580
```

-continued

```
ttaaagctca ggtcgagacc gggcctttgt ccggcgctcc cttggagcct acctagactc   2640
agccggctct ccacgctttg cctgaccctg cttgctcaac tctagttctc tcgttaactt   2700
aatgagacag atagaaactg gtcttgtaga aacagagtag tcgcctgctt ttctgccagg   2760
tgctgacttc tctcccctgg gcttttttct ttttctcagg ttgaaaagaa gaagacgaag   2820
aagacgaaga agacaaaccg tcgtcgacat ggcgccccgc agcgcccggc gaccectgct   2880 gctgctactg ctgttgctgc tgctcggcct catgcattgt gcgtcagcag caatgtttat   2940
ggtgaaaaat ggcaacggga ccgcgtgcat aatggccaac ttctctgctg ccttctcagt   3000
gaactacgac accaagagtg gccctaagaa catgaccctt gacctgccat cagatgccac   3060
agtggtgctc aaccgcagct cctgtggaaa agagaacact tctgacccca gtctcgtgat   3120
tgcttttgga agaggacata cactcactct caatttcacg agaaatgcaa cacgttacag   3180
cgtccagctc atgagttttg tttataactt gtcagacaca cacttttcc ccaatgcgag   3240 ctccaaagaa atcaagactg tggaatctat aactgacatc agggcagata tagataaaaa   3300
atacagatgt gttagtggca cccaggtcca catgaacaac gtgaccgtaa cgctccatga   3360
tgccaccatc caggcgtacc tttccaacag cagcttcagc cggggagaga cacgctgtga   3420
acaagacagg ccttcccccaa ccacagcgcc cctgcgcca cccagcccct cgccctcacc   3480
cgtgcccaag agccctctg tggacaagta caacgtgagc ggcaccaacg ggacctgcct   3540
gctggccagc atgggctgc agctgaacct cacctatgag aggaaggaca cacgacggt    3600 gacaaggctt ctcaacatca accccaacaa gacctcggcc agcgggagct gcggcgccca   3660
cctggtgact ctggagctgc acagcgaggg caccaccgtc ctgctcttcc agttcgggat   3720
gaatgcaagt tctagccggt ttttcctaca aggaatccag ttgaatacaa ttcttcctga   3780
cgccagagac cctgcctta aagctgccaa cggctccctg cgagcgctgc aggccacagt   3840
cggcaattcc tacaagtgca acgcggagga gcacgtccgt gtcacgaagg cgttttcagt   3900
caatatattc aaagtgtggg tccaggcttt caaggtggaa ggtggccagt ttggctctgt   3960
ggaggagtgt ctgctggacg agaacagcct cgaggacaat cctattgatt cctgctggcg   4020
tggagattct aactgggcac agaaccggat gaaactggct gactgtgccg tgggctttgg   4080
ctcttccact atgggaggga agggaggcga cctgtacact gttacaaaca gcgacgacga   4140
ccctgtcaat ccagcacccg gaaccttgag atatggtgca acgcgagacc gaccactttg   4200
gatcatcttt agcggaaaca tgaacatcaa gttgaagatg cctatgtaca tagctgggta   4260
caaaaccttc gacggcagag gagcccaagt gtacattggc aacggaggtc cctgcgtgtt   4320
catcaagcgt gttagtaatg tgatcattca cggtctgcac ctctatggct gttcaacaag   4380
cgtgctgggg aatgtgctga tcaatgagtc attcggtgtt gaacccgtgc acccacagga   4440
cggtgatgcg ttgacactga ggacagccac caatatctgg attgaccata acagtttctc   4500
taacagctca gatggcctgg tggatgtcac cttgagtagc acaggggtca caatcagcaa   4560
caatctgttc ttcaaccatc ataaggtgat gctgctgggc cacgacgatg cgtattccga   4620
cgataagagc atgaaagtga cggtggcctt taaccagttt ggtcctaact gtggacagcg   4680
gatgcctaga gccaggtacg gactggtgca cgtggccaac aacaactatg atccgtggac   4740
tatctatgca attggcggtt cttccaaccc gacgatactg agtgaaggga actcctttac   4800
cgctcccaat gagagctaca agaagcaggt caccatccgc ataggctgca aaactagttc   4860
atcctgtagc aactgggtgt ggcagtccac tcaagatgtc ttctacaacg agcttacttt   4920
cgttagcagt gggaaatacg aaggtggcaa catatacaca aagaaagagg ctttcaatgt   4980 gagaatggc aatgccactc cccagctcac caagaatgca ggggtgctca cctgctccct   5040
```

-continued

```
gagcaaacgg tgcggcggtg gtggcctcga ggatcagtca gcgcagatca tgctggatag   5100
cgtggtggag aagtacctga ggagtaacag gtcactgcgc aaggttgagc attccagaca   5160
cgacgctatc aacatcttca acgtggagaa gtacggtgct gtcggagacg ggaagcacga   5220
ctgcaccgaa gccttttcta cagcctggca agctgcctgc aagaatccct cagccatgct   5280
cctcgtgcct gggtctaaga agtttgtcgt gaataacctt ttcttcaatg accctgcca   5340
gccacacttt accttcaaag ttgatgggat catcgcagcc tatcagaacc cagctagctg   5400
gaagaacaat cggatctggt tgcagtttgc caaactgaca ggattcaccc tgatggggaa   5460
aggcgtgatc gacggacagg gcaaacagtg gtgggcaggg cagtgcaagt gggtcaatgg   5520
tagggagatt tgcaatgaca gggaccgtcc taccgctatc aagtttgatt tcagcacagg   5580
actgattatt caggggttga agctgatgaa tagtccagag tttcaccttg tgtttggcaa   5640
ttgtgaaggt gtgaagatca taggcattag cattacagca cctcgcgatt ctcccaatac   5700
ggacggcatt gacatcttcg cctccaagaa ctttcacctg caaagaata ccattggcac   5760
aggcgacgac tgcgtggcca ttggcactgg cagcagcaat atcgttatcg aagatttgat   5820
atgtggtcct gggcatggca taagcattgg aagcctgggt agagaaaact caagagctga   5880
agtcagctat gttcacgtta acggagcgaa gttcattgat acccagaacg gactgcgaat   5940
caaaacttgg caaggggaa gtggcatggc atctcacatc atctacgaga acgtcgagat   6000
gatcaattcc gagaacccca tactgattaa ccaattctat tgtacttccg cctctgcctg   6060
ccagaatcag agatcagccg tgcagattca ggacgtgaca tacaagaata tccgagggac   6120
gagcgctacc gctgccgcaa tacagctcaa atgttccgat agcatgccct gcaaagatat   6180
caagcttagt gatatctccc tcaaactgac tagcggaaag atagcgtcct gtctcaatga   6240
taacgcaaat ggctacttct cagggcatgt gatccctgca tgcaaaaacc ttagcccgag   6300
tgcgaaacgc aaagaatcca aatcccataa gcatccgaag actgtgatgg tcgagaacat   6360
gagagcctac gacaaaggga accggacgag gattctgctg ggctctcgac cgccaaactg   6420
taccaacaaa tgtcacggtt gttctccatg caaagctaaa ctggtgatag tgcatcgcat   6480
catgcctcaa gagtactatc cccagcgttg gatttgtagt tgccatggca agatctatca   6540
cccagaattc acgctgatcc ccatcgctgt gggtggtgcc ctggcggggc tggtcctcat   6600
cgtcctcatc gcctacctcg tcggcaggaa gaggagtcac gcaggctacc agactatcta   6660
gtaaggatct ttttccctct gccaaaaatt atggggacat catgaagccc cttgagcatc   6720
tgacttctgg ctaataaagg aaatttattt tcattgcaat agtgtgttgg aattttttgt   6780
gtctctcact cggaaggaca taagggcggc cgctagc                             6817
```

2. The nucleic acid sequence of the coding region for the Ara H1 I H2/h3 polyprotein:

```
                                                         SEQ ID NO: 8
ccgcctaatg agcgggcttt ttttcttag ggtgcaaaag gagagcctgt aagcgggcac      60
tcttccgtgg tctggtggat aaattcgcaa gggtatcatg gcggacgacc ggggttcgag    120
ccccgtatcc ggccgtccgc cgtgatccat gcggttaccg cccgcgtgtc gaacccaggt   180
gtgcgacgtc agacaacggg ggagtgctcc ttttggcttc cttcccttc ttccgcttcc    240
tcgctcactg actcgctgcg ctcggtcgtt cggctgcggc gagcggtatc agctcactca    300
aaggcggtaa tacggttatc cacagaatca ggggataacg caggaaagaa catgtgagca    360
aaaggccagc aaaaggccag gaaccgtaaa aaggccgcgt tgctggcgtt tttccatagg    420
```

-continued

```
ctccgccccc ctgacgagca tcacaaaaat cgacgctcaa gtcagaggtg gcgaaacccg    480
acaggactat aaagatacca ggcgtttccc cctggaagct ccctcgtgcg ctctcctgtt    540
ccgaccctgc cgcttaccgg atacctgtcc gcctttctcc cttcgggaag cgtggcgctt    600
tctcatagct cacgctgtag gtatctcagt tcggtgtagg tcgttcgctc caagctgggc    660
tgtgtgcacg aaccccccgt tcagcccgac cgctgcgcct tatccggtaa ctatcgtctt    720
gagtccaacc cggtaagaca cgacttatcg ccactggcag cagccactgg taacaggatt    780
agcagagcga ggtatgtagg cggtgctaca gagttcttga agtggtggcc taactacggc    840
tacactagaa gaacagtatt tggtatctgc gctctgctga agccagttac cttcggaaaa    900
agagttggta gctcttgatc cggcaaacaa accaccgctg gtagcggtgg ttttttttgtt    960 tgcaagcagc agattacgcg cagaaaaaaa ggatctcaag aagatccttt gatcttttct    1020
acggggtctg acgctcagtg gaacgaaaac tcacgttaag ggattttggt catgagatta    1080
tcaaaaagga tcttcaccta gatcctttta aattaaaaat gaagttttaa atcaatctaa    1140
agtatatatg agtaaacttg gtctgacagt taccaatgct taatcagtga ggcacctatc    1200
tcagcgatct gtctatttcg ttcatccata gttgcctgac tcctgcaaac cacgttgtgg    1260
tagaattggt aaagagagtc gtgtaaaata tcgagttcgc acatcttgtt gtctgattat    1320 tgattttttgg cgaaaccatt tgatcatatg acaagatgtg tatctacctt aacttaatga    1380
ttttgataaa aatcattagg taccccggct ctagatggca tgacattaac ctataaaaat    1440
aggcgtatca cgaggccctt tcgtctcgcg cgtttcggtg atgacggtga aaacctctga    1500
cacatgcagc tcccggagac ggtcacagct tgtctgtaag cggatgccgg gagcagacaa    1560
gcccgtcagg gcgcgtcagc gggtgttggc gggtgtcggg gctggcttaa ctatgcggca    1620
tcagagcaga ttgtactgag agtgcaccat atgcggtgtg aaataccgca cagatgcgta    1680
aggagaaaat accgcatcag attggctatt ggccattgca tacgttgtat ccatatcata    1740
atatgtacat ttatattggc tcatgtccaa cattaccgcc atgttgacat tgattattga    1800
ctagttatta atagtaatca attacggggt cattagttca tagcccatat atggagttcc    1860
gcgttacata acttacggta aatggcccgc ctggctgacc gcccaacgac ccccgcccat    1920
tgacgtcaat aatgacgtat gttcccatag taacgccaat agggactttc cattgacgtc    1980
aatgggtgga gtatttacgg taaactgccc acttggcagt acatcaagtg tatcatatgc    2040
caagtacgcc ccctattgac gtcaatgacg gtaaatggcc cgcctggcat tatgcccagt    2100
acatgacctt atgggacttt cctacttggc agtacatcta cgtattagtc atcgctatta    2160
ccatggtgat gcggttttgg cagtacatca atgggcgtgg atagcggttt gactcacggg    2220
gatttccaag tctccacccc attgacgtca atgggagttt gttttggcac caaaatcaac    2280
gggactttcc aaaatgtcgt aacaactccg ccccattgac gcaaatgggc ggtaggcgtg    2340
tacggtggga ggtctatata agcagagctc gtttagtgaa ccgtcagatc gcctggagac    2400
gccatccacg ctgttttgac ctccatagaa gacaccggga ccgatccagc ctccgcggct    2460
cgcatctctc cttcacgcgc ccgccgccct acctgaggcc gccatccacg ccggttgagt    2520
cgcgttctgc cgcctcccgc ctgtggtgcc tcctgaactg cgtccgccgt ctaggtaagt    2580
ttaaagctca ggtcgagacc gggcctttgt ccggcgctcc cttggagcct acctagactc    2640
agccggctct ccacgctttg cctgaccctg cttgctcaac tctagttctc tcgttaactt    2700
aatgagacag atagaaactg gtcttgtaga aacagagtag tcgcctgctt ttctgccagg    2760
tgctgacttc tctcccctgg gctttttttct ttttctcagg ttgaaaagaa gaagacgaag    2820
```

```
aagacgaaga agacaaaccg tcgtcgacat ggcgccccgc agcgcccggc gaccgctgct    2880
gctgctactg ctgttgctgc tgctcggcct catgcattgt gcgtcagcag caatgtttat    2940
ggtgaaaaat ggcaacggga ccgcgtgcat aatggccaac ttctctgctg ccttctcagt    3000
gaactacgac accaagagtg ccctaagaa catgacccct tgacctgccat cagatgccac    3060 agtggtgctc aaccgcagct cctgtggaaa agagaacact tctgacccca gtctcgtgat    3120
tgcttttgga agaggacata cactcactct caatttcacg agaaatgcaa cacgttacag    3180
cgttcagctc atgagttttg tttataactt gtcagacaca cacccttttcc ccaatgcgag    3240 ctccaaagaa atcaagactg tggaatctat aactgacatc agggcagata tagataaaaa    3300
atacagatgt gttagtggca cccaggtcca catgaacaac gtgaccgtaa cgctccatga    3360
tgccaccatc caggcgtacc tttccaacag cagcttcagc aggggagaga cacgctgtga    3420
acaagacagg ccttccccaa ccacagcgcc ccctgcgcca cccagcccct cgccctcacc    3480
cgtgcccaag agccccctctg tggacaagta caacgtgagc ggcaccaacg ggacctgcct    3540 gctgccagc atgggctgc agctgaacct cacctatgag aggaaggaca acacgacggt    3600
gacaaggctt ctcaacatca accccaacaa gaccctcggcc agcgggagct gcggcgccca    3660
cctggtgact ctggagctgc acagcgaggg caccaccgtc ctgctcttcc agttcgggat    3720
gaatgcaagt tctagccggt ttttcctaca aggaatccag ttgaatacaa ttcttcctga    3780
cgccagagac cctgccttta aagctgccaa cggctccctg cgagcgctgc aggccacagt    3840
cggcaattcc tacaagtgca acgcggagga gcacgtccgt gtcacgaagg cgtttcagt    3900 caatatattc aaagtgtggg tccaggcttt caaggtggaa ggtggccagt ttggctctgt    3960
ggaggagtgt ctgctggacg agaacagcct cgagaagtcc agccctacc agaagaaaac    4020 cgagaacccc tgcgcccagc ggtgcctgca gtcttgtcag caggaacccg acgacctgaa    4080
gcagaaggcc tgcgagagcc ggtgcaccaa gctggaatac accccagat cgtgtacga    4140 ccctagaggc cacaccggca ccaccaacca gagaagccct ccaggcgagc ggaccagagg    4200
cagacagcct ggcgactacg acgacgacag acggcagccc agaagagaag agggcggcag    4260
atggggacct gccggcccta gagagagaga acgcgaggaa gattggagac agcccagaga    4320
ggactggcgg aggccttctc accagcagcc ccggaagatc agacccgagg cagagaagg    4380 cgagcaggaa tggggcacac ctggctctca cgtgcgcgag gaaaccagcc ggaacaaccc    4440
cttctacttc ccctcccggc ggttcagcac cagatacggc aaccagaacg gccggatcag    4500
agtgctgcag agattcgacc agcggagccg gcagttccag aacctgcaga accaccggat    4560
cgtgcagatc gaggccaagc ccaacaccct ggtgctgccc aaacacgccg acgccgacaa    4620
catcctcgtg atccagcagg ccaggccac cgtgacagtg ccaacggca acaacagaaa    4680 gagcttcaac ctggacgagg ccacgccct gagaatcccc agcggcttca tcagctacat    4740
cctgaacaga cacgacaatc agaacctgag ggtggccaag atcagcatgc ccgtgaacac    4800
ccctggccag ttcgaggact tcttccccgc atcctcccgg gaccagagca gctacctgca    4860
gggcttcagc cggaatacc tggaagccgc cttcaacgcc gagttcaacg agatcagacg    4920
ggtgctgctg aagagaacg ctggcggaga gcaggaagaa cggggccaga gaagatggtc    4980
caccagaagc agcgagaaca acgagggcgt gatcgtgaag gtgtccaaag aacacgtgga    5040
agaactgacc aagcacgcca agagcgtgtc caagaagggc tccgaggaag agggggacat    5100
caccaacccc atcaatctga gagagggcga gcccgacctg agcaacaact tcggcaagct    5160
gttcgaagtg aagcccgaca agaagaaccc ccagctgcag gacctggaca tgatgctgac    5220
ctgcgtggaa atcaaagagg gggccctgat gctgccacac ttcaactcca aagccatggt    5280
```

```
catcgtggtc gtgaacaagg gcaccggcaa cctggaactg gtggccgtgc ggaaagagca   5340
gcagcagaga ggccgcagag aggaagaaga ggacgaggac gaagaagaag agggatccaa   5400
ccgggaagtg cggcggtaca ccgccagact gaaagaaggc gacgtgttca tcatgcctgc   5460
cgcccacccc gtggccatca atgcctctag cgagctgcat ctgctgggct cggcattaa   5520 cgccgagaac aatcaccgga tctttctggc cggcgacaaa gacaacgtga tcgaccagat   5580
cgagaagcag gccaaggacc tggccttttcc cggctctggc gaacaagtgg aaaagctgat   5640
caagaaccag aaagaaagcc acttcgtgtc cgccagaccc cagagccagt ctcagagccc   5700
tagctccccc gagaaagagt ctcctgagaa agaggaccag gaagaggaaa accagggcgg   5760
caagggccct ctgctgagca tcctgaaggc cttcaatggc ggcgaggca ggcagcagtg   5820 ggaactgcag ggcgacagaa gatgccagtc ccagctggaa cgggccaacc tgaggccttg   5880
cgagcagcac ctgatgcaga aaatccagcg cgacgaggac agctacggcc gggatcctta   5940
cagccccagc caggacccctt actccctag ccaggatcc cacagaaggg accctacag   6000 ccctagcccc tacgatagaa gaggcgccgg aagcagccag caccaggaaa gatgctgcaa   6060
cgagctgaac gagtttgaga caaccagcc ctgcatgtgc gaggcctgc agcagatcat   6120 ggaaatcag agcgaccggc tgcagggacg gcagcaggaa cagcagttca agagagagct   6180 gcggaaacctg ccccagcagt gtggactgag agccccccag agatgcgacc tggaagtgga   6240
aagcggcggc agagatcggt acggcggagg gggcgtgacc ttcagacagg gcggagaaga   6300
gaatgagtgc cagtttcagc ggctgaacgc ccagaggccc gacaacagaa tcgagagcga   6360
gggcggctac atcgagacat ggaaccccaa caaccaggaa tttcagtgcg ctggggtggc   6420
cctgagcagg accgtgctga aagaaatgc cctgaggcgg cccttctaca gcaacgcccc   6480
cctggaaatc tacgtgcagc agggcagcgg ctacttcggc ctgatctttc ccggatgccc   6540
ctccacctat gaggaacccg ctcaggaagg cagacggtat cagagccaga agcctagcag   6600
acggttccaa gtgggccagg acgatcccag ccaacagcag caggactctc accagaaggt   6660
gcaccgcttc gacgagggcg acctgatcgc tgtgccaacc ggcgtggcct tctggatgta   6720
caacgacgag gataccgacg tcgtgaccgt gacccctgagc gacaccagct ccatccacaa   6780
ccagctggac cagttccccca ggcggtttta cctggccggc aatcaggaac aggaattct   6840 gagataccag cagcagcagg gctccagacc ccactacaga cagatcagcc ctagagtcgcg   6900 gggcgacgaa caggaaaatg agggcagcaa catcttctcc ggctttgccc aggaatttct   6960
gcagcacgcc ttccaggtgg accggcagac cgtggaaaac ctgagaggcg agaacgagag   7020
agaggaacag ggcgccatcg tgactgtgaa gggcggcctg aggatcctga gccccgacga   7080
agaggatgag tcctctagaa gccccccccaa ccgccgggaa gagttcgatg aggaccgcag   7140
cagacctcag cagcggggga agtacgacga gaacaggcgg ggctacaaga acggcatcga   7200
ggaaacaatc tgcagcgcca gcgtgaagaa gaatctgggc cggtccagca accccgacat   7260
ctacaatcca caggccggca gcctgcggag cgtgaacgaa ctggatctgc ccatcctggg   7320
atggctgggc ctgtctgccc agcacggcac catctaccgg aacgccatgt tcgtgcctca   7380
ctacaccctg aatgcccaca ccatcgtggt ggctctgaac ggccgcgccc acgtccaagt   7440
ggtggacaga acggcaatc gggtgtacga tgaagaactg caggaaggac acgtcctggt   7500 ggtgcccag aattttgccg tggccgccaa ggccccagtcc gagaactatg agtatctggc   7560
cttcaagacc gacagccggc cctctatcgc caatcaagcc ggcgagaaca gcatcatcga   7620
caacctgccc gaggaagtgg tggccaacag ctaccggctg cctagagagc aggcccggca   7680
```

```
gctgaagaac aacaaccctt tcaagttctt cgtgccccca ttcgaccacc agagcatgag 7740
agaggtggcc gaattcacgc tgatccccat cgctgtgggt ggtgccctgg cggggctggt 7800
cctcatcgtc ctcatcgcct acctcgtcgg caggaagagg agtcacgcag gctaccagac 7860
tatctagtaa ggatcttttt ccctctgcca aaaattatgg ggacatcatg aagccccttg 7920
agcatctgac ttctggctaa taaaggaaat ttattttcat tgcaatagtg tgttggaatt 7980
ttttgtgtct ctcactcgga aggacataag ggcggccgct agc            8023
```

The amino acid sequence of the coding region for the Ara H1 I H2 I H3 polyprotein chimeric construct, as follows:

SEQ ID NO:9-AraH-LAMP
<220>
<221> SIGNAL
<222> (1) . . . (27)

<220>

<221> N-LAMP

<222> (28) . . . (380)

<220>

<221> AraH1

<222> (383) . . . (983)

<220>

<221> AraH2

<222> (988) . . . (1138)

<220>

<221> AraH3

<222> (1143) . . . (1634)

<220>

<221> TM/CYTO

<222> (1637) . . . (1672)

<400> 7

Met Ala Pro Arg Ser Ala Arg Arg Pro Leu Leu Leu Leu Leu Leu Leu 5 10 15

Leu Leu Leu Gly Leu Met His Cys Ala Ser Ala Ala Met Phe Met Val 20 25 30

Lys Asn Gly Asn Gly Thr Ala Cys Ile Met Ala Asn Phe Ser Ala Ala 35 40 45

Phe Ser Val Asn Tyr Asp Thr Lys Ser Gly Pro Lys Asn Met Thr Leu 50 55 60

Asp Leu Pro Ser Asp Ala Thr Val Val Leu Asn Arg Ser Ser Cys Gly 70 75 80

Lys Glu Asn Thr Ser Asp Pro Ser Leu Val Ile Ala Phe Gly Arg Gly 85 90 95

His Thr Leu Thr Leu Asn Phe Thr Arg Asn Ala Thr Arg Tyr Ser Val 100 105 110

Gln Leu Met Ser Phe Val Tyr Asn Leu Ser Asp Thr His Leu Phe Pro 115 120 125

Asn Ala Ser Ser Lys Glu Ile Lys Thr Val Glu Ser Ile Thr Asp Ile 130 135 140

Arg Ala Asp Ile Asp Lys Lys Tyr Arg Cys Val Ser Gly Thr Gln Val 145 150 155 160

His Met Asn Asn Val Thr Val Thr Leu His Asp Ala Thr Ile Gln Ala 165 170 175

Tyr Leu Ser Asn Ser Ser Phe Ser Arg Gly Glu Thr Arg Cys Glu Gln 180 185 190

Asp Arg Pro Ser Pro Thr Thr Ala Pro Pro Ala Pro Pro Ser Pro Ser 195 200 205

Pro Ser Pro Val Pro Lys Ser Pro Ser Val Asp Lys Tyr Asn Val Ser 210 215 220

Gly Thr Asn Gly Thr Cys Leu Leu Ala Ser Met Gly Leu Gln Leu Asn 225 230 235 240

Leu Thr Tyr Glu Arg Lys Asp Asn Thr Thr Val Thr Arg Leu Leu Asn 245 250 255

Ile Asn Pro Asn Lys Thr Ser Ala Ser Gly Ser Cys Gly Ala His Leu 260 265 270

Val Thr Leu Glu Leu His Ser Glu Gly Thr Thr Val Leu Leu Phe Gln 275 280 285

Phe Gly Met Asn Ala Ser Ser Ser Arg Phe Phe Leu Gln Gly Ile Gln 290 295 300

Leu Asn Thr Ile Leu Pro Asp Ala Arg Asp Pro Ala Phe Lys Ala Ala 305 310 315 320

Asn Gly Ser Leu Arg Ala Leu Gln Ala Thr Val Gly Asn Ser Tyr Lys 325 330 335

Cys Asn Ala Glu Glu His Val Arg Val Thr Lys Ala Phe Ser Val Asn 340 345 350

Ile Phe Lys Val Trp Val Gln Ala Phe Lys Val Glu Gly Gly Gln Phe 355 360 365

Gly Ser Val Glu Glu Cys Leu Leu Asp Glu Asn Ser Leu Glu Lys Ser 370 375 380

Ser Pro Tyr Gln Lys Lys Thr Glu Asn Pro Cys Ala Gln Arg Cys Leu 385 390 395 400

Gln Ser Cys Gln Gln Glu Pro Asp Asp Leu Lys Gln Lys Ala Cys Glu 405 410 415

Ser Arg Cys Thr Lys Leu Glu Tyr Asp Pro Arg Cys Val Tyr Asp Pro 420 425 430

Arg Gly His Thr Gly Thr Thr Asn Gln Arg Ser Pro Pro Gly Glu Arg 435 440 445

Thr Arg Gly Arg Gln Pro Gly Asp Tyr Asp Asp Asp Arg Arg Gln Pro 450 455 460

Arg Arg Glu Glu Gly Gly Arg Trp Gly Pro Ala Gly Pro Arg Glu Arg
465 470 475 480
Glu Arg Glu Glu Asp Trp Arg Gln Pro Arg Glu Asp Trp Arg Arg Pro
485 490 495
Ser His Gln Gln Pro Arg Lys Ile Arg Pro Gly Arg Glu Gly Glu
500 505 510
Gln Glu Trp Gly Thr Pro Gly Ser His Val Arg Glu Glu Thr Ser Arg
515 520 525
Asn Asn Pro Phe Tyr Phe Pro Ser Arg Arg Phe Ser Thr Arg Tyr Gly
530 535 540
Asn Gln Asn Gly Arg Ile Arg Val Leu Gln Arg Phe Asp Gln Arg Ser
545 550 555 560
Arg Gln Phe Gln Asn Leu Gln Asn His Arg Ile Val Gln Ile Glu Ala
565 570 575
Lys Pro Asn Thr Leu Val Leu Pro Lys His Ala Asp Ala Asp Asn Ile
580 585 590
Leu Val Ile Gln Gln Gly Gln Ala Thr Val Thr Val Ala Asn Gly Asn
595 600 605
Asn Arg Lys Ser Phe Asn Leu Asp Glu Gly His Ala Leu Arg Ile Pro
610 615 620
Ser Gly Phe Ile Ser Tyr Ile Leu Asn Arg His Asp Asn Gln Asn Leu
625 630 635 640
Arg Val Ala Lys Ile Ser Met Pro Val Asn Thr Pro Gly Gln Phe Glu
645 650 655
Asp Phe Phe Pro Ala Ser Ser Arg Asp Gln Ser Ser Tyr Leu Gln Gly
660 665 670
Phe Ser Arg Asn Thr Leu Glu Ala Ala Phe Asn Ala Glu Phe Asn Glu
675 680 685
Ile Arg Arg Val Leu Leu Glu Glu Asn Ala Gly Gly Glu Gln Glu Glu
690 695 700
Arg Gly Gln Arg Arg Trp Ser Thr Arg Ser Ser Glu Asn Asn Glu Gly
705 710 715 720
Val Ile Val Lys Val Ser Lys Glu His Val Glu Glu Leu Thr Lys His
725 730 735
Ala Lys Ser Val Ser Lys Lys Gly Ser Glu Glu Glu Gly Asp Ile Thr
740 745 750
Asn Pro Ile Asn Leu Arg Glu Gly Glu Pro Asp Leu Ser Asn Asn Phe
755 760 765
Gly Lys Leu Phe Glu Val Lys Pro Asp Lys Lys Asn Pro Gln Leu Gln
770 775 780
Asp Leu Asp Met Met Leu Thr Cys Val Glu Ile Lys Glu Gly Ala Leu
785 790 795 800
Met Leu Pro His Phe Asn Ser Lys Ala Met Val Ile Val Val Val Asn
805 810 815
Lys Gly Thr Gly Asn Leu Glu Leu Val Ala Val Arg Lys Glu Gln Gln
820 825 830
Gln Arg Gly Arg Arg Glu Glu Glu Asp Glu Asp Glu Glu Glu Glu
835 840 845
Gly Ser Asn Arg Glu Val Arg Arg Tyr Thr Ala Arg Leu Lys Glu Gly
850 855 860
Asp Val Phe Ile Met Pro Ala Ala His Pro Val Ala Ile Asn Ala Ser
865 870 875 880
Ser Glu Leu His Leu Leu Gly Phe Gly Ile Asn Ala Glu Asn Asn His
885 890 895
Arg Ile Phe Leu Ala Gly Asp Lys Asp Asn Val Ile Asp Gln Ile Glu
900 905 910
Lys Gln Ala Lys Asp Leu Ala Phe Pro Gly Ser Gly Glu Gln Val Glu
915 920 925
Lys Leu Ile Lys Asn Gln Lys Glu Ser His Phe Val Ser Ala Arg Pro
930 935 940
Gln Ser Gln Ser Gln Ser Pro Ser Ser Pro Glu Lys Glu Ser Pro Glu
945 950 955 960
Lys Glu Asp Gln Glu Glu Glu Asn Gln Gly Gly Lys Gly Pro Leu Leu
965 970 975
Ser Ile Leu Lys Ala Phe Asn Gly Gly Gly Arg Gln Gln Trp Glu
980 985 990
Leu Gln Gly Asp Arg Arg Cys Gln Ser Gln Leu Glu Arg Ala Asn Leu
995 1000 1005
Arg Pro Cys Glu Gln His Leu Met Gln Lys Ile Gln Arg Asp Glu
1010 1015 1020
Asp Ser Tyr Gly Arg Asp Pro Tyr Ser Pro Ser Gln Asp Pro Tyr
1025 1030 1035
Ser Pro Ser Gln Asp Pro Asp Arg Arg Asp Pro Tyr Ser Pro Ser
1040 1045 1050
Pro Tyr Asp Arg Arg Gly Ala Gly Ser Ser Gln His Gln Glu Arg
1055 1060 1065
Cys Cys Asn Glu Leu Asn Glu Phe Glu Asn Asn Gln Arg Cys Met
1070 1075 1080
Cys Glu Ala Leu Gln Gln Ile Met Glu Asn Gln Ser Asp Arg Leu
1085 1090 1095
Gln Gly Arg Gln Gln Glu Gln Gln Phe Lys Arg Glu Leu Arg Asn
1100 1105 1110
Leu Pro Gln Gln Cys Gly Leu Arg Ala Pro Gln Arg Cys Asp Leu
1115 1120 1125
Glu Val Glu Ser Gly Gly Arg Asp Arg Tyr Gly Gly Gly Gly Val
1130 1135 1140
Thr Phe Arg Gln Gly Gly Glu Glu Asn Glu Cys Gln Phe Gln Arg
1145 1150 1155

Leu Asn Ala Gln Arg Pro Asp Asn Arg Ile Glu Ser Glu Gly Gly
1160 1165 1170
Tyr Ile Glu Thr Trp Asn Pro Asn Asn Gln Glu Phe Gln Cys Ala
1175 1180 1185
Gly Val Ala Leu Ser Arg Thr Val Leu Arg Arg Asn Ala Leu Arg
1190 1195 1200
Arg Pro Phe Tyr Ser Asn Ala Pro Leu Glu Ile Tyr Val Gln Gln
1205 1210 1215
Gly Ser Gly Tyr Phe Gly Leu Ile Phe Pro Gly Cys Pro Ser Thr
1220 1225 1230
Tyr Glu Glu Pro Ala Gln Glu Gly Arg Arg Tyr Gln Ser Gln Lys
1235 1240 1245
Pro Ser Arg Arg Phe Gln Val Gly Gln Asp Asp Pro Ser Gln Gln
1250 1255 1260
Gln Gln Asp Ser His Gln Lys Val His Arg Phe Asp Glu Gly Asp
1265 1270 1275
Leu Ile Ala Val Pro Thr Gly Val Ala Phe Trp Met Tyr Asn Asp
1280 1285 1290
Glu Asp Thr Asp Val Val Thr Val Thr Leu Ser Asp Thr Ser Ser
1295 1300 1305
Ile His Asn Gln Leu Asp Gln Phe Pro Arg Arg Phe Tyr Leu Ala
1310 1315 1320
Gly Asn Gln Glu Gln Glu Phe Leu Arg Tyr Gln Gln Gln Gln Gly
1325 1330 1335
Ser Arg Pro His Tyr Arg Gln Ile Ser Pro Arg Val Arg Gly Asp
1340 1345 1350
Glu Gln Glu Asn Glu Gly Ser Asn Ile Phe Ser Gly Phe Ala Gln
1355 1360 1365
Glu Phe Leu Gln His Ala Phe Gln Val Asp Arg Gln Thr Val Glu
1370 1375 1380
Asn Leu Arg Gly Glu Asn Glu Arg Glu Glu Gln Gly Ala Ile Val
1385 1390 1395
Thr Val Lys Gly Gly Leu Arg Ile Leu Ser Pro Asp Glu Glu Asp
1400 1405 1410
Glu Ser Ser Arg Ser Pro Pro Asn Arg Arg Glu Glu Phe Asp Glu
1415 1420 1425
Asp Arg Ser Arg Pro Gln Gln Arg Gly Lys Tyr Asp Glu Asn Arg
1430 1435 1440
Arg Gly Tyr Lys Asn Gly Ile Glu Glu Thr Ile Cys Ser Ala Ser
1445 1450 1455
Val Lys Lys Asn Leu Gly Arg Ser Ser Asn Pro Asp Ile Tyr Asn
1460 1465 1470
Pro Gln Ala Gly Ser Leu Arg Ser Val Asn Glu Leu Asp Leu Pro
1475 1480 1485
Ile Leu Gly Trp Leu Gly Leu Ser Ala Gln His Gly Thr Ile Tyr
1490 1495 1500
Arg Asn Ala Met Phe Val Pro His Tyr Thr Leu Asn Ala His Thr
1505 1510 1515
Ile Val Val Ala Leu Asn Gly Arg Ala His Val Gln Val Val Asp
1520 1525 1530
Ser Asn Gly Asn Arg Val Tyr Asp Glu Glu Leu Gln Glu Gly His
1535 1540 1545
Val Leu Val Val Pro Gln Asn Phe Ala Val Ala Ala Lys Ala Gln
1550 1555 1560
Ser Glu Asn Tyr Glu Tyr Leu Ala Phe Lys Thr Asp Ser Arg Pro
1565 1570 1575
Ser Ile Ala Asn Gln Ala Gly Glu Asn Ser Ile Ile Asp Asn Leu
1580 1585 1590
Pro Glu Glu Val Val Ala Asn Ser Tyr Arg Leu Pro Arg Glu Gln
1595 1600 1605
Ala Arg Gln Leu Lys Asn Asn Pro Phe Lys Phe Phe Val Pro
1610 1615 1620
Pro Phe Asp His Gln Ser Met Arg Glu Val Ala Glu Phe Thr Leu
1625 1630 1635
Ile Pro Ile Ala Val Gly Gly Ala Leu Ala Gly Leu Val Leu Ile
1640 1645 1650
Val Leu Ile Ala Tyr Leu Val Gly Arg Lys Arg Ser His Ala Gly
1655 1660 1665
Tyr Gln Thr Ile
1670

The invention claimed is:

1. A method of treating a peanut allergy in a subject in need thereof, the method comprising administering to the subject a pharmaceutically effective amount of an isolated or purified nucleic acid molecule encoding a polypeptide comprising the amino acid sequence of SEQ ID NO: 9.

2. The method of claim 1, wherein the nucleic acid molecule is administered therapeutically to the subject suffering from an allergic reaction.

3. The method of claim 1, wherein the nucleic acid molecule is administered prophylactically to the subject who suffers from an allergic reaction.

4. The method of claim 1, wherein the subject is a human.

5. The method of claim 1, wherein the nucleic acid molecule comprises DNA.

6. The method of claim 5, wherein the nucleic acid molecule is administered therapeutically to the subject suffering from an allergic reaction.

7. The method of claim 5, wherein the nucleic acid molecule is administered prophylactically to the subject who suffers from an allergic reaction.

8. The method of claim 5, wherein the subject is a human.

9. The method of claim 1, wherein the nucleic acid molecule further comprises an expression vector.

10. The method of claim 9, wherein the nucleic acid molecule is administered therapeutically to the subject suffering from an allergic reaction.

11. The method of claim 9, wherein the nucleic acid molecule is administered prophylactically to the subject who suffers from an allergic reaction.

12. The method of claim 9, wherein the subject is a human.

13. A method of treating a peanut allergy in a subject in need thereof, the method comprising administering to the subject a composition comprising a pharmaceutically effective amount of an isolated or purified nucleic acid molecule encoding a polypeptide comprising the amino acid sequence of SEQ ID NO: 9.

14. The method of claim 13, wherein the composition is administered therapeutically to the subject suffering from an allergic reaction.

15. The method of claim 13, wherein the nucleic acid molecule is administered prophylactically to the subject who suffers from an allergic reaction.

16. The method of claim 13, wherein the subject is a human.

17. The method of claim 13, wherein the nucleic acid molecule comprises DNA.

18. The method of claim 17, wherein the composition is administered therapeutically to the subject suffering from an allergic reaction.

19. The method of claim 17, wherein the nucleic acid molecule is administered prophylactically to the subject who suffers from an allergic reaction.

20. The method of claim 17, wherein the subject is a human.

21. The method of claim 13, wherein the nucleic acid molecule further comprises an expression vector.

22. The method of claim 21, wherein the composition is administered therapeutically to the subject suffering from an allergic reaction.

23. The method of claim 21, wherein the nucleic acid molecule is administered prophylactically to the subject who suffers from an allergic reaction.

24. The method of claim 21, wherein the subject is a human.

25. The method of claim 1, wherein the method reduces an IgE response in the subject.

26. The method of claim 25, wherein the reduction of the IgE response occurs in at least 20% of all subjects.

27. The method of claim 13, wherein the method reduces an IgE response in the subject.

28. The method of claim 27, wherein the reduction of the IgE response occurs in at least 20% of all subjects.

* * * * *

UNITED STATES PATENT AND TRADEMARK OFFICE
CERTIFICATE OF CORRECTION

PATENT NO. : 10,072,053 B2  
APPLICATION NO. : 15/663871  
DATED : September 11, 2018  
INVENTOR(S) : William Hearl and Teri Heiland Page 1 of 1

It is certified that error appears in the above-identified patent and that said Letters Patent is hereby corrected as shown below:

On the Title Page

In the Related U.S. Application Data item (62) should read:
--Division of application No. 14/407,410, filed on May 6, 2015, which is a National Stage Application of International Application No. PCT/US2012/042552, filed on June 15, 2012.--

Signed and Sealed this  
Twenty-fifth Day of June, 2019

Andrei Iancu  
*Director of the United States Patent and Trademark Office*